(12) United States Patent
Lau et al.

(10) Patent No.: US 10,472,688 B2
(45) Date of Patent: Nov. 12, 2019

(54) COMPOSITIONS AND METHODS FOR PRODUCING PODOPHYLLOTOXIN DERIVATIVES

(71) Applicant: The Board of Trustees of the Leland Stanford Junior University, Stanford, CA (US)

(72) Inventors: Warren Lau, Stanford, CA (US); Elizabeth Sattely, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days.

(21) Appl. No.: 15/242,525

(22) Filed: Aug. 20, 2016

(65) Prior Publication Data
US 2017/0088872 A1     Mar. 30, 2017

Related U.S. Application Data

(60) Provisional application No. 62/208,385, filed on Aug. 21, 2015.

(51) Int. Cl.
| C12N 9/10 | (2006.01) |
| C12N 9/02 | (2006.01) |
| C12P 17/18 | (2006.01) |

(52) U.S. Cl.
CPC ............ *C12Y 114/21* (2013.01); *C12N 9/001* (2013.01); *C12N 9/0008* (2013.01); *C12N 9/0071* (2013.01); *C12N 9/0073* (2013.01); *C12N 9/1007* (2013.01); *C12P 17/181* (2013.01); *C12Y 102/01* (2013.01); *C12Y 103/05001* (2013.01); *C12Y 114/11* (2013.01); *C12Y 114/13* (2013.01); *C12Y 201/01* (2013.01); *C12Y 201/01042* (2013.01)

(58) Field of Classification Search
CPC ... C12P 17/181; C12N 9/1007; C12N 9/0008; C12N 9/001; C12N 9/0071; C12N 9/0073; C12Y 201/01; C12Y 114/21; C12Y 201/01042; C12Y 114/11; C12Y 114/13; C12Y 102/01; C12Y 103/05001
See application file for complete search history.

(56) References Cited

U.S. PATENT DOCUMENTS

2009/0070897 A1* 3/2009 Goldman ............. C07K 14/415
                                                                    800/281

FOREIGN PATENT DOCUMENTS

| WO | WO 2008005631 | * | 1/2008 | ............... A01H 5/02 |
| WO | WO 2015103711 | * | 7/2015 | ............... C12P 17/12 |

OTHER PUBLICATIONS

Xia et al., (Phytochemistry. Nov. 2000;55(6):537-49). (Year: 2000).*
Marques et al., (J. Biol. Chem. 288:466-479(2013). (Year: 2013).*
(Continued)

*Primary Examiner* — Jana A Hines
(74) *Attorney, Agent, or Firm* — KPPB LLP

(57) ABSTRACT

The present invention provides compositions and methods for biosynthetically producing podophyllotoxin intermediates and derivatives including enzymes and their equivalents involved in the biosynthetic production of podophyllotoxin intermediates and derivatives.

19 Claims, 53 Drawing Sheets

Specification includes a Sequence Listing.

(56) References Cited

OTHER PUBLICATIONS

Bhattacharyya et al., "De novo transcriptome analysis using 454 pyrosequencing of the Himalayan Mayapple, Podophyllum hexandrum", BMC Genomics, vol. 14, No. 748, Nov. 1, 2013, 13 pgs.

Brown et al., "De novo production of the plant-derived alkaloid strictosidine in yeast", Proceedings of the National Academy of Sciences of the United States of America, vol. 112, No. 11, Mar. 17, 2015, pp. 3205-3210.

Canel et al., "Podophyllotoxin", Phytochemistry, vol. 54, No. 2, May 1, 2000, pp. 115-120.

Cimermancic et al., "Insights into Secondary Metabolism from a Global Analysis of Prokaryotic Biosynthetic Gene Clusters", Cell, vol. 158, No. 2, Jul. 17, 2014, pp. 412-421.

Davin et al., "Stereoselective Bimolecular Phenoxy Radical Coupling by an Auxiliary (Dirigent) Protein Without an Active Center", Science, vol. 275, No. 5298, Jan. 17, 1997, pp. 362-367.

De Luca et al., "Mining the Biodiversity of Plants: A Revolution in the Making", Science, vol. 336, No. 6089, Jun. 29, 2012, pp. 1658-1661.

Dinkova-Kostova et al., "(+)-Pinoresinol/(+)-Lariciresinol Reductase from Forsythia intermedia: Protein Purification, cDNA Cloning, Heterologous Expression and Comparison to Isoflavone Reductase", Journal of Biology Chemistry, vol. 271, No. 46, Nov. 15, 1996, pp. 29473-29482.

Ehlting et al., "Three 4-coumarate:coenzyme A ligases in *Arabidopsis thaliana* represent two evolutionarily divergent classes in angiosperms", The Plant Journal, vol. 19, No. 1, Jul. 1999, pp. 9-20.

Engler et al., "A One Pot, One Step, Precision Cloning Method with High Throughput Capability", PLoS ONE, vol. 3, No. 11, e3647, Nov. 5, 2008, 7 pgs.

Gibson et al., "Enzymatic assembly of DNA molecules up to several hundred kilobases", Nature Methods, vol. 6, No. 5, May 2009, pp. 343-345.

Giddings et al., "A stereoselective hydroxylation step of alkaloid biosynthesis by a unique cytochrome p450 in Catharanthus Roseus", Journal of Biological Chemistry, vol. 286, No. 19, May 13, 2011, pp. 16751-16757.

Gietz et al., "High-efficiency yeast transformation using the LiAc/SS carrier DNA/PEG method", Nature Protocols, vol. 2, No. 1, 2007, pp. 31-34.

Gordaliza et al., "Podophyllotoxin: distribution, sources, applications and new cytotoxic derivatives", Toxicon, vol. 44, No. 4, Sep. 15, 2004, pp. 441-459.

Hoffmann et al., "Purification, Cloning, and Properties of an Acyltransferase Controlling Shikimate and Quinate Ester Intermediates in Phenylpropanoid Metabolism", Journal of Biological Chemistry, vol. 278, No. 1, Jan. 3, 2003, pp. 95-103.

Huang et al., "CAP3: A DNA Sequence Assembly Program", Genome Research, vol. 9, No. 9, Sep. 1999, pp. 868-877.

Jackson et al., "Aryltetralin lignans from Podophyllum hexandrum and Podophyllum peltatum", Phytochemistry, vol. 23, No. 5, 1984, pp. 1147-1152.

Jackson et al., "Biosynthesis of Podophyllum lignans—II. Interconversions of aryltetralin lignans in Podophyllum hexandrum", Phytochemistry, vol. 23, No. 5, 1984, pp. 1037-1042.

Kamal et al., "Facile and efficient one-pot synthesis of 4β-arylaminopodophyllotoxins: synthesis of DNA topoisomerase II inhibitors (NPF and W-68)", Bioorganic & Medicinal Chemistry Letters, vol. 10, No. 18, Sep. 2000, pp. 2059-2062.

Kamil et al., "Biosynthesis of the lignans α- and β-peltatin", Phytochemistry, vol. 25, No. 9, 1986, pp. 2089-2092.

Kamil et al., "Biosynthetic relationship of aryltetralin lactone lignans to dibenzylbutyrolactone lignans", Phytochemistry, vol. 25, No. 9, 1986, pp. 2093-2102.

Kawazu et al., "Isolation of the Cytotoxic Constituent Deoxypodophyllotoxin from the Leaves of Juniperus chinensis", Scientific Reports of the Faculty of Agriculture, Okayama University, vol. 86, No. 1, Feb. 1997, pp. 1-5.

Kumar et al., "Expression analysis of biosynthetic pathway genes vis-a-vis podophyllotoxin content in Podophyllum hexandrum Royle", Protoplasma, vol. 252, No. 5, Sep. 2015, pp. 1253-1262.

Lata et al., "The Role of Biotechnology in the Production of the Anticancer Compound Podophyllotoxin", Springer, Chapter 31 of Protocols for In Vitro Cultures and Secondary Metabolite Analysis of Aromatic and Medicinal Plants, 2009, pp. 387-402.

Lauvergeat et al., "Two cinnamoyl-CoA reductase (CCR) genes from *Arabidopsis thaliana* are differentially expressed during development and in response to infection with pathogenic bacteria", Phytochemistry, vol. 57, No. 7, Aug. 2001, pp. 1187-1195.

Li et al., "Cd-hit: a fast program for clustering and comparing large sets of protein or nucleotide sequences", Bioinformatics, vol. 22, No. 13, May 26, 2006, pp. 1658-1659.

Malik et al., "Biotechnological approaches for producing aryltetralin lignans from *Linum* species", Phytochemistry Reviews, vol. 13, No. 4, Dec. 2014, pp. 893-913.

Mizutani et al., "Isolation of a cDNA and a Genomic Clone Encoding Cinnamate 4-Hydroxylase from *Arabidopsis* and Its Expression Manner in Planta", Plant Physiology, vol. 11, No. 3, Mar. 1997, pp. 755-763.

Nag et al., "Estimation of nuclear genome size of important medicinal plant species from western Himalaya using flow cytometry", Journal of Cell & Plant Sciences, vol. 2, No. 2, Apr. 16, 2011, pp. 19-23.

Paddon et al., "High-level semi-synthetic production of the potent antimalarial artemisinin", Nature, vol. 496, Apr. 25, 2013, pp. 528-532.

Pompon et al., "Yeast Expression of Animal and Plant P450s in Optimized Redox Environments", Methods in Enzymology, vol. 272, 1996, pp. 51-64.

Qu et al., "Completion of the seven-step pathway from tabersonine to the anticancer drug precursor vindoline and its assembly in yeast", Proceedings of the National Academy of Sciences of the United States of America, vol. 112, No. 19, May 12, 2015, pp. 6224-6229.

Rajesh et al., "Agrobacterium-mediated transformation of the medicinal plant Podophyllum hexandrum Royle (syn. P. emodi Wall. ex Hook.f. & Thomas)", Plant Cell, Tissue and Organ Culture, vol. 114, No. 1, Jul. 2013, pp. 71-82.

Roberts et al., "Streaming fragment assignment for real-time analysis of sequencing experiments", Nature Methods, vol. 10, No. 1, Nov. 18, 2012, pp. 71-73.

Robinson et al., "edgeR: a Bioconductor package for differential expression analysis of digital gene expression data", Bioinformatics, vol. 26, No. 1, Jan. 1, 2010, pp. 139-140.

Sainsbury et al., "pEAQ: versatile expression vectors for easy and quick transient expression of heterologous proteins in plants", Plant Biotechnology Journal, vol. 7, No. 7, Sep. 2009, pp. 682-693.

Schmittgen et al., "Analyzing real-time PCR data by the comparative CT method", Nature Protocols, vol. 3, Jun. 5, 2008, pp. 1101-1108.

Schoch et al., "CYP98A3 from *Arabidopsis thaliana* is a 3'-Hydroxylase of Phenolic Esters, a Missing Link in the Phenylpropanoid Pathway", Journal of Biological Chemistry, vol. 276, No. 39, Sep. 28, 2001, pp. 36566-36574.

Schulz et al., "Oases: robust de novo RNA-seq assembly across the dynamic range of expression levels", Bioinformatics, vol. 28, No. 8, Apr. 15, 2012, pp. 1086-1092.

Sibout et al., "Expression Pattern of Two Paralogs Encoding Cinnamyl Alcohol Dehydrogenases in *Arabidopsis*. Isolation and Characterization of the Corresponding Mutants", Plant Physiology, vol. 132, Jun. 2003, pp. 848-860.

Smith et al., "XCMS: Processing Mass Spectrometry Data for Metabolite Profiling Using Nonlinear Peak Alignment, Matching, and Identification", Analytical Chemistry, vol. 78, No. 3, Feb. 1, 2006, pp. 779-787.

Stahelin et al., "The Chemical and Biological Route from Podophyllotoxin Glucoside to Etoposide: Ninth Cain Memorial Award Lecture", Cancer Research, vol. 51, No. 1, Jan. 1991, pp. 5-15.

Teoh et al., "Molecular cloning of an aldehyde dehydrogenase implicated in artemisinin biosynthesis in Artemisia annua", Botany, vol. 87, No. 6, Jun. 22, 2009, pp. 635-642.

(56) References Cited

OTHER PUBLICATIONS

Thodey et al., "A microbial biomanufacturing platform for natural and semisynthetic opioids", Nature Chemical Biology, vol. 10, Aug. 24, 2014, pp. 837-844.

Umezawa et al., "Formation of lignans (−)-secoisolariciresinol and (−)-matairesinol with Forsythia intermedia cell-free extracts", Journal of Biological Chemistry, vol. 266, No. 16, Jun. 5, 1991, pp. 10210-10217.

Wankhede et al., "Expressed sequence tags and molecular cloning and characterization of gene encoding pinoresinol/ lariciresinol reductase from Podophyllum hexandrum", Protoplasma, vol. 250, No. 6, Dec. 2013, pp. 1239-1249.

Wanner et al. "The phenylalanine ammonia-lyase gene family in *Arabidopsis thaliana*", Plant Molecular Biology, vol. 27, No. 2, Jan. 1995, pp. 327-338.

Wils et al., "A single amino acid determines position specificity of an *Arabidopsis thaliana* CCoAOMT-like O-methyltransferase", FEBS Letters, vol. 587, No. 6, Mar. 18, 2013, pp. 683-689.

Xia et al., "Secoisolariciresinol Dehydrogenase Purification, Cloning, and Functional Expression", Journal of Biological Chemistry, vol. 276, No. 16, Apr. 20, 2001, pp. 12614-12623.

\* cited by examiner

Figure 2
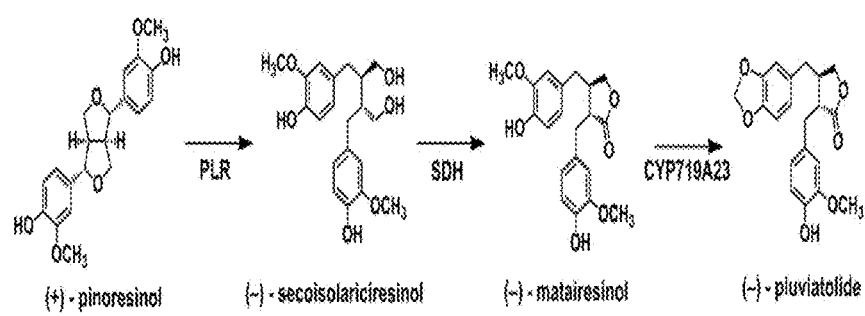
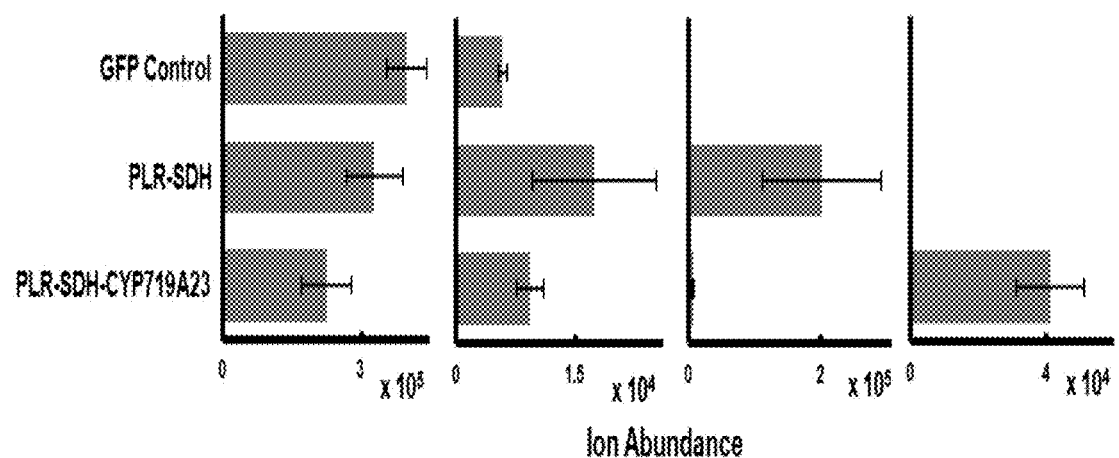

Figure 6

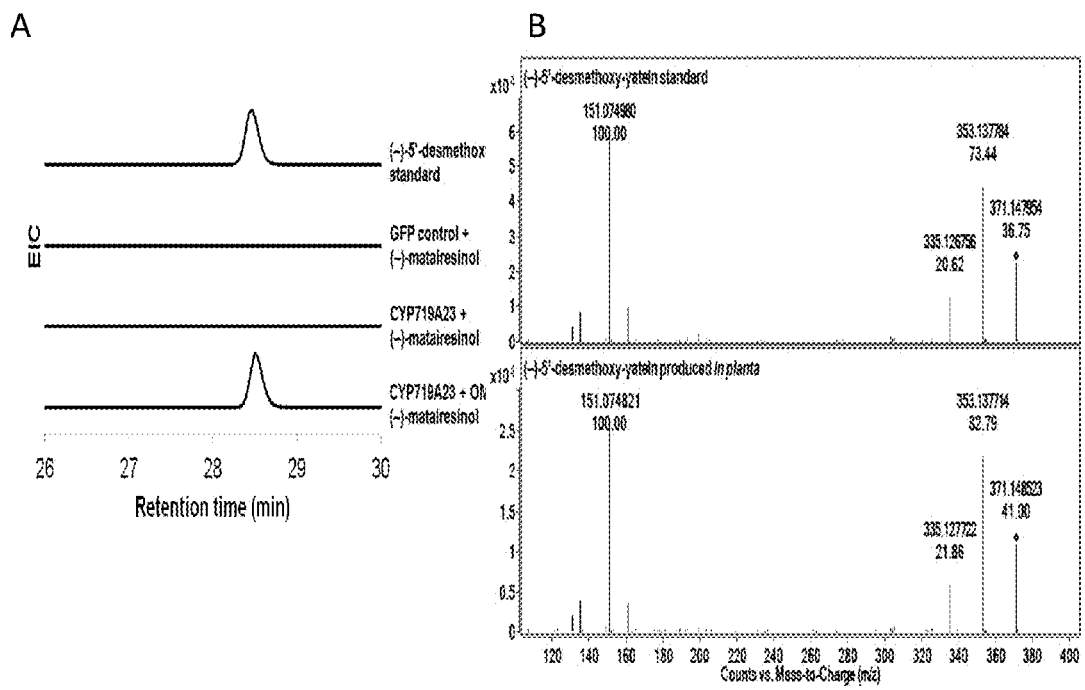

| m/z (observed) | Predicted formula | Ion assignment | m/z (theoretical) | Δm/z (ppm) |
|---|---|---|---|---|
| 371.1480 | $C_{21}H_{23}O_6^+$ | A, $[M+H]^+$ | 371.1489 | 2.55 |
| 353.1378 | $C_{21}H_{21}O_5^+$ | B, $[M+H-H_2O]^+$ | 353.1384 | 1.74 |
| 335.1268 | $C_{21}H_{19}O_4^+$ | $[M+H-2H_2O]^+$ | 335.1283 | 4.61 |
| 161.0590 | $C_{10}H_9O_2^+$ | C | 161.0597 | 4.60 |
| 151.0750 | $C_9H_{11}O_2^+$ | D | 151.0754 | 2.78 |
| 135.0433 | $C_8H_7O_2^+$ | E | 135.0441 | 6.15 |
| 131.0492 | $C_9H_7O^+$ | | 131.0497 | 3.85 |

D

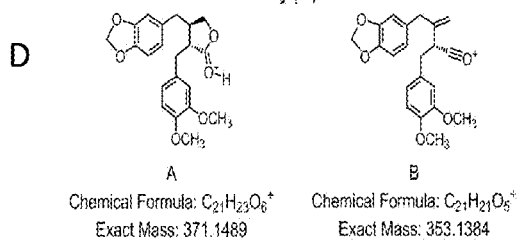

A
Chemical Formula: $C_{21}H_{23}O_6^+$
Exact Mass: 371.1489

B
Chemical Formula: $C_{21}H_{21}O_5^+$
Exact Mass: 353.1384

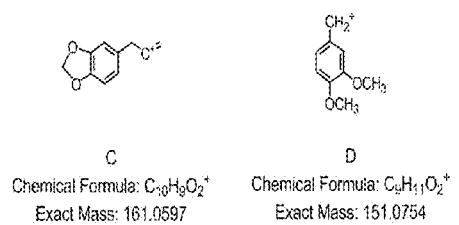

C
Chemical Formula: $C_{10}H_9O_2^+$
Exact Mass: 161.0597

D
Chemical Formula: $C_9H_{11}O_2^+$
Exact Mass: 151.0754

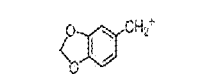

E
Chemical Formula: $C_8H_7O_2^+$
Exact Mass: 135.0441

Figure 8
A
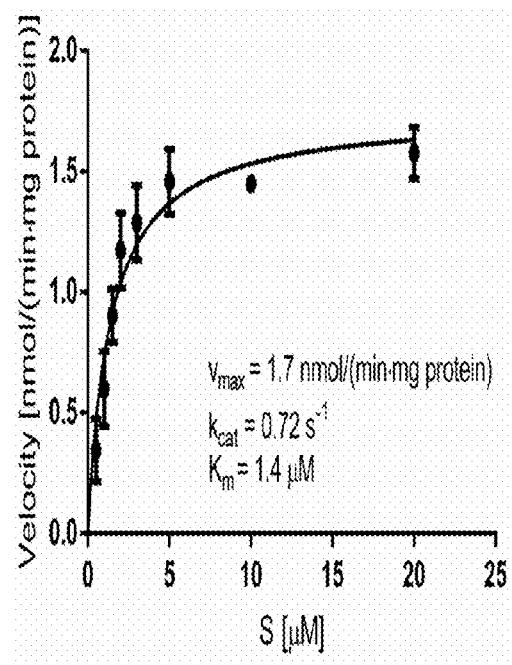
B
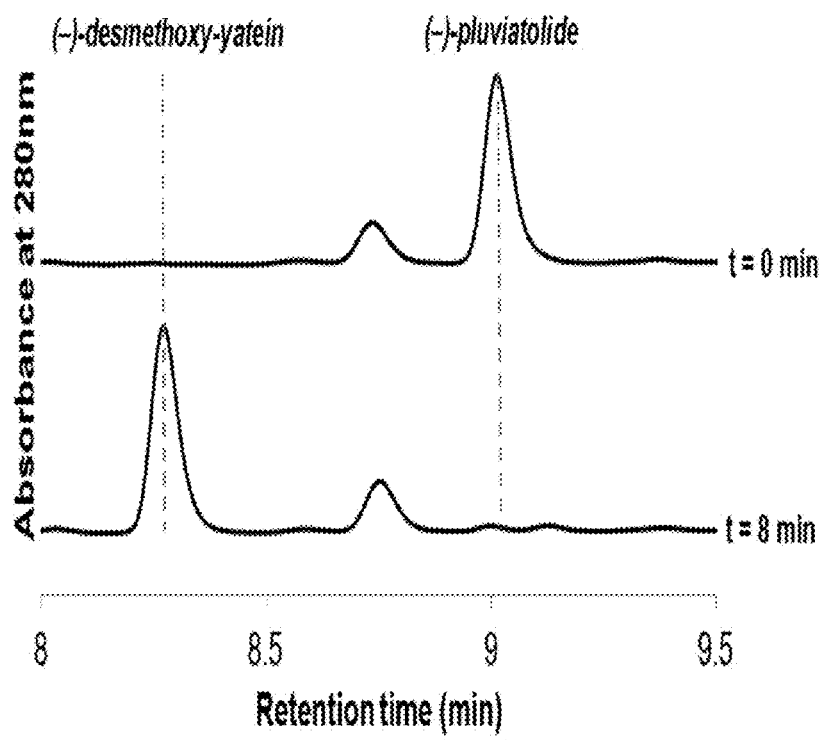

Figure 14
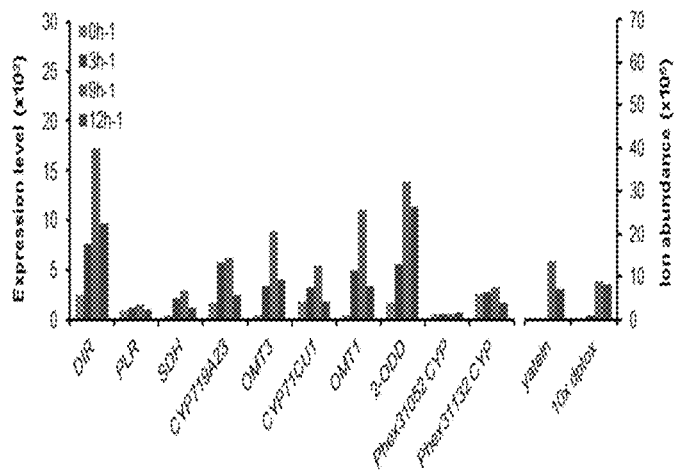
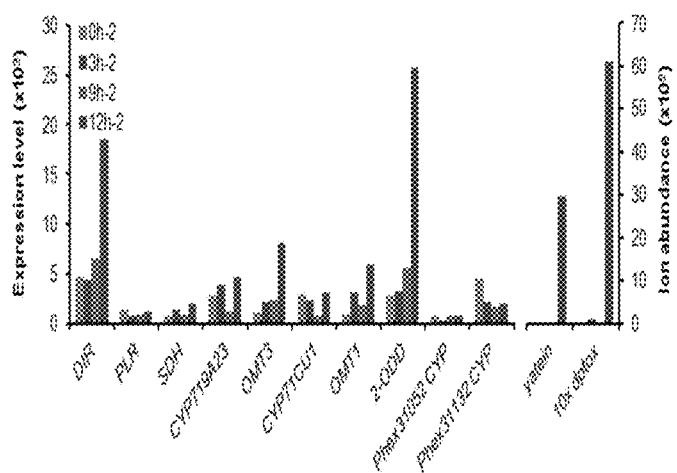
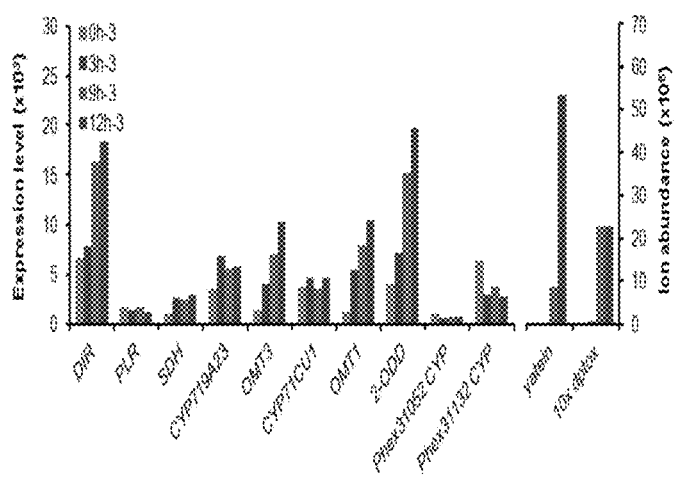

Figure 19
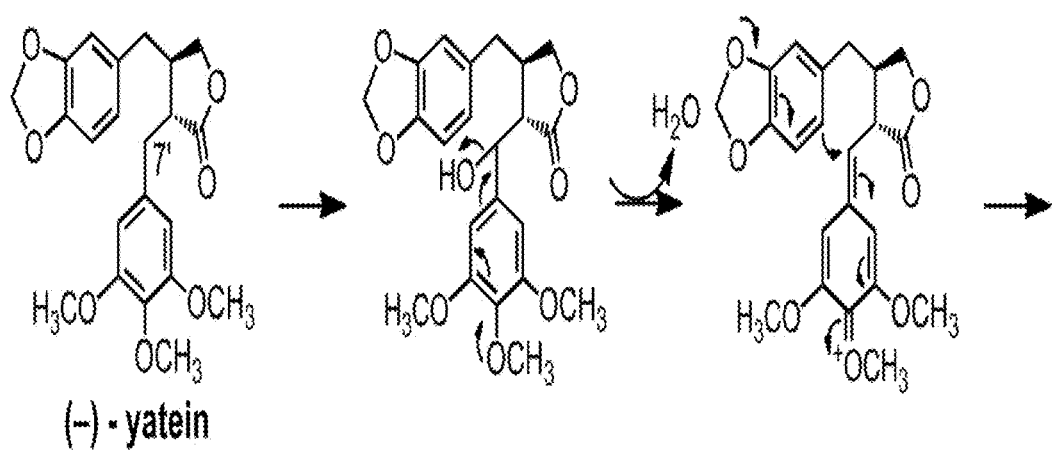
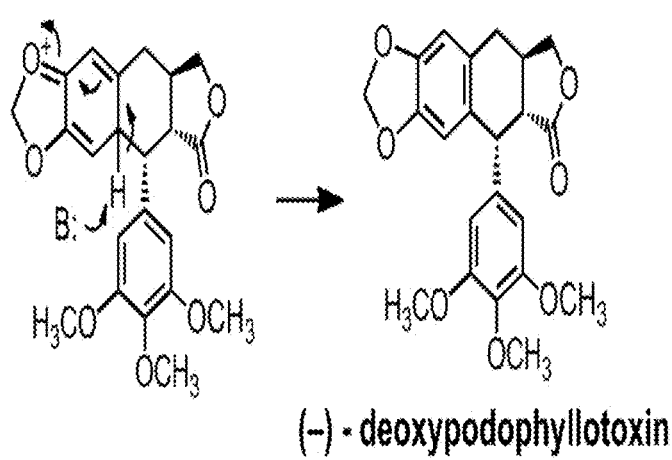

Figure 20
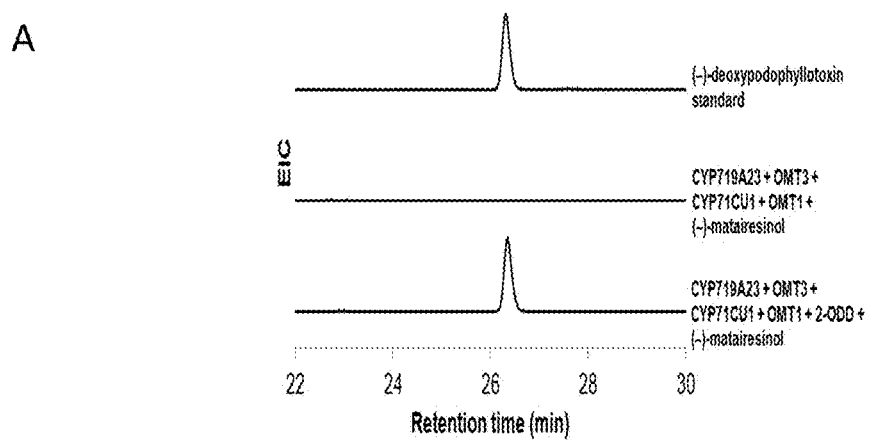
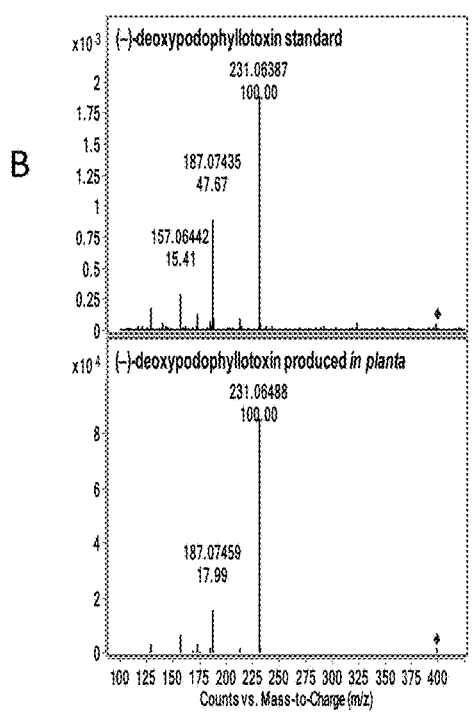
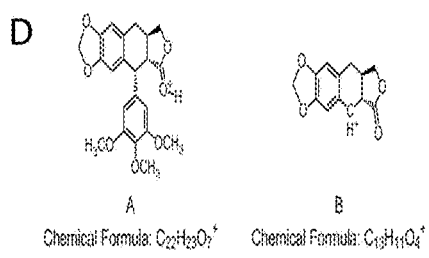
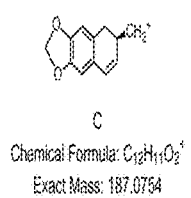

Figure 21
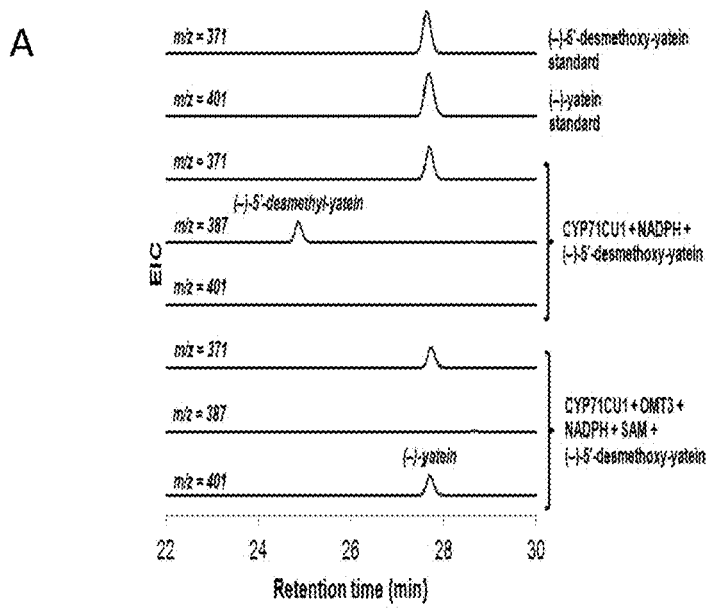
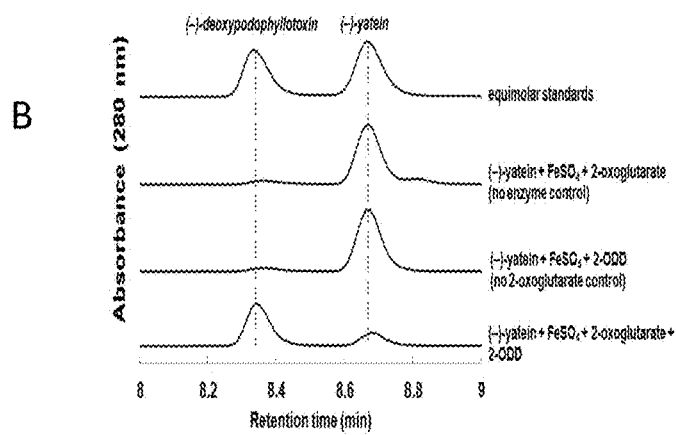
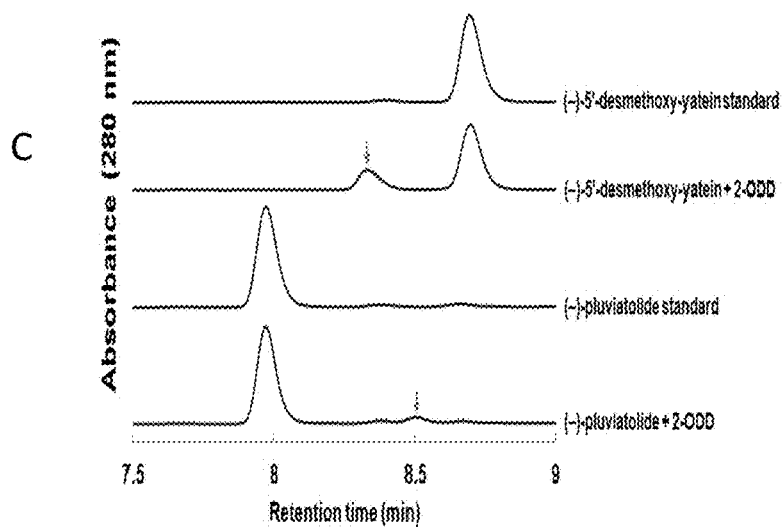

Figure 23

| Contig | Gene | Best blastx hit as of March 2015 | % Identity |
|---|---|---|---|
| 38407 | CYP82D61 | CYP82D61 [Sinopodophyllum hexandrum] | 99 |
| 14272 | CYP716E54_1 | PREDICTED: premnaspirodiene oxygenase-like isoform X1 [Solanum tuberosum] | 59 |
| 8371 | CYP716E54_2 | | |
| 22113 | CYP716E54_3 | | |
| 2475 | CYP716E54_4 | | |
| 5041 | CYP | PREDICTED: cytochrome P450 CYP736A12-like [Pyrus x bretschneideri] | 52 |
| 57270 | CYP | CYP716E30 [Sinopodophyllum hexandrum] | 100 |
| 28054 | CYP | PREDICTED: geraniol 8-hydroxylase-like [Nelumbo nucifera] | 68 |
| 4618 | CYP | PREDICTED: cytochrome P450 CYP736A12-like [Malus domestica] | 52 |
| 58321 | NADP | PREDICTED: cinnamoyl-CoA reductase 2-like [Elaeis guineensis] | 58 |
| 1888 | NADP | RecName: Full=Non-functional NADPH-dependent codeinone reductase 2 [Papaver somniferum] | 63 |
| 102408 | CYP719A23 | | |
| 6901 | PLR | | |
| 17736 | CYP719A23 | | |
| 26599 | SDH | | |
| 225796 | CYP719A23 | | |
| 212985 | CYP719A23 | | |
| 140193 | PLR | | |
| 8051 | DIR | | |
| 31365 | CYP719A23 | | |
| 38318 | CYP719A23 | | |
| 12248 | SDH | | |
| 34018 | CYP719A23 | | |
| 12826 | SDH | | |
| 145347 | CYP719A23 | | |
| 193171 | CYP719A23 | | |

Figure 30
A
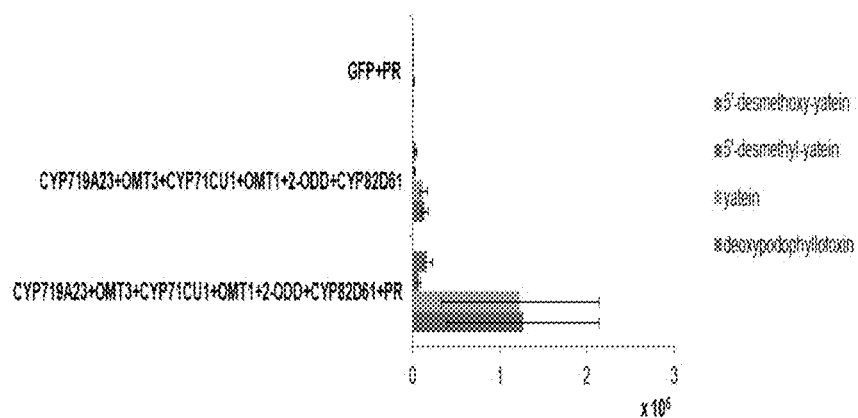
B
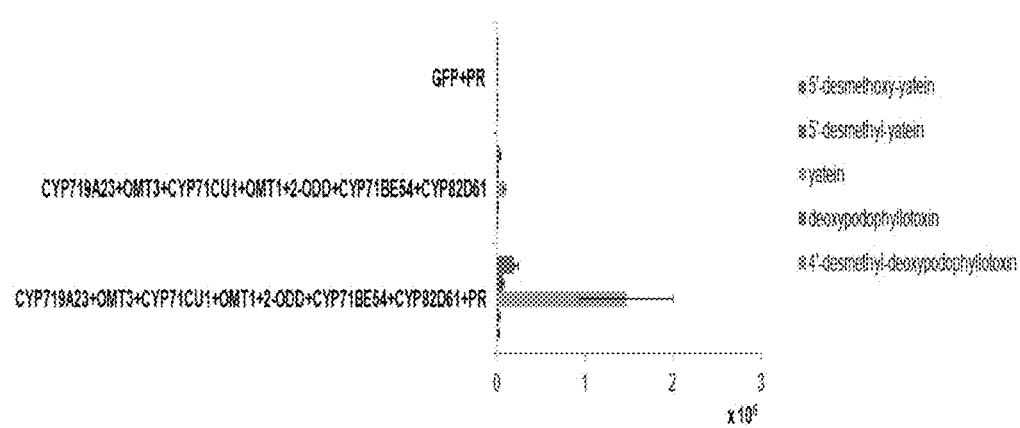

Figure 33

| Carbon No. | 1H δ (ppm) [m, J_HH (Hz), area] in CDCl_3 | Published 1H δ (ppm) [m, J_HH (Hz), area] in CDCl_3 |
|---|---|---|
| 2, 3, 5, 6' | 6.50 (dd, J = 8.0, 1.9 Hz, 1H), 6.58 – 6.60 (m, 1H), 6.79 (d, J = 7.8 Hz, 1H), 6.81 (d, J = 8.0 Hz, 1H) | 6.51 (d, J = 7.8 Hz, 1H), 6.60 (d, J = 7.3 Hz, 1H), 6.80 (d, J = 8.3 Hz, 1H), 6.82 (d, J = 7.8 Hz, 1H), |
| 4-OH, 4'-OH | 5.57 (s, 1H), 5.59 (s, 1H) | 5.49 (s, 1H), 5.52 (s, 1H) |
| 5-OCH_3, 3'-OCH_3 | 3.80 (s, 3H), 3.81 (s, 3H) | 3.81 (s, 3H), 3.82 (s, 3H) |
| 6, 2' | 6.40 (d, J = 1.9 Hz, 1H), 6.61 (s, 1H) | 6.41 (s, 1H), 6.61 (s, 1H) |
| 7, 8, 8' | 2.41-2.64 (m, 4H) | 2.42 - 2.64 (m, 4H) |
| 7' | 2.87 (dd, 1H, 14, 7 Hz), 2.95 (dd, J = 14, 5 Hz) | 2.88 (dd, 1H, J = 14.2, 6.8 Hz), 2.95 (dd, 1H, J = 14.2, 5.9 Hz) |
| 9 | 3.88 (dd, 1H, J = 9, 7 Hz), 4.09-4.18 (m, 1H) | 3.89 (dd, 1H, J = 6.8, 6.8 Hz), 4.15 (dd, 1H, J = 9.3, 7.8 Hz) | arctigenin

| Carbon No. | 1H δ (ppm) [m, J_HH (Hz), area] in CDCl₃ | Published 1H δ (ppm) [m, J_HH (Hz), area] in CDCl₃ |
|---|---|---|
| 2, 3, 6, 2', 5', 6' | 6.45 (d, J = 2.1 Hz, 1H), 6.54 (dd, J = 8.1, 2.1 Hz, 1H), 6.56 – 6.64 (m, 2H), 6.74 (d, J = 8.1 Hz, 1H), 6.81 (d, J = 7.9 Hz, 1H) | 6.48 (d, J = 2.0 Hz, 1H), 6.55 (dd, J = 7.8, 2.0 Hz, 1H), 6.61 (d, J = 7.8, 2.0 Hz, 1H), 6.64 (d, J = 2.0 Hz, 1H), 6.75 (d, J = 7.8 Hz, 1H), 6.82 (d, J = 7.8 Hz, 1H) |
| 4-OH | 5.60 (s, 1H) | 5.55 (s, 1H) |
| 5-OCH₃, 4'-OCH₃, 3'-OCH₃ | 3.80 (s, 6H), 3.84 (s, 3H) | 3.81 (s, 6H), 3.85 (s, 3H) |
| 7, 8, 8' | 2.40 – 2.66 (m, 4H) | 2.43 – 2.67 (m, 4H) |
| 7' | 2.89 (dd, J = 14.1, 6.6 Hz, 1H), 2.94 (dd, J = 14.1, 5.3 Hz, 3H) | 2.85 – 3.00 (m, 2H) |
| 9 | 3.86 (dd, J = 9.6, 1.6 Hz, 1H), 4.06 – 4.17 (m, 1H) | 3.88 (dd, J = 8.8, 7.3 Hz, 1H), 4.13 (dd, J = 8.8, 6.8 Hz, 1H) | pluviatolide

| Carbon No. | 1H δ (ppm) [m, J_HH (Hz), area] in CDCl_3 | Published 1H δ (ppm) [m, J_HH (Hz), area] in CDCl_3 |
|---|---|---|
| 2, 3, 6, 2', 5', 6' | 6.41 – 6.48 (m, 2H), 6.58 – 6.71 (m, 3H), 6.83 (d, J = 8.0 Hz, 1H) | 6.44-6.47 (m, 2H), 6.63 (dd, J=1.8, 7.9 Hz, 1H), 6.67 (J = 1.8 Hz, d, 1H), 6.69 (d, J=7.7 Hz, 1H), 6.84 (d, J=8 Hz, 1H) |
| 4, 5 O-CH_2-O | 5.92 (s, 2H) | 5.93 (d, J=1.4 Hz, 1H), 5.94 (d, J=1.4 Hz, 1H) |
| 3'-OCH_3 | 3.84 (s, 3H) | 3.85 (s, 3H) |
| 7, 8, 8' | 2.39 – 2.65 (m, 4H) | 2.45 - 2.62 (m, 4H) |
| 7' | 2.88 (dd, J = 14.1, 6.8 Hz, 1H), 2.85 (dd, J = 14.0, 5.0 Hz, 1H) | 2.89 (dd, J=7.0, 14.1 Hz, 1H), 2.96 (dd, J=5.2, 14.0 Hz, 1H) |
| 9 | 3.85 – 3.91 (m, 1H), 4.06 – 4.15 (m, 1H) | 3.86 (dd, J=7.4, 9.1 Hz, 1H), 4.11 (dd, J=7.1, 9.2 Hz, 1H) |

Figure 34D
5'-desmethoxy-yatein
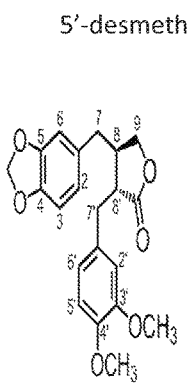
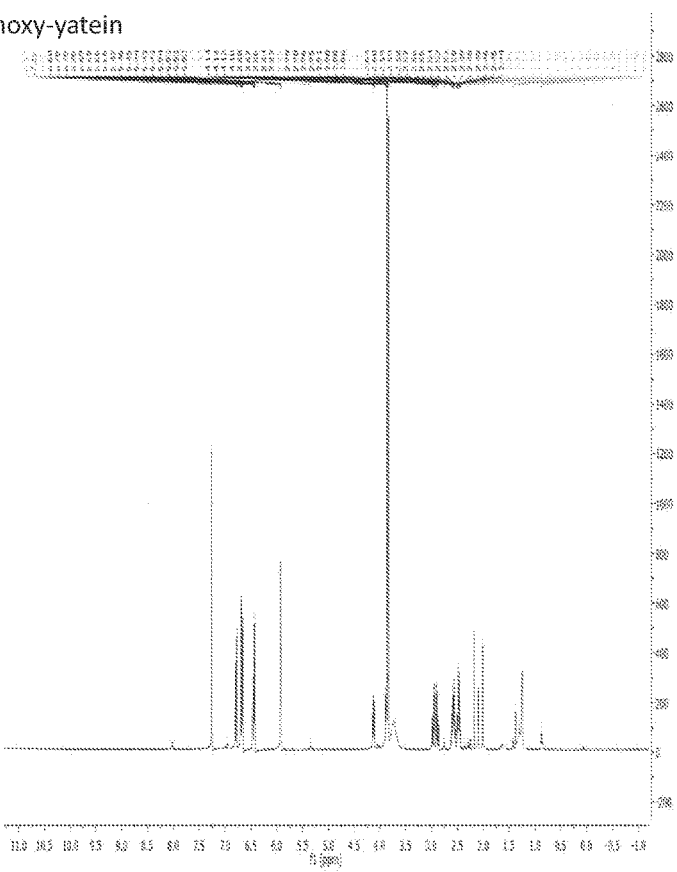
| Carbon No. | 1H δ (ppm) [m, J$_{HH}$ (Hz), area] in CDCl$_3$ | Published 1H δ (ppm) [m, J$_{HH}$ (Hz), area] in CDCl$_3$ |
|---|---|---|
| 2, 3, 6, 2', 5', 6' | 6.42 – 6.48 (m, 2H), 6.63 – 6.71 (m, 3H), 6.76 – 6.81 (m, 1H) | 6.41-6.45 (m, 2H) 6.64-6.68 (m, 3H), 6.77 (d, J = 8.0, 1H) |
| 4, 5 O-CH$_2$-O | 5.92 (d, J = 1.5 Hz, 1H), 5.93 (d, J = 1.4 Hz, 1H) | 5.90-5.91 (m, 2H) |
| 3'-OCH$_3$, 4'-OCH$_3$ | 3.83 (s, 3H), 3.86 (s, 3H) | 3.82 (s, 3H), 3.84 (s, 3H) |
| 7, 8, 8' | 2.39 – 2.65 (m, 4H) | 2.44-2.58 (m, 4H) |
| 7' | 2.89 (dd, J = 14.1, 7.0 Hz, 1H), 2.97 (dd, J = 14.1, 5.1 Hz, 1H) | 2.87 (dd, J = 7.1, 14.2, 1H), 2.95 (dd, J = 5.1, 14.0, 1H) |
| 9 | 3.87 – 3.89 (m, 1H), 4.12 (dd, J = 9.1, 6.7 Hz, 1H) | 3.84 (m, 1H), 4.10 (dd, J = 6.8, 9.0 Hz, 1H) |

Figure 34E
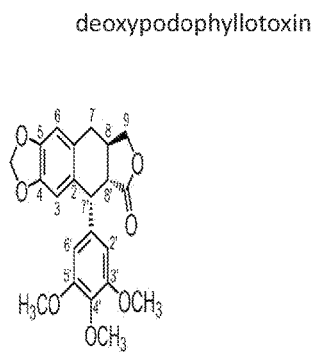
deoxypodophyllotoxin
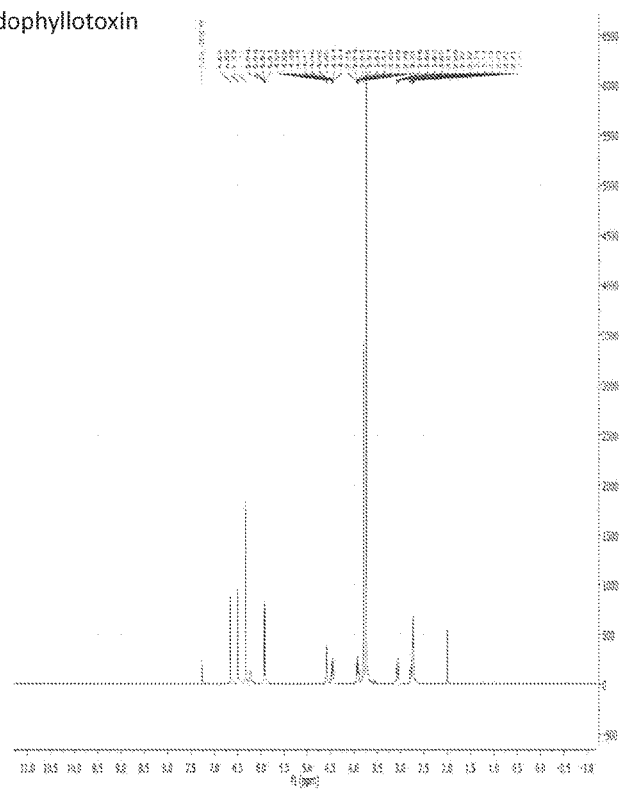
| Carbon No. | 1H δ (ppm) [m, $J_{HH}$ (Hz), area] in $CDCl_3$ | Published 1H δ (ppm) [m, $J_{HH}$ (Hz), area] in $CDCl_3$ |
|---|---|---|
| 3, 6, 2', 6' | 6.33 (s, 2H), 6.50 (s, 1H), 6.66 (s, 1H) | 6.34 (s, 2H), 6.52 (s, 1H), 6.67 (s, 1H) |
| 4, 5 O-$CH_2$-O | 5.92 (d, J = 1.3 Hz, 1H), 5.94 (d, J = 1.4 Hz, 2H) | 5.93 (d, J = 1.0 Hz, 1H), 5.95 (d, J = 1.0 Hz, 1H) |
| 3'-$OCH_3$, 4'-$OCH_3$, 5'-$OCH_3$ | 3.73 (s, 6H), 3.79 (s, 3H) | 3.75 (s, 6H), 3.80 (s, 3H) |
| 7, 8, 8' | 2.69 – 2.82 (m, 3H), 3.01 – 3.12 (m, 1H) | 2.74 (m, 2H), 2.77 (m, 1H), 3.08 (d, J = 11.2 Hz, 1H) |
| 7' | 4.58 (d, J = 3.2 Hz, 1H) | 4.60 (d, J = 2.8 Hz, 1H) |
| 9 | 3.85 – 3.97 (m, 1H), 4.41 – 4.51 (m, 1H) | 3.91 (td, 1H), 4.45 (td, 1H) |

| Carbon No. | 1H δ (ppm) [m, J_HH (Hz), area] in CDCl_3 | Published 1H δ (ppm) [m, J_HH (Hz), area] in CDCl_3 |
|---|---|---|
| 3, 6, 2', 6' | 6.27 (s, 2H), 6.54 (s, 1H), 6.88 (s, 1H) | 6.28 (s, 2H), 6.56 (s, 1H), 6.88 (s, 1H) |
| 4, 5 O-CH_2-O | 5.97 (d, J = 1.3 Hz, 1H), 6.00 (d, J = 1.3 Hz, 1H) | 5.98 (d, J = 1.3 Hz, 1H), 6.00 (d, J = 1.3 Hz, 1H) |
| 3'-OCH_3, 4'-OCH_3, 5'-OCH_3 | 3.73 (s, 6H), 3.79 (s, 3H) | 3.74 (s, 6H), 3.80 (s, 3H) |
| 8, 8' | 2.76 – 2.90 (m, 1H), 3.28 (dd, J = 14.1, 5.2 Hz, 1H) | 2.84 (dddd, J = 14.1, 10.6, 7.9, 3.4 Hz, 1H), 3.29 (dd, J = 14.1, 5.1 Hz, 1H) |
| 7, 7' | 4.61 (d, J = 5.2 Hz, 1H), 4.87 (d, J = 3.4 Hz, 1H) | 4.62 (d, J = 5.1 Hz, 1H), 4.88 (dd, J = 4.3, 3.4 Hz, 1H) |
| 9 | 4.31 – 4.43 (m, 2H) | 4.36 (dd, J = 10.6, 8.5 Hz, 1H), 4.39 (dd, J = 8.5, 7.9, 1H) |

4'-desmethyl-epipodophyllotoxin

| Carbon No. | 1H δ (ppm) [m, J_HH (Hz), area] in CDCl₃ | Published 1H δ (ppm) [m, J_HH (Hz), area] in CDCl₃ |
|---|---|---|
| 3, 6, 2', 6' | 6.27 (s, 2H), 6.53 (s, 1H), 6.85 (s, 1H) | 6.22 (s, 2H), 6.48 (s, 1H), 6.81 (s, 1H) |
| 4, 5 O-CH₂-O | 5.95 (d, J = 1.7 Hz, 1H), 5.98 (d, J = 1.7 Hz, 4H) | 5.92 (dd, J = 8.8, 1.3 Hz, 2H) |
| -OH | 5.38 (s, 1H) | 5.35 (s, 1H) |
| 3'-OCH₃, 5'-OCH₃ | 3.75 (s, 6H) | 3.70 (s, 6H) |
| 8, 8' | 2.73 – 2.86 (m, 1H), 3.25 (dd, J = 14.2, 5.1 Hz, 1H) | 2.75 (dddd, J = 14.1, 6.3, 3.8, 3.5 Hz, 1H), 3.19 (dd, J = 14.1, 5.1 Hz, 1H) |
| 7, 7' | 4.59 (d, J = 5.0 Hz, 1H), 4.82 – 4.87 (m, 1H) | 4.54 (d, J = 5.1 Hz, 1H), 4.79 (d, J = 3.5 Hz, 1H) |
| 9 | 4.30 – 4.41 (m, 2H) | 4.27 (d, J = 3.8 Hz, 1H), 4.31 (d, J = 6.3 Hz, 1H) |

Figure 35

OMT3
MEMAPTMDLEIRNGNGYGDSGEELLAAQAHIYNHIFNFISSMALKCAVELNI
PEILHNHQPKAVTLSELVQALQIPQAKSACLYRLLRILVHSGFFAITKIQSEGDE
EGYLPTLSSKLLLKNHPMSMSPCLLGLVNPTMVAPMHFFSDWFKRSDDMTP
FEATHGASLWKYFGETPHMAEIFNEAMGCETRLAMSVVLKECKGKLEGISSL
VDVGGGTGNVGRAIAEAFPNVKCTVLDLPQVVGNLKGSNNLEFVSGDMFQ
FIPPADVVFLKWILHDWNDEECIKILKRCKEAIPSKEEGGKLIIIDMVVNDHNK
GSYESTETQLFYDLTLMALLTGTERTETEWKKLFVAAGFTSYIISPVLGLKSIIEV
FP

CYP71CU1
METFQCLTLFLLFISTVFILKRKFSHKPNLPPSPPKLPILGNFHQLGTLVHRAVTV
LAAKYGPLMLLHFGKTPVLIVSSQETAKEIMKTHDLALANRPLTTAARALLYDC
TDISFAPYGEYWREMKKMAVLNLLSIKKIQSFRSVREELASDMIKEITRLSKTG
APVDVTNMLYHFSEDLLFRCTLGFKPKGQHKFQKLSRDFLDLVGAFCFNDFFP
GMAWMDALTGLNRKLKKGSRELDDFVDELIEERIAMVKDGVEPNEFLDLLL
HTHRDTTQEIKLTRDNVKAIILDTFLGGIDLPASVMEWAMAELMRNPSKMKI
AQEEVRKVVGNKNKVDEDDVYQMNFLKSAVKETLRLHPPAPLLFARESYTSI
NVENYIIPPYTSVMINIWHIQRDPKLWDKAEEFIPERFMNSGIDYKSHDYEFIP
FGSGRRGCPGMSFGVAAVEFAVANLLYWFDWKFVGDTTPETLDMTEDYCF
ALFKKKPLHFIPISRSS

OMT1
MDTRADAEIKAMELIGIGVLPLAMKAIIELNVLEILSKAGPDTQLTAAQIVTDIP
TTNPNAGFQLDRILRLLASHSVLSSSITKSGERVYGLTPMCKYFLPDQDGVSLA
PMVVTIHDKVLLQSWHYLKDSVLKQGSLPFTEAFGMSPFEYSVSDTRFNKVF
NAGMFDHSTLCMRDVLQRYKGFQGLGELVDVGGGTGGSLKMILSQYPNLK
GINFDLPHVVADAPSFPGVKHIGGDMFESVPSGDAIFMKWILHDWDDGRCL
TLLKNCWNALPEHGKVIIVEWILPSDAATDPTSRRVFTADLMMLAFSEGGKE
RTLGDYGALAKEAGFTTVKDFPCANGISVIEFHKK

Figure 36

2-ODD
MGSTAPLRLPVIDLSMKNLKPGTTSWNSVRTQVREALEEYGCFEAVIDA
VSPELQKAVCNKGHELLNLPLETKMLNGNKPEYDGFTSIPNLNEGMGVG
RITDLEKVERFTNLMWPEGNKDFCETVYSYGKRMAEVDHILKMMVFESF
GMEKHFDSFCESTNYLLHFMRYQQPGKDGRSPALSLHKDKSILTIVNQN
DVKGLEFETKDGEWILPTADNHIVLLGDCFMAWSNGRLHSPLHRVTLVA
NQARLSTSSFSFPKDIIETPAELVDEEHPLLFNPFEITELLAYCFTKEGAKAV
CDLKQYKAYTGA

CYP71CE54
MEFLSFPLSSALLIILLFMLVKKAIQNKNSKLPPGPRKLPVIGSLHHLIGDGL
PHHALRNLAKKHGPLMHLQLGENSTLVVSSSKMARAIMSTHDLMFANR
TVQFATDILLYGGKGIGLAPYGDYWRQIRKICVLELLSAKRVQSFQTVREE
EISNLIRSISAESSKVNFSEMITSLTNDIIARAAFGEKCKDKHAFLSLIEEGIQL
AGGFDIAGLFPSLKLLHVITGKKRQLERVHNELDRILVDIIKENKEKRRASKL
NEDKYEENLVDVLVRVQENTQLEVPLANDNLKAVILDIFVAGSETSSTTIE
WAMSEMLKNPKVMKKAQAEVRRVFSGNKKINETEIQELSYLKLVLKETL
RLHAPAPLLIPRECRESCEIDGYEIPKKTMVMVNAWAIGRDPENWSNGD
RFEPERFDGISVDYKGTNFEYIPFGAGRRICPGMLFGMANVEVPLARLLY
HFDWELPNGIKPEELDMDETFGTTVRRKNHLYLIPTVVHELERSTTKE

CYP82D61
MDSLHCLETLLLGFFVLLPCFFYFVWKKPNNKIKEPPQPAGAWPIIGHLHL
LARGDLPHKILSSFADKNGPVFKIQLGVHQALVVNNSEIAKECFTTNDRFF
LNRPSGVAAKIMGYNYVMLGVAPYGPYWRDMRKIIMLEFLSNRRLQSLK
HVWHSEISISSKELYKLWETQNIDFCLVDMKQWLADLTLNMSVKMVVG
KRFFGSASASACEETESSNCPKTLRNMFRLMGSFVLSDYLP
YLRWLDLGGHEKEMKRTVKELDILFKGWLDEHKRKRLSGGKEDDDQDF
MDVMLSILEESKLGNDVDTINKTACLAIILGGADTTWATLTWALSLLLNN
PNALKKAQDELDLHVGRDRNVDESDLVKLTYIDAIIKETLRLYPPGPLLGPR
VVTEDCTIAGYHVRAGTRLIVNAWKIQRDPLVWSQPHEYQPERFLERDV
DMKGQHFELIPFGSGRRACPAISLALQVLPLTLAHILHGFELRTPNQNKVD
MTETPGIVHAKATPLEVLVAPRISPKCFV

Figure 37

```
ATGGCTAAGAGCAGAGTTCTCATTGTTGGGGGTACAGGGTACCTAGGAA
GGAGAATGGTAAAGGCTTGCTTAGACCAAGGTCACACTACATATGTTCTA
CATCGTCAAGAGATTGGCGTCGACATCGATAAGATCCAGATGCTATTGTC
GTTCAAGGAGCAAGGGGCACACCTTGTTGAGGGCTCATTCAATGATCATC
GCAGCCTTGTTGAGGCCGTGAAATTGGTTGATGTTGTTATATGTACTATTT
CTGGAGTACATATAAGGAGCCATCAGATATTGTTACAACTTAAGCTTGTT
GAAGCAATCAAGGAAGCTGGAAATGTAAAGCGATTCTTGCCATCGGAGT
TTGGTATGGATCCAGCACGGATGGCACATGCAATGGAACCTGGAAGGGC
AACATTTGACGAAAGATGGTGGTGAGAAGGCGATCGAAGATGCCAA
AATTCCTCATACTTATGTTTCAGCAAATTGTTTTGCTGGATACTTTTTGGG
GGGTCTGTGTCAATTCGGTAAGATCATACCCTCGAAGGAAAGTGTAATTT
TAAGCGGAGATGGCAATGTAAAAGGTATTTATGTGGATGAATACGATAT
TGCGACTTACACCATCAAGACCATGGATGATCCTCGTACGCTGAACAAAA
CGATCTATATTAGGCCTCCAGCGAACATTCTATCTCAAAGAGAGGTGGTA
GAAATTTGGGAGAAACTCATTGGGAAAGTGTTAGACAAGTCTTCCTTATC
AGAGGAGGACTTCCTGGCTCTCATGAAAGGTCTGAGTCATGGACATCAG
GCAGGATTGACACATTATTATCATGTTTCCTATGAGGGGTGCCTTACAAAT
TTTGAAGTAGAGGATGGAGTAGATGCTTCAAAGCTTTATCCAGAAGTGA
ATTACACTAAAGTGTCCGAATATCTCAAACGATATTTGTAG
```

Figure 38

ATGGGATCCACTTCTACACCAGCTTCGTCTACCAACAGGTTAC
AAGATAAAGTAGCCATCATAACAGGGGGAGCAGGTGGGATT
GGTGAAACCACAGCAAAATTATTCGTCCGCTACGGTGCTAAA
GTTGTGATAGCAGACATCTCAGATGACCACGGCCAAAAAGTT
TGTAACAACATTGGCTCACCGGACGTGATCTCTTTCGTTCATT
GTGATGTGACCAAAGATGAGGACGTCCGGAACCTAGTGGAT
ACCACCATAGCCAAGCATGGAAAACTTGACATAATGTTCGGC
AACGTTGGTGTTCTGAGCACCACTCCTTACAGCATACTGGAA
GCTGGAAATGAAGATTTCAAGAGAGTTATGGACATTAACGTG
TATGGTGCATTTTTAGTAGCCAAACACGCTGCCCGAGTCATGA
TCCCAGCGAAGAAAGGTAGTATAGTATTCACTGCAAGTATTT
CTTCCTTCACAGCAGGAGAAGGTGTGTCGCATGTTTACACTGC
AACCAAGCATGCTGTCCTTGGATTGACAACTAGCTTATGTACT
GAGCTAGGACAGCATGGGATCCGAGTGAACTGTGTATCTCCC
TATGTTGTTGCATCCCCATTGTTGACCGATGTGTTTGGAGTGG
ATTCTAGTAGGGTTGAGGAATTGGCACATCAAGCTGCAAACT
TGAAAGGGATTTTGCTCAGGGCTGAGGATGTGGCCGATGCA
GTCGCTTATTTGGCAGGGGATGAGTCCAAGTATGTGAGCGGC
CTGAACCTTGTTATCGATGGGGGCTACACCAGAACCAATCCA
GCTTTCCCAACCGCATTGAAACATGGATTGGCTTGA

Figure 39

ATGGAGATGGAGATGAGTGTCTTGGCTATGAGCTCCACTTTGATATT
AGCCTTGGCTATGGCACTGATATTCTTATTCAAAGCAAAGTCGTCTTC
TGCAATTAAATGGCCTCCAGGGCCAAAAACATTACCCATCATCGGTA
ATCTCCACCAACTAGGAGGTGATGAGCTGCACATTGTTCTCGCTAAG
CTTGCTAGAGTTCACGGTGCTATCATGACCATCTGGATGGCAAAGAA
ACCAGTGATTGTTGTCAGCGATGTGAACTCAGTTTGGGAGGTGCTTG
TGAGCAAGTCCTCTGACTATGCTGCTCGCGATGCGGCTGAAATTTCCA
AAATAGTCTCTGCCAGCTCTCACTCTATCAACACATCGGACTCAGGCC
CTTATTGGCAGACTCTTCGTAGGGGACTTACGCATGGTCCTTTAGGG
CCGCTCAACATATCAGCGCAAATCCCGATCCAGCAGAGGGACATGCA
AAGAGTCATTCGAGAGATGCAACAAGATGCTGCTGCAAACGGGGGA
ATCATTAAGCCACTCGACCATCTTAAAAGATCTTCCACAAGATTAGTG
AGTCGACTCATCTTTGGAGACACCTTTGACAATGACCCTTATAATGAT
TCGATGCACGAAGTAGTCCAAGATCTAAATCGGTTCGGTGGTATAGC
TCTACTTGAACAAGCATTCTCATTTGCTAAACACCTCCCTAGTTACAAG
CGTGGCGTCAAAGAATTCCACATACACAAAAGGAAAATCGATGACTT
GGTAAGACCTGTCGTAGCATCTGCAAATCCTCCCAGTAATAGTTACCT
AGGCTTTCTTCAATCTCAAAACTATTCAGAAGAGATTATCATAGCTTG
CATCTTTGAATTGTACCTTTTGGCTATGGACAGTTCTGCATCTACAGCT
ACATGGGCTCTAGCTTTCATGATACGCGACCAACAAGTTCAGGAAAA
GCTCTATCAAGATATCAAACGTGTTATCGGTGATGGGGTAGACCTTG
TGAAAGCAGAAGATTTAAGTAAGATGCATTATTTACAAGCAGTGGTG
AAAGAGACTATGAGGATGAAGCCAATAGCACCTCTGGCAATTCCTCA
CAAGACTGCTATTGACACCACCGTGATGGGGACTAAGGTGCCTAAGG
GAACCTGTGTAATGGTCAATCTTTACGCTTTACATCATGACGAAAGCG
TCTGGGCCAAACCGTATACATTTATGCCAGAGAGGTTCTTGCAAGGC
GAAGACGGTAAAAGCGTTACAGAGCAAGCATTTCTACCATTTGGTGC
TGGTATGAGAATCTGTGGAGGAATGGAGGTGGGGAAGCTCCAGTTT
TCTTTGGCACTCGCGAATTTAGTGAATGCGTTTAAGTGGACAAGTGC
TGCGGAAGGTAAGCTCCCAGACATGAGCGACGAACTACAGTTCATTA
CTGTCATGAAGACACCACTTGAAGCACGGATCATTCCTCGCAATCCTT
GA

Figure 40

ATGGAAATGGCTCCAACAATGGATTTAGAGATAAGAAATGGAAATG
GTTATGGTGATTCTGGAGAGGAGCTTCTAGCAGCACAAGCTCACATA
TACAACCACATATTCAACTTCATAAGCTCCATGGCACTGAAATGTGCA
GTGGAGTTAAACATACCAGAAATTCTCCACAACCATCAACCCAAAGC
GGTTACTCTCTCTGAACTAGTACAGGCCCTTCAAATCCCCCAAGCAAA
ATCCGCGTGTCTGTATCGCCTGTTGCGAATACTAGTCCATTCTGGCTT
CTTTGCCATAACGAAATACAAAGCGAGGGAGATGAAGAGGGTTAT
TTACCAACCCTTTCCTCTAAACTACTACTGAAAAACCATCCCATGAGC
ATGTCTCCATGCTTGTTAGGACTGGTGAATCCTACCATGGTAGCACCC
ATGCATTTCTTTAGTGATTGGTTCAAGAGGAGTGATGATATGACGCC
GTTTGAGGCGACGCATGGAGCGAGCTTGTGGAAGTATTTTGGTGAA
ACCCCACATATGGCGGAGATATTTAATGAGGCCATGGGTTGTGAGAC
AAGGTTGGCGATGAGTGTGGTGTTGAAAGAGTGTAAGGGCAAGCTT
GAAGGAATAAGTTCGTTAGTTGATGTAGGAGGTGGTACAGGAAACG
TGGGTCGGGCAATTGCTGAAGCCTTCCCAAATGTCAAGTGCACCGTG
TTAGATTTGCCACAAGTTGTTGGAAACTTGAAAGGCAGTAACAATTT
GGAGTTTGTCAGTGGGGATATGTTTCAATTTATTCCGCCTGCAGACGT
AGTTTTCTTGAAGTGGATATTGCATGATTGGAATGATGAGGAATGTA
TAAAAATCCTAAAGAGGTGCAAGGAAGCGATTCCATCCAAGGAAGA
GGGAGGGAAATTGATCATAATAGACATGGTAGTAAACGACCACAAC
AAGGGAAGCTATGAGTCTACAGAAACGCAACTCTTCTATGATTTGAC
GCTCATGGCTCTGTTGACAGGAACAGAGAGAACCGAAACTGAATGG
AAGAAGCTCTTCGTAGCTGCTGGTTTCACAAGTTACATTATTAGCCCT
GTTTTGGGGCTCAAGTCTATCATTGAAGTGTTTCCCTAA

Figure 41

ATGGAAACATTTCAGTGCCTCACACTTTTCCTTCTCTTCATCTCCACTGTTT
TCATCCTCAAGAGAAAATTCTCTCATAAACCAAACCTACCACCATCACCAC
CAAAGCTACCAATCCTAGGCAACTTTCATCAGCTAGGCACACTTGTCCAC
CGAGCTGTTACAGTTCTCGCAGCCAAATATGGCCCCCTCATGCTCTTACAC
TTTGGCAAAACTCCAGTTCTCATTGTTTCCTCACAAGAAACGGCTAAAGA
GATCATGAAACCCATGACCTCGCTTTGGCAAATAGACCCCTAACAACTG
CTGCCAGGGCACTACTTTACGACTGCACAGATATATCTTTTGCACCTTATG
GTGAGTACTGGAGAGAAATGAAAAGATGGCAGTCCTAAACCTTCTTAG
TATCAAAAAAATCCAGTCGTTTCGATCCGTTAGGGAGGAATTGGCTTCTG
ATATGATAAGGAGATTACTCGTTTGTCCAAAACTGGAGCACCTGTGGAT
GTAACTAATATGTTATATCATTTTTCCGAAGACCTGCTTTTTAGGTGTACT
CTTGGGTTTAAACCTAAGGGACAACACAAGTTTCAGAAGCTGTCCAGGG
ATTTTTTGGATCTTGTAGGAGCTTTTTGTTTTAATGATTTCTTCCCAGGGA
TGGCATGGATGGATGCTCTCACTGGGCTAAACAGGAAGCTGAAGAAGG
GTTCAAGAGAATTAGATGACTTTGTTGATGAACTCATAGAAGAACGCATT
GCTATGGTAAAGATGGCGTTGAGCCAAATGAATTTCTGGATCTTCTACT
CCATACTCATAGAGACACCACCCAGGAAATCAAACTCACCCGAGACAAC
GTCAAAGCAATAATATTGGACACATTTCTTGGTGGAATTGATCTACCAGC
ATCAGTCATGGAATGGGCAATGGCCGAGCTTATGAGGAATCCAAGTAAG
ATGAAGATAGCTCAGGAAGAGGTCAGAAAGTGGTTGGAAACAAAAAC
AAGGTAGACGAAGACGATGTGTATCAAATGAATTTCTTGAAATCGGCTG
TTAAGGAAACTCTAAGGCTACACCCACCAGCTCCTTTGCTATTTGCGAGA
GAGTCATATACAAGTATAAACGTCGAGAACTACATCATTCCTCCTTACACT
AGTGTCATGATCAACATATGGCATATCCAAAGGGACCCCAAGTTATGGG
ACAAGGCCGAAGAGTTTATTCCAGAGAGATTCATGAACAGCGGGATTGA
TTACAAATCCCATGACTATGAATTCATCCCTTTTGGATCCGGACGAAGAG
GTTGCCCTGGTATGTCGTTTGGCGTTGCAGCAGTGGAGTTTGCTGTTGCC
AATCTCTTATACTGGTTTGATTGGAAGTTTGTTGGTGATACAACTCCTGAA
ACACTTGATATGACTGAGGACTATTGTTTTGCCCTCTTTAAGAAAAAACCT
TTGCATTTTATTCCTATTTCTCGATCCTCTTGA

Figure 42

ATGGATACTAGGGCTGATGCTGAGATTAAAGCAATGGAGCTGATTG
GTATTGGAGTACTTCCACTGGCAATGAAGGCGATAATTGAGCTCAAT
GTGTTAGAGATCCTATCAAAAGCAGGACCAGATACCCAACTCACTGC
TGCTCAAATTGTCACCGACATACCCACCACCAACCCTAACGCTGGTTT
CCAACTAGATCGAATTTTACGACTACTAGCAAGTCATTCAGTCTTGTC
TAGTAGTATTACAAAATCGGGGGAGAGAGTGTATGGGCTAACCCCT
ATGTGCAAATACTTTCTCCCAGATCAAGATGGAGTCTCACTAGCACCT
ATGGTTGTTACCATCCATGACAAAGTGCTGCTTCAAAGTTGGCATTAT
CTTAAGGACTCTGTTTTAAAACAAGGCTCTTTGCCATTTACCGAGGCC
TTTGGGATGTCACCCTTTGAGTATTCTGTCTCCGATACAAGGTTTAAT
AAGGTTTTTAATGCTGGCATGTTTGACCATTCTACTCTTTGTATGAGG
GATGTCCTTCAACGGTACAAAGGATTTCAAGGCTTGGGGGAGCTGG
TTGATGTTGGTGGAGGAACTGGCGGATCGTTGAAGATGATTCTTTCT
CAGTACCCCAATCTAAAGGGCATCAATTTTGATCTCCCACATGTGGTT
GCCGACGCGCCTTCTTTTCCTGGTGTGAAGCACATTGGTGGTGATAT
GTTTGAGAGTGTTCCCTCTGGTGATGCAATTTTCATGAAGTGGATACT
TCATGACTGGGACGATGGACGTTGCCTGACTTTGCTGAAGAATTGTT
GGAATGCATTGCCAGAGCATGGAAAGGTGATAATAGTGGAGTGGAT
TCTACCATCAGATGCAGCGACTGACCCAACATCTCGCCGTGTCTTCAC
AGCTGATTTGATGATGTTGGCTTTCAGCGAAGGGGGTAAAGAGCGA
ACCTTGGGTGACTACGGAGCACTTGCAAAGGAAGCTGGTTTTACCAC
TGTCAAAGATTTCCCTTGCGCAAATGGCATTTCAGTCATTGAATTCCA
TAAGAAGTGA

Figure 43

ATGGGTTCTACAGCACCCCTAAGGCTTCCAGTTATAGATTTATCCA
TGAAGAACTTGAAGCCTGGAACAACTTCTTGGAACTCGGTACGCA
CCCAGGTACGGGAGGCACTGGAAGAATACGGTTGCTTTGAAGCT
GTGATCGATGCTGTGTCTCCAGAGCTGCAGAAGGCAGTATGTAAC
AAAGGACACGAGCTGCTTAATCTTCCATTAGAAACCAAGATGTTG
AACGGAAACAAACCAGAATATGATGGATTTACGTCAATACCAAAC
CTCAACGAAGGCATGGGAGTCGGCAGAATAACAGATTTGGAAAA
AGTTGAGAGGTTCACTAATCTTATGTGGCCCGAGGGGAATAAGGA
TTTCTGTGAAACTGTGTATTCTTATGGCAAACGAATGGCGGAGGT
GGACCACATATTGAAATGATGGTTTTCGAGAGTTTTGGAATGGA
GAAGCACTTCGACTCGTTCTGCGAATCAACAAATTACCTTCTCCATT
TCATGAGATACCAACAACCAGGGAAGGATGGACGTTCACCTGCTC
TTTCGTTGCATAAGGACAAGAGCATCTTGACCATAGTAAACCAAAA
TGATGTCAAGGGATTGGAATTTGAAACCAAGGATGGAGAATGGA
TTTTACCTACAGCTGACAACCATATTGTTCTTCTAGGAGACTGCTTC
ATGGCATGGAGCAATGGTAGATTACATAGTCCTCTTCACCGGGTC
ACGTTGGTCGCGAACCAGGCGAGGTTATCTACATCATCGTTTTCGT
TTCCAAAGGACATAATAGAGACCCCTGCAGAGCTGGTGGATGAAG
AGCATCCTTTGCTATTTAATCCCTTTGAGATAACGGAGTTGCTTGCT
TACTGTTTCACAAAAGAGGGTGCAAAGGCGGTGTGTGACCTCAAG
CAATACAAGGCGTACACAGGTGCATGA

Figure 44

ATGGAGTTCCTTTCATTTCCCTTATCATCCGCTTTGCTCATCATCTTGTTGTTC
ATGCTGGTGAAGAAAGCAATCCAAAACAAAAATTCAAAGCTTCCCCCAGGG
CCACGGAAGCTACCTGTCATTGGAAGTTTGCACCATTTGATAGGCGATGGCC
TTCCACATCACGCACTGAGAAATCTAGCCAAAAAACATGGCCCCCTTATGCA
CCTACAACTTGGTGAAAATTCCACTCTTGTTGTATCCTCATCGAAAATGGCCA
GAGCAATCATGTCAACACACGACCTCATGTTTGCAAACAGGACTGTCCAGTT
TGCAACAGACATTTTGTTATATGGTGGTAAAGGCATTGGTTTGGCACCTTAT
GGTGATTATTGGAGGCAAATAAGAAAGATTTGCGTCTTAGAGCTCCTAAGT
GCGAAGCGTGTGCAATCATTCCAAACAGTACGGGAAGAAGAGATATCAAAT
CTCATTCGTAGTATTTCGGCTGAATCATCAAAAGTTAACTTCAGTGAAATGAT
CACATCATTAACAAATGACATAATCGCCAGGGCTGCCTTTGGCGAAAAATGC
AAAGATAAGCACGCATTCTTATCCTTGATTGAAGAAGGAATTCAGTTAGCTG
GAGGGTTTGATATTGCTGGTTTATTTCCTTCACTAAAACTCCTTCATGTCATC
ACTGGGAAAAAGCGCCAATTGGAGAGGGTACACAATGAGTTGGACAGAAT
CCTCGTAGACATCATAAAAGAAAACAAAGAGAAAGAAGAGCAAGTAAACT
TAACGAGGACAAATATGAAGAGAATCTAGTAGATGTACTTGTGCGCGTCCA
AGAGAATACTCAGCTTGAGGTTCCACTTGCAAATGACAATCTTAAAGCCGTA
ATACTAGACATCTTTGTTGCCGGAAGTGAAACATCATCCACTACAATAGAAT
GGGCAATGTCAGAAATGCTGAAAAATCCAAAAGTTATGAAGAAGGCACAAG
CTGAGGTGAGACGAGTGTTCAGTGGGAACAAAAAGATCAACGAGACGGAA
ATTCAAGAATTGAGTTACTTAAAATTAGTTCTCAAAGAAACTCTCAGGTTACA
TGCTCCAGCTCCACTGTTGATCCCCGAGAATGTAGGGAGAGTTGTGAGATT
GATGGCTATGAGATACCGAAAAAGACGATGGTTATGGTTAATGCATGGGCA
ATTGGAAGAGATCCTGAGAACTGGAGTAACGGGGATAGGTTTGAGCCAGA
GAGGTTTGATGGAATTTCTGTGGATTACAAGGGGACAAACTTTGAATACATC
CCTTTTGGAGCAGGTAGAAGAATATGTCCAGGCATGTTGTTTGGGATGGCA
AACGTTGAGGTTCCACTAGCTCGCTTACTATACCACTTCGACTGGGAACTCCC
CAACGGCATCAAACCAGAAGAGCTGGACATGGATGAGACTTTTGGTACAAC
GGTTCGAAGGAAAAATCACTTATACTTAATCCCCACTGTGGTGCATGAGCTG
GAAAGATCGACTACAAAAGAATAG

Figure 45

ATGGATTCCCTGCACTGCCTAGAAACTCTGTTGCTTGGCTTCTTTGTG
TTACTCCCATGTTTTTCTACTTTGTATGGAAGAAGCCAAATAACAAA
ATTAAAGAGCCACCCCAACCAGCTGGAGCATGGCCGATCATCGGCCA
CCTCCATCTACTAGCGCGAGGTGATCTCCCCCACAAAATTTTGTCTTC
CTTTGCAGACAAGAATGGCCCGGTTTTCAAGATACAACTTGGTGTAC
ACCAAGCACTGGTGGTAAATAATTCTGAGATAGCCAAGGAATGTTTC
ACCACAAATGACAGGTTCTTTTTAAATCGTCCTTCCGGGGTAGCAGC
AAAGATCATGGGTTACAACTATGTTATGTAGGAGTAGCCCCTTATG
GGCCTTATTGGCGTGACATGCGTAAAATAATCATGTTGGAGTTCCTCT
CCAACCGTCGGCTGCAGTCTCTAAAGCATGTATGGCACTCAGAAATA
TCAATATCTTCCAAAGAATTGTATAAACTGTGGGAAACCCAAAATAT
AGATTTTTGCCTAGTTGATATGAAGCAATGGCTGGCTGATCTCACACT
CAATATGTCAGTTAAGATGGTGGTTGGGAAGAGATTTTTCGGTTCAG
CTTCTGCTTCTGCTTGTGAAGAAACTGAGTCAAGCAATTGTCCAAAAA
CATTGAGAAATATGTTTAGACTTATGGGTTCGTTTGTGCTGTCAGACT
ATCTTCCTTATCTAAGGTGGTTGGACTTGGGAGGCCATGAGAAGGAG
ATGAAGAGAACAGTGAAAGAACTTGACATTTTATTCAAGGGATGGTT
GGATGAGCATAAAAGAAAGAGGCTATCTGGTGGGAAGGAAGACGA
CGACCAGGATTTTATGGACGTAATGCTTTCCATCCTAGAAGAATCAA
AATTGGGAAATGATGTTGATACCATCAACAAGACTGCATGCTTGGCA
ATAATACTAGGTGGAGCTGATACTACATGGGCCACCTTGACATGGGC
ACTTTCATTGTTATTGAACAATCCAAATGCGTTGAAAAAGGCCCAAG
ACGAGTTGGACTTACATGTTGGCAGGGATAGAAACGTGGACGAATC
AGACCTCGTGAAGTTGACATACATCGATGCCATTATCAAGGAAACAT
TGCGTCTATACCCACCTGGTCCGTTACTAGGTCCCCGTGTGGTCACAG
AGGATTGCACCATAGCTGGGTATCATGTTCGAGCAGGCACTCGACTA
ATTGTGAATGCTTGGAAGATACAACGAGACCCACTAGTTTGGTCGCA
ACCTCATGAGTACCAACCTGAGAGATTTCTTGAGAGAGATGTGGACA
TGAAAGGTCAACATTTTGAGTTAATCCCATTTGGATCGGGTAGACGG
GCATGCCCAGCGATCTCTTTAGCACTTCAAGTGTTGCCTTTGACGTTG
GCTCATATATTGCATGGTTTTGAGCTTAGGACCCCAAACCAGAACAA
GGTGGATATGACTGAGACACCAGGTATAGTTCATGCAAAGGCAACT
CCTTTGGAAGTACTTGTCGCCCCACGCATCTCTCCAAAATGTTTTGTC
TAG

Figure 46

ATGGGAGGAGAAAAAGCTTTCAGTTTCATTT
TCCTCCTCTTCGTGTGCTTCTTCCTAGCCAAC
CTCTCTGGGTCTTCAGCTCGCCCCCTCGTCA
TAAGCTCAAGCAACACATACCATGTAAACAA
TTAGTCCTATACTTCATGATGTGGTTTACAA
CGGTCATAACAAGGATAATGCAACAGCATCC
ATCGTAGCTGCACCACAAGGTTCAGACCTTG
TAAAATTAGCAGGGGAAAACCATTTTGGCAA
TGTGGTTGTGTTCGACGATCCAATTACTCTTG
ACAACAATTTTCACTCCCACCTGTTGGTCGT
GCACAAGGGTTGTATGTTTATGACAAGAGA
GACACATTCCACTCATGGCTAAGTTTCTCTTT
TACTCTTAATAGTACTATGCATCAAGGTACCC
TTATTTTCATGGGAGCTGACCCTATTTTAATC
AAGAATAGGGATATCACAGTTGTTGGTGGT
ACAGGGGATTTCTTCATGGCTCGAGGAATTG
CAACTATAGCAACTGATGCATACGAAGGGG
AGGTCTATTTTCGACTTAAAGTTGATATAAA
GTTGTATGAGTGTTGGTAA

SEQUENCE LISTING

<160> NUMBER OF SEQ ID NOS: 16

<210> SEQ ID NO 1
<211> LENGTH: 936
<212> TYPE: DNA
<213> ORGANISM: Artificial Sequence
<220> FEATURE:
<223> OTHER INFORMATION: SEQ ID NO:1 PLR

<400> SEQUENCE: 1

```
atggctaaga gcagagttct cattgttggg ggtacagggt acctaggaag gagaatggta      60
aaggcttgct tagaccaagg tcacactaca tatgttctac atcgtcaaga gattggcgtc     120
gacatcgata agatccagat gctattgtcg ttcaaggagc aaggggcaca ccttgttgag     180
ggctcattca atgatcatcg cagccttgtt gaggccgtga aattggttga tgttgttata     240
tgtactattt ctggagtaca tataaggagc atcagatat tgttacaact taagcttgtt     300
gaagcaatca aggaagctgg aaatgtaaag cgattcttgc catcggagtt tggtatggat    360
ccagcacgga tggcacatgc aatggaacct ggaagggcaa catttgacga aagatggtg    420
gtgagaaagg cgatcgaaga tgccaaaatt cctcatactt atgtttcagc aaattgtttt    480
gctggatact ttttgggggg tctgtgtcaa ttcggtaaga tcataccctc gaaggaaagt    540
gtaattttaa gcggagatgg caatgtaaaa ggtatttatg tggatgaata cgatattgcg   600
acttacacca tcaagaccat ggatgatcct cgtacgctga acaaaacgat ctatattagg    660
cctccagcga acattctatc tcaaagagag gtggtagaaa tttgggagaa actcattggg    720
aaagtgttag acaagtcttc cttatcagag gaggacttcc tggctctcat gaaaggtctg   780
agtcatggac atcaggcagg attgacacat tattatcatg tttcctatga ggggtgcctt   840
acaaattttg aagtagagga tggagtagat gcttcaaagc tttatccaga agtgaattac   900
actaaagtgt ccgaatatct caaacgatat ttgtag                             936
```

<210> SEQ ID NO 2
<211> LENGTH: 837
<212> TYPE: DNA
<213> ORGANISM: artificial sequence
<220> FEATURE:
<223> OTHER INFORMATION: SEQ ID NO:2 SDH

<400> SEQUENCE: 2

```
atgggatcca cttctacacc agcttcgtct accaacaggt tacaagataa agtagccatc      60
ataacagggg gagcaggtgg gattggtgaa accacagcaa aattattcgt ccgctacggt    120
gctaaagttg tgatagcaga catctcagat gaccacggcc aaaaagtttg taacaacatt     180
ggctcaccgg acgtgatctc tttcgttcat tgtgatgtga ccaaagatga ggacgtccgg    240
aacctagtgg ataccaccat agccaagcat ggaaaacttg acataatgtt cggcaacgtt    300
ggtgttctga gcaccactcc ttacagcata ctggaagctg gaaatgaaga tttcaagaga    360
gttatggaca ttaacgtgta tggtgcattt ttagtagcca acacgctgc ccgagtcatg    420
atcccagcga agaaaggtag tatagtattc actgcaagta tttcttcctt cacagcagga    480
gaaggtgtgt cgcatgtttta cactgcaacc aagcatgctg tccttggatt gacaactagc    540
ttatgtactg agctaggaca gcatgggatc cgagtgaact gtgtatctcc ctatgttgtt    600
gcatccccat tgttgaccga tgtgtttgga gtggattcta gtaggttga ggaattggca    660
catcaagctg caaacttgaa agggattttg ctcagggctg aggatgtggc cgatgcagtc    720
gcttatttgg caggggatga gtccaagtat gtgagcggcc tgaaccttgt tatcgatggg    780
```

```
ggctacacca gaaccaatcc agctttccca accgcattga acatggatt  ggcttga        837
```

<210> SEQ ID NO 3
<211> LENGTH: 1470
<212> TYPE: DNA
<213> ORGANISM: Artificial Sequence
<220> FEATURE:
<223> OTHER INFORMATION: SEQ ID NO:3 CYP719A23

<400> SEQUENCE: 3

```
atggagatgg agatgagtgt cttggctatg agctccactt tgatattagc cttggctatg     60
gcactgatat tcttattcaa agcaaagtcg tcttctgcaa ttaaatggcc tccagggcca    120
aaaacattac ccatcatcgg taatctccac caactaggag gtgatgagct gcacattgtt    180
ctcgctaagc ttgctagagt tcacggtgct atcatgacca tctggatggc aaagaaacca    240
gtgattgttg tcagcgatgt gaactcagtt tgggaggtgc ttgtgagcaa gtcctctgac    300
tatgctgctc gcgatgcggc tgaaatttcc aaaatagtct ctgccagctc tcactctatc    360
aacacatcgg actcaggccc ttattggcag actcttcgta ggggacttac gcatggtcct    420
ttagggccgc tcaacatatc agcgcaaatc ccgatccagc agaggacat  gcaaagagtc    480
attcgagaga tgcaacaaga tgctgctgca acgggggaa  tcattaagcc actcgaccat    540
cttaaaagat cttccacaag attagtgagt cgactcatct ttggagacac ctttgacaat    600
gacccttata tgattcgat  gcacgaagta gtccaagatc taaatcggtt cggtggtata    660
gctctacttg aacaagcatt ctcatttgct aaacacctcc ctagttacaa gcgtggcgtc    720
aaagaattcc acatacacaa aggaaaatc  gatgacttgg taagacctgt cgtagcatct    780
gcaaatcctc ccagtaatag ttacctaggc tttcttcaat ctcaaaacta ttcagaagag    840
attatcatag cttgcatctt tgaattgtac cttttggcta tggacagttc tgcatctaca    900
gctacatggg ctctagcttt catgatacgc gaccaacaag ttcaggaaaa gctctatcaa    960
gatatcaaac gtgttatcgg tgatggggta gaccttgtga agcagaaga  tttaagtaag   1020
atgcattatt tacaagcagt ggtgaaagag actatgagga tgaagccaat agcacctctg   1080
gcaattcctc acaagactgc tattgacacc accgtgatgg ggactaaggt gcctaaggga   1140
acctgtgtaa tggtcaatct ttacgcttta catcatgacg aaagcgtctg gccaaaccg    1200
tatacattta tgccagagag gttcttgcaa ggcgaagacg taaaagcgt  tacagagcaa   1260
gcatttctac catttggtgc tggtatgaga atctgtggag aatggaggt  ggggaagctc   1320
cagttttctt tggcactcgc gaattagtg  aatgcgttta gtggacaag  tgctgcggaa   1380
ggtaagctcc cagacatgag cgacgaacta cagttcatta ctgtcatgaa gacaccactt   1440
gaagcacgga tcattcctcg caatccttga                                    1470
```

<210> SEQ ID NO 4
<211> LENGTH: 1119
<212> TYPE: DNA
<213> ORGANISM: Artificial Sequence
<220> FEATURE:
<223> OTHER INFORMATION: SEQ ID NO:4 OMT3

<400> SEQUENCE: 4

```
atggaaatgg ctccaacaat ggatttagag ataagaaatg gaaatggtta tggtgattct     60
ggagaggagc ttctagcagc acaagctcac atatacaacc acatattcaa cttcataagc    120
tccatggcac tgaaatgtgc agtggagtta aacataccag aaattctcca caaccatcaa    180
```

| | |
|---|---|
| cccaaagcgg ttactctctc tgaactagta caggcccttc aaatccccca agcaaaatcc | 240 |
| gcgtgtctgt atcgcctgtt gcgaatacta gtccattctg gcttctttgc cataacgaaa | 300 |
| atacaaagcg agggagatga agagggttat ttaccaaccc tttcctctaa actactactg | 360 |
| aaaaaccatc ccatgagcat gtctccatgc ttgttaggac tggtgaatcc taccatggta | 420 |
| gcacccatgc atttctttag tgattggttc aagaggagtg atgatatgac gccgtttgag | 480 |
| gcgacgcatg gagcgagctt gtggaagtat tttggtgaaa ccccacatat ggcggagata | 540 |
| tttaatgagg ccatggggttg tgagacaagg ttggcgatga gtgtggtgtt gaaagagtgt | 600 |
| aagggcaagc ttgaaggaat aagttcgtta gttgatgtag gaggtggtac aggaaacgtg | 660 |
| ggtcgggcaa ttgctgaagc cttcccaaat gtcaagtgca ccgtgttaga tttgccacaa | 720 |
| gttgttggaa acttgaaagg cagtaacaat ttggagtttg tcagtgggga tatgtttcaa | 780 |
| tttattccgc ctgcagacgt agttttcttg aagtggatat tgcatgattg gaatgatgag | 840 |
| gaatgtataa aaatcctaaa gaggtgcaag gaagcgattc catccaagga agagggaggg | 900 |
| aaattgatca taatagacat ggtagtaaac gaccacaaca agggaagcta tgagtctaca | 960 |
| gaaacgcaac tcttctatga tttgacgctc atggctctgt tgacaggaac agagagaacc | 1020 |
| gaaactgaat ggaagaagct cttcgtagct gctggtttca aagttacat tattagccct | 1080 |
| gttttggggc tcaagtctat cattgaagtg tttccctaa | 1119 |

```
<210> SEQ ID NO 5
<211> LENGTH: 1482
<212> TYPE: DNA
<213> ORGANISM: Artificial Sequence
<220> FEATURE:
<223> OTHER INFORMATION: SEQ ID NO:5 CYP71CU1

<400> SEQUENCE: 5
```

| | |
|---|---|
| atggaaacat tcagtgcct cacacttttc cttctcttca tctccactgt tttcatcctc | 60 |
| aagagaaaat tctctcataa accaaaccta ccaccatcac caccaaagct accaatccta | 120 |
| ggcaactttc atcagctagg cacacttgtc caccgagctg ttacagttct cgcagccaaa | 180 |
| tatggccccc tcatgctctt acactttggc aaaactccag ttctcattgt tcctcacaa | 240 |
| gaaacggcta aagagatcat gaaaacccat gacctcgctt tggcaaatag ccccctaaca | 300 |
| actgctgcca gggcactact ttacgactgc acagatatat cttttgcacc ttatggtgag | 360 |
| tactggagag aaatgaaaaa gatggcagtc ctaaaccttc ttagtatcaa aaaaatccag | 420 |
| tcgtttcgat ccgttaggga ggaattggct tctgatatga taaaggagat tactcgtttg | 480 |
| tccaaaactg agcacctgt ggatgtaact aatatgttat atcattttc cgaagacctg | 540 |
| cttttaggt gtactcttgg gtttaaacct aagggacaac acaagtttca gaagctgtcc | 600 |
| agggattttt tggatcttgt aggagctttt tgttttaatg atttcttccc agggatggca | 660 |
| tggatggatg ctctcactgg gctaaacagg aagctgaaga agggttcaag agaattagat | 720 |
| gactttgttg atgaactcat agaagaacgc attgctatgg taaaagatgg cgttgagcca | 780 |
| aatgaatttc tggatcttct actccatact catagagaca ccacccagga aatcaaactc | 840 |
| acccgagaca acgtcaaagc aataatattg gacacatttc ttggtggaat tgatctacca | 900 |
| gcatcagtca tggaatgggc aatggccgag cttatgagga atccaagtaa gatgaagata | 960 |
| gctcaggaag aggtcagaaa agtggttgga aacaaaaaca aggtagacga agacgatgtg | 1020 |
| tatcaaatga atttcttgaa atcggctgtt aaggaaactc taaggctaca cccaccagct | 1080 |
| cctttgctat tgcgagaga gtcatataca agtataaacg tcgagaacta catcattcct | 1140 |

```
ccttacacta gtgtcatgat caacatatgg catatccaaa gggaccccaa gttatgggac    1200
aaggccgaag agtttattcc agagagattc atgaacagcg ggattgatta caaatcccat    1260
gactatgaat tcatcccttt tggatccgga cgaagaggtt gccctggtat gtcgtttggc    1320
gttgcagcag tggagtttgc tgttgccaat ctcttatact ggtttgattg gaagtttgtt    1380
ggtgatacaa ctcctgaaac acttgatatg actgaggact attgttttgc cctctttaag    1440
aaaaaacctt tgcattttat tcctatttct cgatcctctt ga                       1482
```

<210> SEQ ID NO 6
<211> LENGTH: 1050
<212> TYPE: DNA
<213> ORGANISM: Artificial Sequence
<220> FEATURE:
<223> OTHER INFORMATION: SEQ ID NO:6 OMT1

<400> SEQUENCE: 6

```
atggatacta gggctgatgc tgagattaaa gcaatggagc tgattggtat tggagtactt     60
ccactggcaa tgaaggcgat aattgagctc aatgtgttag agatcctatc aaaagcagga    120
ccagataccc aactcactgc tgctcaaatt gtcaccgaca tacccaccac caaccctaac    180
gctggtttcc aactagatcg aattttacga ctactagcaa gtcattcagt cttgtctagt    240
agtattacaa aatcggggga gagagtgtat gggctaaccc ctatgtgcaa atactttctc    300
ccagatcaag atggagtctc actagcacct atggttgtta ccatccatga caaagtgctg    360
cttcaaagtt ggcattatct taaggactct gttttaaaac aaggctcttt gccatttacc    420
gaggcctttg ggatgtcacc ctttgagtat tctgtctccg atacaaggtt taataaggtt    480
tttaatgctg gcatgtttga ccattctact ctttgtatga gggatgtcct tcaacggtac    540
aaaggatttc aaggcttggg ggagctggtt gatgttggtg gaggaactgg cggatcgttg    600
aagatgattc tttctcagta ccccaatcta aagggcatca attttgatct cccacatgtg    660
gttgccgacg cgccttcttt tcctggtgtg aagcacattg tggtgatat gtttgagagt    720 gttccctctg gtgatgcaat tttcatgaag tggatacttc atgactggga cgatggacgt    780
tgcctgactt tgctgaagaa ttgttggaat gcattgccag agcatggaaa ggtgataata    840
gtggagtgga ttctaccatc agatgcagcg actgacccaa catctcgccg tgtcttcaca    900
gctgatttga tgatgttggc tttcagcgaa gggggtaaag agcgaacctt gggtgactac    960
ggagcacttg caaaggaagc tggttttacc actgtcaaag atttcccttg cgcaaatggc    1020
atttcagtca ttgaattcca taagaagtga                                     1050
```

<210> SEQ ID NO 7
<211> LENGTH: 933
<212> TYPE: DNA
<213> ORGANISM: Artificial Sequence
<220> FEATURE:
<223> OTHER INFORMATION: SEQ ID NO:7 2-ODD

<400> SEQUENCE: 7

```
atgggttcta cagcaccccct aaggcttcca gttatagatt tatccatgaa gaacttgaag     60
cctggaacaa cttcttggaa ctcggtacgc acccaggtac gggaggcact ggaagaatac    120
ggttgctttg aagctgtgat cgatgctgtg tctccagagc tgcagaaggc agtatgtaac    180
aaaggacacg agctgcttaa tcttccatta gaaaccaaga tgttgaacgg aaacaaacca    240
gaatatgatg gatttacgtc aataccaaac ctcaacgaag gcatgggagt cggcagaata    300
```

```
acagatttgg aaaaagttga gaggttcact aatcttatgt ggcccgaggg gaataaggat    360
ttctgtgaaa ctgtgtattc ttatggcaaa cgaatggcgg aggtggacca catattgaaa    420
atgatggttt tcgagagttt tggaatggag aagcacttcg actcgttctg cgaatcaaca    480
aattaccttc tccatttcat gagataccaa caaccaggga aggatggacg ttcacctgct    540
ctttcgttgc ataaggacaa gagcatcttg accatagtaa accaaaatga tgtcaaggga    600
ttggaatttg aaaccaagga tggagaatgg attttaccta cagctgacaa ccatattgtt    660
cttctaggag actgcttcat ggcatggagc aatggtagat acatagtcc tcttcaccgg    720
gtcacgttgg tcgcgaacca ggcgaggtta tctacatcat cgttttcgtt tccaaaggac    780
ataatagaga cccctgcaga gctggtggat gaagagcatc ctttgctatt taatccctt    840
gagataacgg agttgcttgc ttactgtttc acaaaagagg gtgcaaaggc ggtgtgtgac    900
ctcaagcaat acaaggcgta cacaggtgca tga                                 933
```

<210> SEQ ID NO 8
<211> LENGTH: 1524
<212> TYPE: DNA
<213> ORGANISM: Artificial Sequence
<220> FEATURE:
<223> OTHER INFORMATION: SEQ ID NO:8 CYP71BE54

<400> SEQUENCE: 8

```
atggagttcc tttcatttcc cttatcatcc gctttgctca tcatcttgtt gttcatgctg     60
gtgaagaaag caatccaaaa caaaaattca aagcttcccc cagggccacg gaagctacct    120
gtcattggaa gtttgcacca tttgataggc gatggccttc acatcacgc actgagaaat    180
ctagccaaaa acatggcccc cttatgcac ctacaacttg gtgaaaattc cactcttgtt    240
gtatcctcat cgaaaatggc cagagcaatc atgtcaacac acgacctcat gtttgcaaac    300
aggactgtcc agtttgcaac agacattttg ttatatggtg gtaaaggcat tggtttggca    360
ccttatggtg attattggag gcaaataaga aagatttgcg tcttagagct cctaagtgcg    420
aagcgtgtgc aatcattcca acagtacgg gaagaagaga tatcaaatct cattcgtagt    480
atttcggctg aatcatcaaa agttaacttc agtgaaatga tcacatcatt aacaaatgac    540
ataatcgcca gggctgcctt tggcgaaaaa tgcaaagata agcacgcatt cttatccttg    600
attgaagaag gaattcagtt agctggaggg tttgatattg ctggtttatt tccttcacta    660
aaactccttc atgtcatcac tgggaaaaag cgccaattgg agagggtaca caatgagttg    720
gacagaatcc tcgtagacat cataaaagaa acaaagaga aagaagagc aagtaaactt    780
aacgaggaca aatatgaaga aatctagta gatgtacttg tgcgcgtcca agagaatact    840
cagcttgagt tccacttgc aaatgacaat cttaaagccg taatactaga catcttgtt    900
gccggaagtg aaacatcatc cactacaata gaatgggcaa tgtcagaaat gctgaaaaat    960
ccaaaagtta tgaagaaggc acaagctgag gtgagacgag tgttcagtgg gaacaaaaag   1020
atcaacgaga cggaaattca agaattgagt tacttaaaat tagttctcaa agaaactctc   1080
aggttacatg ctccagctcc actgttgatc ccccgagaat gtagggagag ttgtgagatt   1140
gatggctatg agataccgaa aaagacgatg gttatggtta atgcatgggc aattggaaga   1200
gatcctgaga actggagtaa cggggatagg tttgagccag agaggtttga tggaatttct   1260
gtggattaca aggggacaaa ctttgaatac atcccttttg gagcaggtag aagaatatgt   1320
ccaggcatgt tgtttgggat ggcaaacgtt gaggttccac tagctcgctt actataccac   1380
ttcgactggg aactccccaa cggcatcaaa ccagaagagc tggacatgga tgagactttt   1440
```

```
ggtacaacgg ttcgaaggaa aaatcactta tacttaatcc ccactgtggt gcatgagctg    1500
gaaagatcga ctacaaaaga atag                                           1524
```

<210> SEQ ID NO 9
<211> LENGTH: 1560
<212> TYPE: DNA
<213> ORGANISM: Artificial Sequence
<220> FEATURE:
<223> OTHER INFORMATION: SEQ ID NO:9 CYP82D61

<400> SEQUENCE: 9

```
atggattccc tgcactgcct agaaactctg ttgcttggct tctttgtgtt actcccatgt      60
tttttctact ttgtatggaa gaagccaaat aacaaaatta agagccacc ccaaccagct     120 ggagcatggc cgatcatcgg ccacctccat ctactagcgc gaggtgatct cccccacaaa    180
attttgtctt cctttgcaga caagaatggc ccggttttca agatacaact tggtgtacac    240
caagcactgg tggtaaataa ttctgagata gccaaggaat gtttcaccac aaatgacagg    300 ttcttttta atcgtccttc cggggtagca gcaaagatca tgggttacaa ctatgttatg    360
ttaggagtag cccctatgg gccttattgg cgtgacatgc gtaaaataat catgttggag    420
ttcctctcca accgtcggct gcagtctcta aagcatgtat ggcactcaga aatatcaata    480
tcttccaaag aattgtataa actgtgggaa acccaaaata tagatttttg cctagttgat    540
atgaagcaat ggctggctga tctcacactc aatatgtcag ttaagatggt ggttgggaag    600 agattttcg ttcagcttc tgcttctgct tgtgaagaaa ctgagtcaag caattgtcca     660
aaaacattga gaaatatgtt tagacttatg ggttcgtttg tgctgtcaga ctatcttcct    720
tatctaaggt ggttggactt gggaggccat gagaaggaga tgaagagaac agtgaaagaa    780
cttgacattt tattcaaggg atggttggat gagcataaaa gaaagaggct atctggtggg    840
aaggaagacg acgaccagga ttttatggac gtaatgcttt ccatcctaga gaatcaaaa     900 ttgggaaatg atgttgatac catcaacaag actgcatgct tggcaataat actaggtgga    960
gctgatacta catgggccac cttgacatgg gcactttcat tgttattgaa caatccaaat   1020
gcgttgaaaa aggcccaaga cgagttggac ttacatgttg gcagggatag aaacgtggac   1080
gaatcagacc tcgtgaagtt gacatacatc gatgccatta tcaaggaaac attgcgtcta   1140
tacccacctg gtccgttact aggtccccgt gtggtcacag aggattgcac catagctggg   1200
tatcatgttc gagcaggcac tcgactaatt gtgaatgctt ggaagataca acgagaccca   1260
ctagtttggt cgcaacctca tgagtaccaa cctgagagat tcttgagag atgtgggac     1320 atgaaaggtc aacattttga gttaatccca tttggatcgg gtagacgggc atgcccagcg   1380
atctctttag cacttcaagt gttgccttg acgttggctc atatattgca tggttttgag    1440
cttaggaccc caaaccagaa caaggtggat atgactgaga caccaggtat agttcatgca   1500
aaggcaactc ctttggaagt acttgtcgcc ccacgcatct ctccaaaatg ttttgtctag   1560
```

<210> SEQ ID NO 10
<211> LENGTH: 582
<212> TYPE: DNA
<213> ORGANISM: Artificial Sequence
<220> FEATURE:
<223> OTHER INFORMATION: SEQ ID NO:10 DIR

<400> SEQUENCE: 10

```
atgggaggag aaaaagcttt cagtttcatt ttcctcctct tcgtgtgctt cttcctagcc      60
```

```
aacctctctg ggtcttcagc tcgccccct cgtcataagc tcaagcaaca cataccatgt    120
aaacaattag tcctatactt ccatgatgtg gtttacaacg gtcataacaa ggataatgca    180
acagcatcca tcgtagctgc accacaaggt tcagaccttg taaaattagc aggggaaaac    240
cattttggca atgtggttgt gttcgacgat ccaattactc ttgacaacaa ttttcactcc    300
ccacctgttg gtcgtgcaca agggttgtat gtttatgaca agagagacac attccactca    360
tggctaagtt tctctttac tcttaatagt actatgcatc aaggtaccct tatttcatg     420 ggagctgacc ctatttaat caagaatagg gatatcacag ttgttggtgg tacaggggat    480
ttcttcatgg ctcgaggaat tgcaactata gcaactgatg catacgaagg ggaggtctat    540
tttcgactta aagttgatat aaagttgtat gagtgttggt aa                      582
```

<210> SEQ ID NO 11
<211> LENGTH: 372
<212> TYPE: PRT
<213> ORGANISM: Artificial Sequence
<220> FEATURE:
<223> OTHER INFORMATION: SEQ ID NO:11 OMT3

<400> SEQUENCE: 11

```
Met Glu Met Ala Pro Thr Met Asp Leu Glu Ile Arg Asn Gly Asn Gly
1               5                   10                  15

Tyr Gly Asp Ser Gly Glu Glu Leu Leu Ala Ala Gln Ala His Ile Tyr
            20                  25                  30

Asn His Ile Phe Asn Phe Ile Ser Ser Met Ala Leu Lys Cys Ala Val
        35                  40                  45

Glu Leu Asn Ile Pro Glu Ile Leu His Asn His Gln Pro Lys Ala Val
    50                  55                  60

Thr Leu Ser Glu Leu Val Gln Ala Leu Gln Ile Pro Gln Ala Lys Ser
65                  70                  75                  80

Ala Cys Leu Tyr Arg Leu Leu Arg Ile Leu Val His Ser Gly Phe Phe
                85                  90                  95

Ala Ile Thr Lys Ile Gln Ser Glu Gly Asp Glu Gly Tyr Leu Pro
            100                 105                 110

Thr Leu Ser Ser Lys Leu Leu Leu Lys Asn His Pro Met Ser Met Ser
        115                 120                 125

Pro Cys Leu Leu Gly Leu Val Asn Pro Thr Met Val Ala Pro Met His
    130                 135                 140

Phe Phe Ser Asp Trp Phe Lys Arg Ser Asp Asp Met Thr Pro Phe Glu
145                 150                 155                 160

Ala Thr His Gly Ala Ser Leu Trp Lys Tyr Phe Gly Glu Thr Pro His
                165                 170                 175

Met Ala Glu Ile Phe Asn Glu Ala Met Gly Cys Glu Thr Arg Leu Ala
            180                 185                 190

Met Ser Val Val Leu Lys Glu Cys Lys Gly Lys Leu Glu Gly Ile Ser
        195                 200                 205

Ser Leu Val Asp Val Gly Gly Gly Thr Gly Asn Val Gly Arg Ala Ile
    210                 215                 220

Ala Glu Ala Phe Pro Asn Val Lys Cys Thr Val Leu Asp Leu Pro Gln
225                 230                 235                 240

Val Val Gly Asn Leu Lys Gly Ser Asn Asn Leu Glu Phe Val Ser Gly
                245                 250                 255

Asp Met Phe Gln Phe Ile Pro Pro Ala Asp Val Val Pro Leu Lys Trp
            260                 265                 270
```

```
Ile Leu His Asp Trp Asn Asp Glu Glu Cys Ile Lys Ile Leu Lys Arg
            275                 280                 285

Cys Lys Glu Ala Ile Pro Ser Lys Glu Glu Gly Gly Lys Leu Ile Ile
        290                 295                 300

Ile Asp Met Val Val Asn Asp His Asn Lys Gly Ser Tyr Glu Ser Thr
305                 310                 315                 320

Glu Thr Gln Leu Phe Tyr Asp Leu Thr Leu Met Ala Leu Leu Thr Gly
                325                 330                 335

Thr Glu Arg Thr Glu Thr Glu Trp Lys Lys Leu Phe Val Ala Ala Gly
            340                 345                 350

Phe Thr Ser Tyr Ile Ile Ser Pro Val Leu Gly Leu Lys Ser Ile Ile
        355                 360                 365

Glu Val Phe Pro
    370

<210> SEQ ID NO 12
<211> LENGTH: 493
<212> TYPE: PRT
<213> ORGANISM: Artificial Sequence
<220> FEATURE:
<223> OTHER INFORMATION: SEQ ID 12: CYP71CU1

<400> SEQUENCE: 12

Met Glu Thr Phe Gln Cys Leu Thr Leu Phe Leu Leu Phe Ile Ser Thr
1               5                   10                  15

Val Phe Ile Leu Lys Arg Lys Phe Ser His Lys Pro Asn Leu Pro Pro
            20                  25                  30

Ser Pro Pro Lys Leu Pro Ile Leu Gly Asn Phe His Gln Leu Gly Thr
        35                  40                  45

Leu Val His Arg Ala Val Thr Val Leu Ala Ala Lys Tyr Gly Pro Leu
    50                  55                  60

Met Leu Leu His Phe Gly Lys Thr Pro Val Leu Ile Val Ser Ser Gln
65                  70                  75                  80

Glu Thr Ala Lys Glu Ile Met Lys Thr His Asp Leu Ala Leu Ala Asn
                85                  90                  95

Arg Pro Leu Thr Thr Ala Ala Arg Ala Leu Leu Tyr Asp Cys Thr Asp
            100                 105                 110

Ile Ser Phe Ala Pro Tyr Gly Glu Tyr Trp Arg Glu Met Lys Lys Met
        115                 120                 125

Ala Val Leu Asn Leu Leu Ser Ile Lys Lys Ile Gln Ser Phe Arg Ser
    130                 135                 140

Val Arg Glu Glu Leu Ala Ser Asp Met Ile Lys Glu Ile Thr Arg Leu
145                 150                 155                 160

Ser Lys Thr Gly Ala Pro Val Asp Val Thr Asn Met Leu Tyr His Phe
                165                 170                 175

Ser Glu Asp Leu Leu Phe Arg Cys Thr Leu Gly Phe Lys Pro Lys Gly
            180                 185                 190

Gln His Lys Phe Gln Lys Leu Ser Arg Asp Phe Leu Asp Leu Val Gly
        195                 200                 205

Ala Phe Cys Phe Asn Asp Phe Phe Pro Gly Met Ala Trp Met Asp Ala
    210                 215                 220

Leu Thr Gly Leu Asn Arg Lys Leu Lys Lys Gly Ser Arg Glu Leu Asp
225                 230                 235                 240

Asp Phe Val Asp Glu Leu Ile Glu Glu Arg Ile Ala Met Val Lys Asp
                245                 250                 255
```

```
Gly Val Glu Pro Asn Glu Phe Leu Asp Leu Leu His Thr His Arg
            260                 265                 270
Asp Thr Thr Gln Glu Ile Lys Leu Thr Arg Asp Asn Val Lys Ala Ile
275                 280                 285
Ile Leu Asp Thr Phe Leu Gly Gly Ile Asp Leu Pro Ala Ser Val Met
            290                 295                 300
Glu Trp Ala Met Ala Glu Leu Met Arg Asn Pro Ser Lys Met Lys Ile
305                 310                 315                 320
Ala Gln Glu Glu Val Arg Lys Val Val Gly Asn Lys Asn Lys Val Asp
                    325                 330                 335
Glu Asp Asp Val Tyr Gln Met Asn Phe Leu Lys Ser Ala Val Lys Glu
            340                 345                 350
Thr Leu Arg Leu His Pro Pro Ala Pro Leu Leu Phe Ala Arg Glu Ser
            355                 360                 365
Tyr Thr Ser Ile Asn Val Glu Asn Tyr Ile Ile Pro Pro Tyr Thr Ser
            370                 375                 380
Val Met Ile Asn Ile Trp His Ile Gln Arg Asp Pro Lys Leu Trp Asp
385                 390                 395                 400
Lys Ala Glu Glu Phe Ile Pro Glu Arg Phe Met Asn Ser Gly Ile Asp
                    405                 410                 415
Tyr Lys Ser His Asp Tyr Glu Phe Ile Pro Phe Gly Ser Gly Arg Arg
            420                 425                 430
Gly Cys Pro Gly Met Ser Phe Gly Val Ala Ala Val Glu Phe Ala Val
            435                 440                 445
Ala Asn Leu Leu Tyr Trp Phe Asp Trp Lys Phe Val Gly Asp Thr Thr
450                 455                 460
Pro Glu Thr Leu Asp Met Thr Glu Asp Tyr Cys Phe Ala Leu Phe Lys
465                 470                 475                 480
Lys Lys Pro Leu His Phe Ile Pro Ile Ser Arg Ser Ser
            485                 490

<210> SEQ ID NO 13
<211> LENGTH: 349
<212> TYPE: PRT
<213> ORGANISM: Artificial Sequence
<220> FEATURE:
<223> OTHER INFORMATION: SEQ ID NO:13 OMT1

<400> SEQUENCE: 13

Met Asp Thr Arg Ala Asp Ala Glu Ile Lys Ala Met Glu Leu Ile Gly
1               5                   10                  15
Ile Gly Val Leu Pro Leu Ala Met Lys Ala Ile Ile Glu Leu Asn Val
            20                  25                  30
Leu Glu Ile Leu Ser Lys Ala Gly Pro Asp Thr Gln Leu Thr Ala Ala
        35                  40                  45
Gln Ile Val Thr Asp Ile Pro Thr Thr Asn Pro Asn Ala Gly Phe Gln
    50                  55                  60
Leu Asp Arg Ile Leu Arg Leu Leu Ala Ser His Ser Val Leu Ser Ser
65                  70                  75                  80
Ser Ile Thr Lys Ser Gly Glu Arg Val Tyr Gly Leu Thr Pro Met Cys
                85                  90                  95
Lys Tyr Phe Leu Pro Asp Gln Asp Gly Val Ser Leu Ala Pro Met Val
            100                 105                 110
Val Thr Ile His Asp Lys Val Leu Leu Gln Ser Trp His Tyr Leu Lys
        115                 120                 125
```

```
Asp Ser Val Leu Lys Gln Gly Ser Leu Pro Phe Thr Glu Ala Phe Gly
    130                 135                 140

Met Ser Pro Phe Glu Tyr Ser Val Ser Asp Thr Arg Phe Asn Lys Val
145                 150                 155                 160

Phe Asn Ala Gly Met Phe Asp His Ser Thr Leu Cys Met Arg Asp Val
                165                 170                 175

Leu Gln Arg Tyr Lys Gly Phe Gln Gly Leu Gly Leu Val Asp Val
            180                 185                 190

Gly Gly Gly Thr Gly Gly Ser Leu Lys Met Ile Leu Ser Gln Tyr Pro
            195                 200                 205

Asn Leu Lys Gly Ile Asn Phe Asp Leu Pro His Val Val Ala Asp Ala
    210                 215                 220

Pro Ser Phe Pro Gly Val Lys His Ile Gly Gly Asp Met Phe Glu Ser
225                 230                 235                 240

Val Pro Ser Gly Asp Ala Ile Phe Met Lys Trp Ile Leu His Asp Trp
                245                 250                 255

Asp Asp Gly Arg Cys Leu Thr Leu Leu Lys Asn Cys Trp Asn Ala Leu
            260                 265                 270

Pro Glu His Gly Lys Val Ile Ile Val Glu Trp Ile Leu Pro Ser Asp
            275                 280                 285

Ala Ala Thr Asp Pro Thr Ser Arg Arg Val Phe Thr Ala Asp Leu Met
    290                 295                 300

Met Leu Ala Phe Ser Glu Gly Lys Glu Arg Thr Leu Gly Asp Tyr
305                 310                 315                 320

Gly Ala Leu Ala Lys Glu Ala Gly Phe Thr Thr Val Lys Asp Phe Pro
                325                 330                 335

Cys Ala Asn Gly Ile Ser Val Ile Glu Phe His Lys Lys
                340                 345

<210> SEQ ID NO 14
<211> LENGTH: 310
<212> TYPE: PRT
<213> ORGANISM: Artificial Sequence
<220> FEATURE:
<223> OTHER INFORMATION: SEQ ID NO: 14 2-ODD

<400> SEQUENCE: 14

Met Gly Ser Thr Ala Pro Leu Arg Leu Pro Val Ile Asp Leu Ser Met
1               5                   10                  15

Lys Asn Leu Lys Pro Gly Thr Thr Ser Trp Asn Ser Val Arg Thr Gln
            20                  25                  30

Val Arg Glu Ala Leu Glu Glu Tyr Gly Cys Phe Glu Ala Val Ile Asp
            35                  40                  45

Ala Val Ser Pro Glu Leu Gln Lys Ala Val Cys Asn Lys Gly His Glu
    50                  55                  60

Leu Leu Asn Leu Pro Leu Glu Thr Lys Met Leu Asn Gly Asn Lys Pro
65                  70                  75                  80

Glu Tyr Asp Gly Phe Thr Ser Ile Pro Asn Leu Asn Glu Gly Met Gly
                85                  90                  95

Val Gly Arg Ile Thr Asp Leu Glu Lys Val Glu Arg Phe Thr Asn Leu
            100                 105                 110

Met Trp Pro Glu Gly Asn Lys Asp Phe Cys Glu Thr Val Tyr Ser Tyr
        115                 120                 125

Gly Lys Arg Met Ala Glu Val Asp His Ile Leu Lys Met Met Val Phe
    130                 135                 140
```

Glu Ser Phe Gly Met Glu Lys His Phe Asp Ser Phe Cys Glu Ser Thr
145                 150                 155                 160

Asn Tyr Leu Leu His Phe Met Arg Tyr Gln Gln Pro Gly Lys Asp Gly
                165                 170                 175

Arg Ser Pro Ala Leu Ser Leu His Lys Asp Lys Ser Ile Leu Thr Ile
            180                 185                 190

Val Asn Gln Asn Asp Val Lys Gly Leu Glu Phe Glu Thr Lys Asp Gly
        195                 200                 205

Glu Trp Ile Leu Pro Thr Ala Asp Asn His Ile Val Leu Leu Gly Asp
    210                 215                 220

Cys Phe Met Ala Trp Ser Asn Gly Arg Leu His Ser Pro Leu His Arg
225                 230                 235                 240

Val Thr Leu Val Ala Asn Gln Ala Arg Leu Ser Thr Ser Ser Phe Ser
                245                 250                 255

Phe Pro Lys Asp Ile Ile Glu Thr Pro Ala Glu Leu Val Asp Glu Glu
                260                 265                 270

His Pro Leu Leu Phe Asn Pro Phe Glu Ile Thr Glu Leu Leu Ala Tyr
            275                 280                 285

Cys Phe Thr Lys Glu Gly Ala Lys Ala Val Cys Asp Leu Lys Gln Tyr
        290                 295                 300

Lys Ala Tyr Thr Gly Ala
305                 310

<210> SEQ ID NO 15
<211> LENGTH: 507
<212> TYPE: PRT
<213> ORGANISM: Artificial Sequence
<220> FEATURE:
<223> OTHER INFORMATION: SEQ ID NO:15 CYP71CE54

<400> SEQUENCE: 15

Met Glu Phe Leu Ser Phe Pro Leu Ser Ala Leu Leu Ile Ile Leu
1               5                   10                  15

Leu Phe Met Leu Val Lys Lys Ala Ile Gln Asn Lys Asn Ser Lys Leu
                20                  25                  30

Pro Pro Gly Pro Arg Lys Leu Pro Val Ile Gly Ser Leu His His Leu
            35                  40                  45

Ile Gly Asp Gly Leu Pro His His Ala Leu Arg Asn Leu Ala Lys Lys
50                  55                  60

His Gly Pro Leu Met His Leu Gln Leu Gly Glu Asn Ser Thr Leu Val
65                  70                  75                  80

Val Ser Ser Ser Lys Met Ala Arg Ala Ile Met Ser Thr His Asp Leu
                85                  90                  95

Met Phe Ala Asn Arg Thr Val Gln Phe Ala Thr Asp Ile Leu Leu Tyr
            100                 105                 110

Gly Gly Lys Gly Ile Gly Leu Ala Pro Tyr Gly Asp Tyr Trp Arg Gln
        115                 120                 125

Ile Arg Lys Ile Cys Val Leu Glu Leu Leu Ser Ala Lys Arg Val Gln
    130                 135                 140

Ser Phe Gln Thr Val Arg Glu Glu Ile Ser Asn Leu Ile Arg Ser
145                 150                 155                 160

Ile Ser Ala Glu Ser Ser Lys Val Asn Phe Ser Glu Met Ile Thr Ser
                165                 170                 175

Leu Thr Asn Asp Ile Ile Ala Arg Ala Ala Phe Gly Glu Lys Cys Lys
            180                 185                 190

```
Asp Lys His Ala Phe Leu Ser Leu Ile Glu Glu Gly Ile Gln Leu Ala
            195                 200                 205
Gly Gly Phe Asp Ile Ala Gly Leu Phe Pro Ser Leu Lys Leu Leu His
210                 215                 220
Val Ile Thr Gly Lys Lys Arg Gln Leu Glu Arg Val His Asn Glu Leu
225                 230                 235                 240
Asp Arg Ile Leu Val Asp Ile Lys Glu Asn Lys Glu Lys Arg Arg
                245                 250                 255
Ala Ser Lys Leu Asn Glu Asp Lys Tyr Glu Glu Asn Leu Val Asp Val
            260                 265                 270
Leu Val Arg Val Gln Glu Asn Thr Gln Leu Glu Val Pro Leu Ala Asn
            275                 280                 285
Asp Asn Leu Lys Ala Val Ile Leu Asp Ile Phe Val Ala Gly Ser Glu
            290                 295                 300
Thr Ser Ser Thr Thr Ile Glu Trp Ala Met Ser Glu Met Leu Lys Asn
305                 310                 315                 320
Pro Lys Val Met Lys Ala Gln Ala Glu Val Arg Arg Val Phe Ser
                325                 330                 335
Gly Asn Lys Lys Ile Asn Glu Thr Glu Ile Gln Glu Leu Ser Tyr Leu
            340                 345                 350
Lys Leu Val Leu Lys Glu Thr Leu Arg Leu His Ala Pro Ala Pro Leu
            355                 360                 365
Leu Ile Pro Arg Glu Cys Arg Glu Ser Cys Glu Ile Asp Gly Tyr Glu
            370                 375                 380
Ile Pro Lys Lys Thr Met Val Met Val Asn Ala Trp Ala Ile Gly Arg
385                 390                 395                 400
Asp Pro Glu Asn Trp Ser Asn Gly Asp Arg Phe Glu Pro Glu Arg Phe
                405                 410                 415
Asp Gly Ile Ser Val Asp Tyr Lys Gly Thr Asn Phe Glu Tyr Ile Pro
            420                 425                 430
Phe Gly Ala Gly Arg Arg Ile Cys Pro Gly Met Leu Phe Gly Met Ala
            435                 440                 445
Asn Val Glu Val Pro Leu Ala Arg Leu Leu Tyr His Phe Asp Trp Glu
450                 455                 460
Leu Pro Asn Gly Ile Lys Pro Glu Glu Leu Asp Met Asp Glu Thr Phe
465                 470                 475                 480
Gly Thr Thr Val Arg Arg Lys Asn His Leu Tyr Leu Ile Pro Thr Val
                485                 490                 495
Val His Glu Leu Glu Arg Ser Thr Thr Lys Glu
            500                 505

<210> SEQ ID NO 16
<211> LENGTH: 519
<212> TYPE: PRT
<213> ORGANISM: Artificial Sequence
<220> FEATURE:
<223> OTHER INFORMATION: SEQ ID NO:16 CYP82D61

<400> SEQUENCE: 16

Met Asp Ser Leu His Cys Leu Glu Thr Leu Leu Leu Gly Phe Val
1               5                   10                  15
Leu Leu Pro Cys Phe Phe Tyr Phe Val Trp Lys Lys Pro Asn Asn Lys
                20                  25                  30
Ile Lys Glu Pro Pro Gln Pro Ala Gly Ala Trp Pro Ile Ile Gly His
            35                  40                  45
```

```
Leu His Leu Leu Ala Arg Gly Asp Leu Pro His Lys Ile Leu Ser Ser
 50                  55                  60

Phe Ala Asp Lys Asn Gly Pro Val Phe Lys Ile Gln Leu Gly Val His
 65                  70                  75                  80

Gln Ala Leu Val Val Asn Asn Ser Glu Ile Ala Lys Glu Cys Phe Thr
                     85                  90                  95

Thr Asn Asp Arg Phe Phe Leu Asn Arg Pro Ser Gly Val Ala Ala Lys
                100                 105                 110

Ile Met Gly Tyr Asn Tyr Val Met Leu Gly Val Ala Pro Tyr Gly Pro
                115                 120                 125

Tyr Trp Arg Asp Met Arg Lys Ile Ile Met Leu Glu Phe Leu Ser Asn
130                 135                 140

Arg Arg Leu Gln Ser Leu Lys His Val Trp His Ser Glu Ile Ser Ile
145                 150                 155                 160

Ser Ser Lys Glu Leu Tyr Lys Leu Trp Glu Thr Gln Asn Ile Asp Phe
                165                 170                 175

Cys Leu Val Asp Met Lys Gln Trp Leu Ala Asp Leu Thr Leu Asn Met
                180                 185                 190

Ser Val Lys Met Val Val Gly Lys Arg Phe Phe Gly Ser Ala Ser Ala
                195                 200                 205

Ser Ala Cys Glu Glu Thr Glu Ser Ser Asn Cys Pro Lys Thr Leu Arg
210                 215                 220

Asn Met Phe Arg Leu Met Gly Ser Phe Val Leu Ser Asp Tyr Leu Pro
225                 230                 235                 240

Tyr Leu Arg Trp Leu Asp Leu Gly Gly His Glu Lys Glu Met Lys Arg
                245                 250                 255

Thr Val Lys Glu Leu Asp Ile Leu Phe Lys Gly Trp Leu Asp Glu His
                260                 265                 270

Lys Arg Lys Arg Leu Ser Gly Gly Lys Glu Asp Asp Gln Asp Phe
                275                 280                 285

Met Asp Val Met Leu Ser Ile Leu Glu Glu Ser Lys Leu Gly Asn Asp
290                 295                 300

Val Asp Thr Ile Asn Lys Thr Ala Cys Leu Ala Ile Ile Leu Gly Gly
305                 310                 315                 320

Ala Asp Thr Thr Trp Ala Thr Leu Thr Trp Ala Leu Ser Leu Leu Leu
                325                 330                 335

Asn Asn Pro Asn Ala Leu Lys Lys Ala Gln Asp Glu Leu Asp Leu His
                340                 345                 350

Val Gly Arg Asp Arg Asn Val Asp Glu Ser Asp Leu Val Lys Leu Thr
                355                 360                 365

Tyr Ile Asp Ala Ile Ile Lys Glu Thr Leu Arg Leu Tyr Pro Pro Gly
370                 375                 380

Pro Leu Leu Gly Pro Arg Val Val Thr Glu Asp Cys Thr Ile Ala Gly
385                 390                 395                 400

Tyr His Val Arg Ala Gly Thr Arg Leu Ile Val Asn Ala Trp Lys Ile
                405                 410                 415

Gln Arg Asp Pro Leu Val Trp Ser Gln Pro His Glu Tyr Gln Pro Glu
                420                 425                 430

Arg Phe Leu Glu Arg Asp Val Asp Met Lys Gly Gln His Phe Glu Leu
                435                 440                 445

Ile Pro Phe Gly Ser Gly Arg Arg Ala Cys Pro Ala Ile Ser Leu Ala
                450                 455                 460

Leu Gln Val Leu Pro Leu Thr Leu Ala His Ile Leu His Gly Phe Glu
```

-continued

```
             465                 470                 475                 480

Leu Arg Thr Pro Asn Gln Asn Lys Val Asp Met Thr Glu Thr Pro Gly
                485                 490                 495

Ile Val His Ala Lys Ala Thr Pro Leu Glu Val Leu Val Ala Pro Arg
                500                 505                 510

Ile Ser Pro Lys Cys Phe Val
                515
```

COMPOSITIONS AND METHODS FOR PRODUCING PODOPHYLLOTOXIN DERIVATIVES

CROSS-REFERENCE TO RELATED APPLICATION

This application claims priority and other benefits from U.S. Provisional Patent Application Ser. No. 62/208,385 filed Aug. 21, 2015, entitled "Compositions and Methods For Producing Podophyllotoxin Derivatives." Its entire content is specifically incorporated herein by reference.

STATEMENT OF GOVERNMENT SUPPORT

This invention was made with Government support under contracts GM089985 and AT008321 awarded by the National Institutes of Health. The Government has certain rights in the invention.

INCORPORATION OF SEQUENCE LISTING

A computer readable form of the sequence listing, 05854 Seq List 2019, submitted via EFS-WEB, is herein incorporated by reference.

TECHNICAL FIELD OF THE INVENTION

The present invention relates to compositions and methods for biosynthetically producing podophyllotoxin intermediates and derivatives or molecules including enzymes and their equivalents involved in the biosynthetic production of podophyllotoxin intermediates and derivatives. The compositions include host cells that comprise at least one nucleic acid encoding an enzyme or its equivalent involved in the biosynthetic production of podophyllotoxin intermediates and derivatives.

BACKGROUND

Although numerous clinically used drugs derive from plant natural products, little is known about their biosynthetic genes, limiting the understanding of plant metabolism and preventing access to engineered hosts for their production (de Luca et al, 2012). In spite of the promise of genomics and synthetic biology, few plant biosynthetic pathways have been elucidated so far. Of those, only three have been successfully transferred to a heterologous host for current or future industrial production, namely artemisinic acid (Paddon et al., 2013), the benzylisoquinoline alkaloids (Thodey et al., 2014, DeLoache et al., 2015), and the monoterpenoid indole alkaloids, aka MIA (Brown et al., 2015; Qu et al., 2015). The paucity of information regarding plant biosynthesis is especially stark in comparison to the >700 bacterial and fungal natural product biosynthetic pathways that have been characterized so far (Cimermancic et al., 2014).

Podophyllotoxin, a lignan from the endangered medicinal plant Himalayan Mayapple (*Podophyllum hexandrum*), is a known precursor to the antineoplastic compound etoposide (Stahelin et al., 1991; Canel et al., 2000; Gordaliza et al., 2004). Although etoposide is on the World Health Organization's list of essential medicines, the only route for its production involves the isolation of (−)-podophyllotoxin from the Mayapple plant (Lata et al., 2009) and its subsequent multistep, semisynthetic conversion to etoposide. Each of these steps is required for its potent topoisomerase inhibitory activity, which is not present in podophyllotoxin.

Knowledge of a biosynthetic route would enable more facile access to etoposide, and potentially to natural and unnatural derivatives that would be difficult to produce synthetically.

It would be highly desirable to have a simplified and more direct route to etoposide and etoposide intermediaries that circumvents the need not only for the Mayapple cultivation, but also for the semisynthetic epimerization as well as demethylation that are currently required for production.

SUMMARY

Embodiments of the invention herein describe compositions and methods for the biosynthetic production of podophyllotoxin intermediates and derivatives including the etoposide aglycone, (−)-4'-desmethyl-epipodophyllotoxin, in host cells that include plant and non-plant cells. A podophyllotoxin derivative such as (−)-4'-desmethyl-epipodophyllotoxin can then be utilized in a final chemical step to produce the topomerase inhibitor etoposide and other etoposide-related compounds.

The host cells comprise one or more nucleic acids each encoding an enzyme or its equivalent involved in the biosynthetic production of podophyllotoxin intermediates and derivatives from a starting molecule. The present invention also relates to methods of producing podophyllotoxin intermediates and derivatives by culturing the host cells under conditions that promote expression and activity of the necessary enzymes that are involved in the biosynthetic production of podophyllotoxin intermediates and derivatives.

The above summary is not intended to include all features and aspects of the present invention nor does it imply that the invention must include all features and aspects discussed in this summary.

INCORPORATION BY REFERENCE

All publications and patent applications mentioned in this specification are herein incorporated by reference to the same extent as if each individual publication or patent application was specifically and individually indicated to be incorporated by reference.

DESCRIPTION OF THE DRAWINGS

The accompanying drawings illustrate embodiments of the invention and, together with the description, serve to explain the invention. These drawings are offered by way of illustration and not by way of limitation; it is emphasized that the various features of the drawings may not be to-scale.

FIG. 2 depicts transient expression of early (−)-podophyllotoxin biosynthetic genes in *N. benthamiana*. Transient expression of combinations of PLR, SDH and CYP719A23 in *N. benthamiana* leaves produces (−)-matairesinol (m/z=357) and (−)-pluviatolide (m/z=355), which are not normally observed in tobacco leaves (GFP only control).

Data bars indicate the mean ion abundance [(−)-mode]±1 standard deviation, based on three biological replicates. (+)-pinoresinol (m/z=357) and (−)-secoisolariciresinol (m/z=361, no authentic standard) are natively produced in *N. benthamiana* leaves. Metabolite extracts were treated with β-glucosidase before LC-MS analysis.

Figure 3:
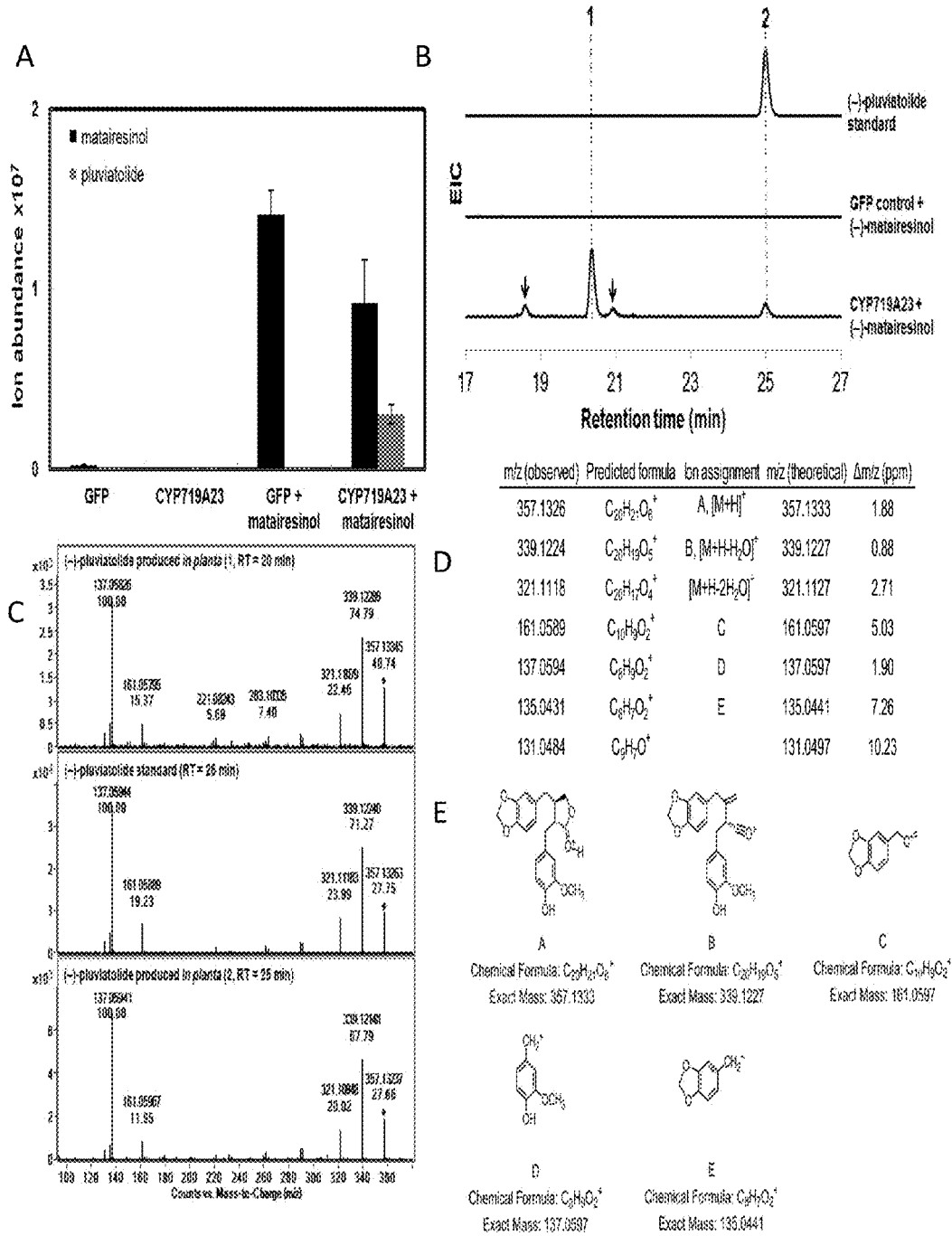

FIG. 3 shows that (−)-matairesinol infiltration enhances (−)-pluviatolide production in tobacco leaves expressing CYP719A23. (A) Infiltration of (−)-matairesinol (m/z=357) into *N. benthamiana* leaves transiently expressing CYP719A23 alone drastically increases (−)-pluviatolide (m/z=355) levels. No substrate infiltration and GFP only controls are shown for comparison. Data bars indicate the mean ion abundance [(−)-mode]±1 standard deviation, based on three biological replicates. (B) Extracted ion chromatograms (EIC) of (−)-pluviatolide (m/z=357) from the infiltration of (−)-matairesinol into *N. benthamiana* leaves transiently expressing CYP719A23 are shown and compared to GFP control and authentic standard [(+)-mode]; peaks observed at earlier labeled retention times (1 and arrows) are in-source fragments of (−)-pluviatolide derivatives that arise from modification of (−)-pluviatolide by endogenous tobacco enzymes. Only chromatograms from in planta experiments are to scale. (C) MS/MS (10 V) spectra of (−)- pluviatolide produced in planta (retention times, 1 and 2) compared to authentic standard [(+)-mode] (D) Table of MS/MS peak assignments and (E) putative ion structures.

Figure 4:
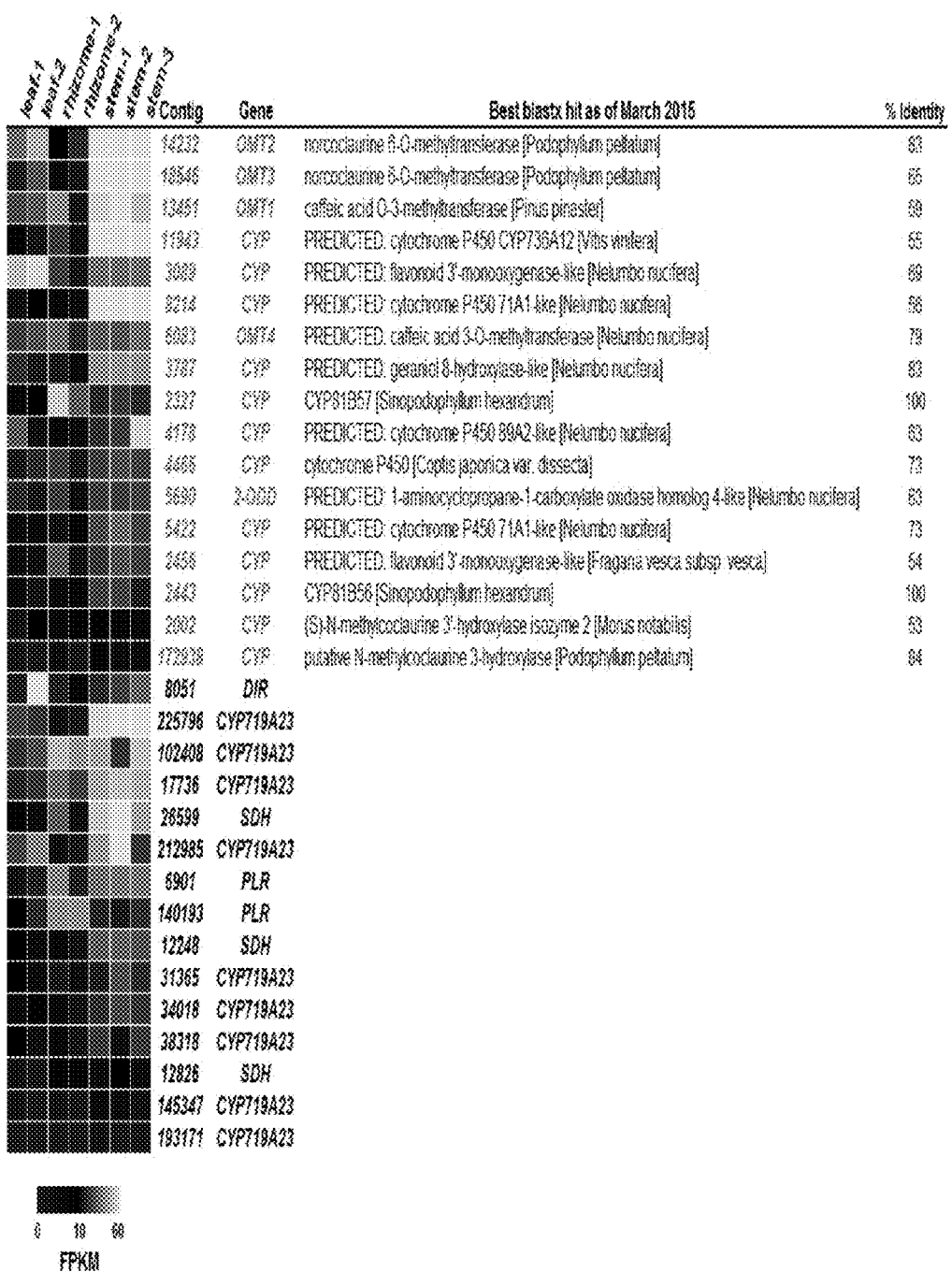

FIG. 4 depicts the candidate genes selected for initial screening from the Medicinal Plants Consortium *P. hexandrum* transcriptome. Candidates (grey and red) were chosen based on similar expression profiles to known (−)-podophyllotoxin biosynthetic genes (black), similarity to known enzymes involved in plant secondary metabolism based on best blastx hit, and percent identity and availability of full coding sequences. In red are (−)-podophyllotoxin biosynthetic genes that were discovered in this report. Multiple contigs were found to represent the same gene for known pathway enzymes. Contigs labeled CYP are distinct. Heat map shows FPKM (fragments per kilobase of transcript per million mapped reads) levels of transcripts.

Figure 5:
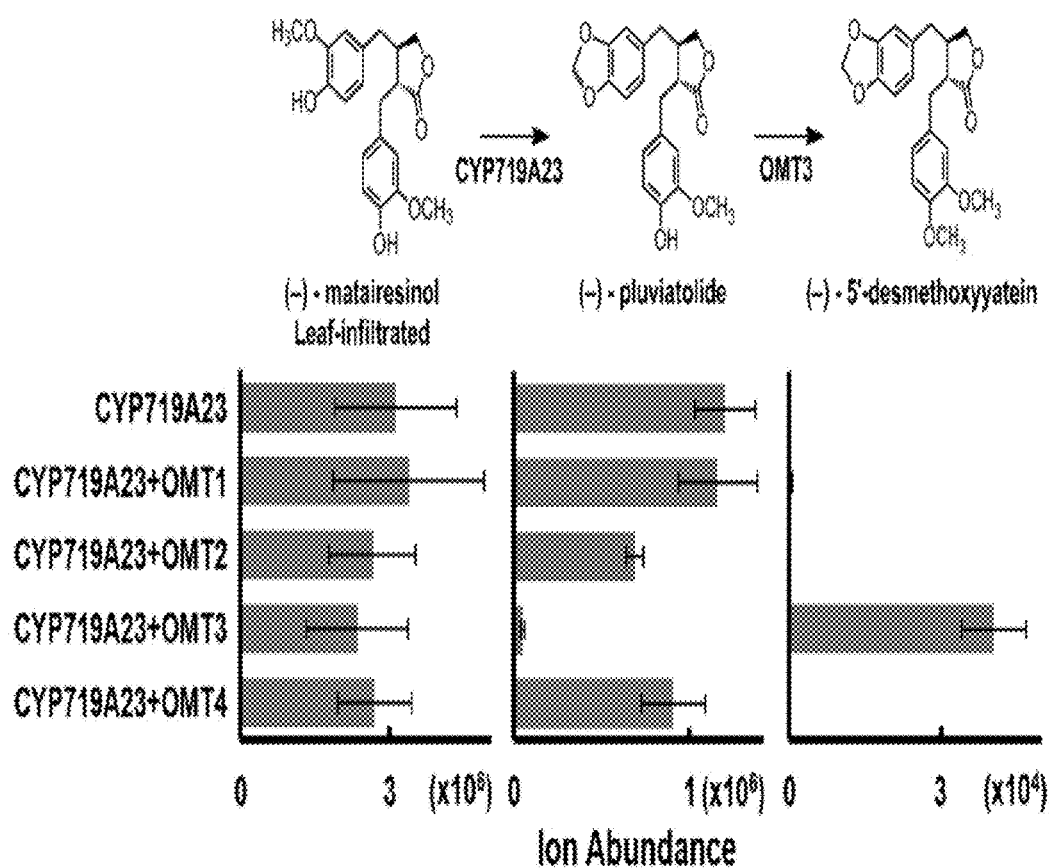

FIG. 5 depicts screening of OMT enzyme candidates in *N. benthamiana* by co-expression with CYP719A23 and (−)-matairesinol infiltration. Tobacco leaves expressing CYP719A23 individually with OMT candidates were infiltrated with (−)-matairesinol. Average LC-MS [(−)-mode] ion abundance ±one S.D. from three biological replicates of (−)-matairesinol and reaction products, (−)-pluviatolide and (−)-5'-desmethoxy-yatein are shown.

FIG. 6 shows that *N. benthamiana* transient expression of CYP719A23 and OMT3 and (−)- matairesinol infiltration produces (−)-5'-desmethoxy-yatein. (A) Aligned EICs of (−)-5'-desmethoxy-yatein [m/z=371, (+)-mode] from the transient expression of CYP719A23 and OMT3, compared to CYP719A23 alone, GFP alone and an authentic standard. Only chromatograms from in planta experiments are to scale. (B) MS/MS (10 V) spectra of (−)-5'-desmethoxyyatein produced in planta compared to authentic standard. (C) Table of MS/MS peak assignments and (D) putative ion structures.

Figure 7:
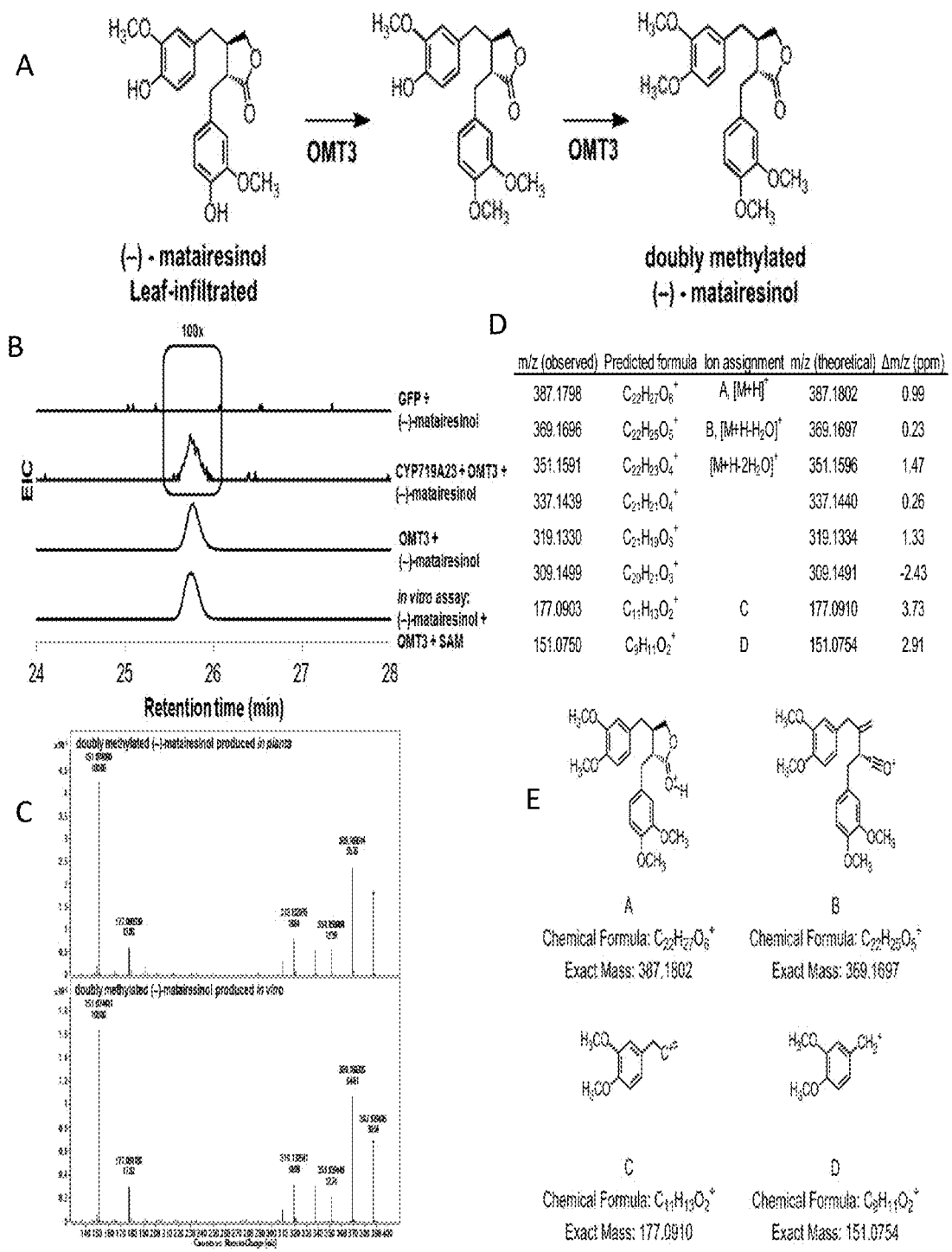

FIG. 7 depicts that *N. benthamiana* transient expression of CYP719A23 and OMT3 or OMT3 alone and (−)-matairesinol infiltration produces doubly methylated (−)-matairesinol. (A) Proposed reactions occurring in planta from the expression of OMT3 (B) Aligned EICs of the product [m/z=387, (+)-mode] from the transient expression of CYP719A23 and OMT3, compared to expression of OMT3 alone and GFP alone, and in vitro assay with purified OMT3 from *E. coli*, SAM and (−)-matairesinol. Only chromatograms from in planta expression of CYP719A23+OMT3 and GFP alone are to scale (approximately 100× magnified with respect to chromatogram from in planta expression of OMT3). (C) MS/MS (10 V) spectra of the product produced in planta compared to in vitro product formed by incubation of purified OMT3 from *E. coli*, SAM and (−)-matairesinol. (D) Table of MS/MS peak assignments and (E) putative ion structures.

FIG. 8 depicts the in vitro characterization of (−)-pluviatolide O-methyltransferase (OMT3). (A) Michaelis-Menten kinetic parameters were derived from initial rates of (−)-pluviatolide consumption by HPLC-DAD (280 nm) analysis with heterologously expressed and purified OMT3 from *E. coli*. Error bars represent the standard deviation from three independent assays. (B) HPLC-DAD (280 nm) profile of an in vitro reaction.

Figure 9:
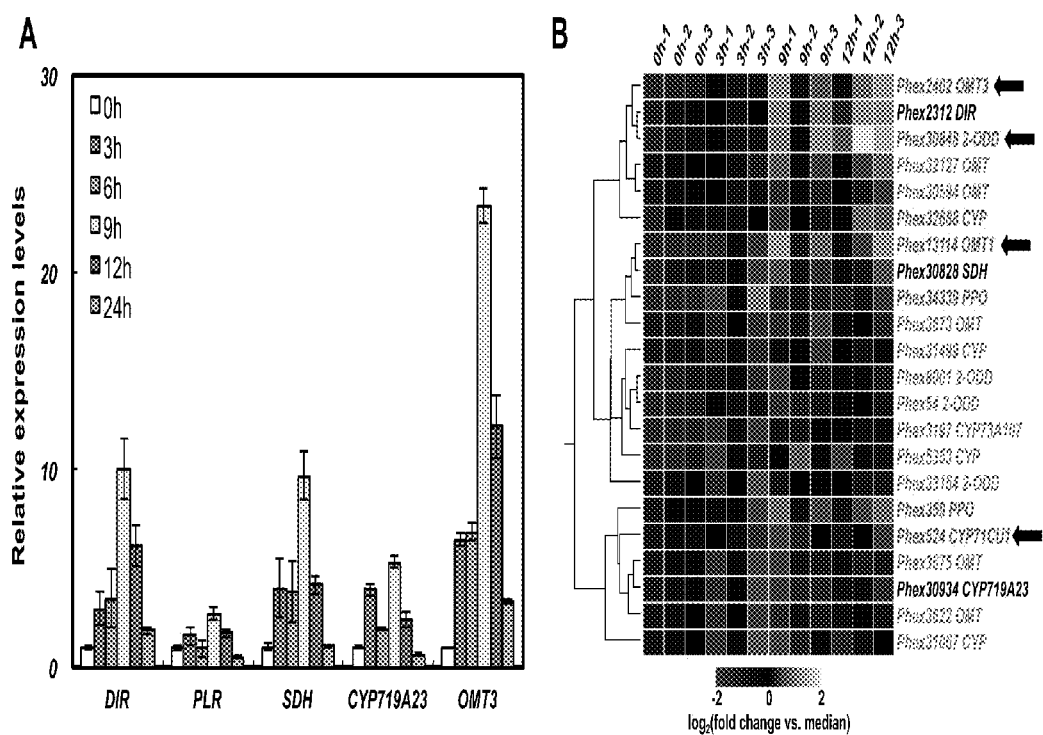

FIG. 9 depicts the elicitation of lignan biosynthetic genes by leaf wounding aids gene discovery. a) qRT-PCR gene expression analysis of OMT3 and other known podophyllotoxin biosynthetic genes after *P. hexandrum* leaf wounding. Relative expression levels were determined with respect to 0 h time point (before wounding). Data show average values (n=3 technical replicates)±one S.D. b) Hierarchical clustering performed on RNA-Seq expression data. RNA samples isolated before leaf wounding (0 h) and 3, 9 and 12 h after wounding from three biological replicates were sequenced. Clustering analysis was performed on de novo assembled transcripts of known (−)-podophyllotoxin genes and those that belong to gene families likely involved in the missing pathway steps: OMT, 0-methyltransferase; CYP, cytochrome P450; 2-ODD, 2-oxoglutarate/Fe(II)-dependent dioxygenase; PPO, polyphenol oxidase. Heat map depicts the expression levels (normalized read counts, log 2-scaled and median-centered) from a single node from the resulting cluster containing most of the known biosynthetic genes (black), genes discovered in this report (red with black arrows) and some of the additional candidates (red) that were screened. Normalized read counts less than 500 were removed to reduce the number of candidates depicted in this figure.

Figure 10:
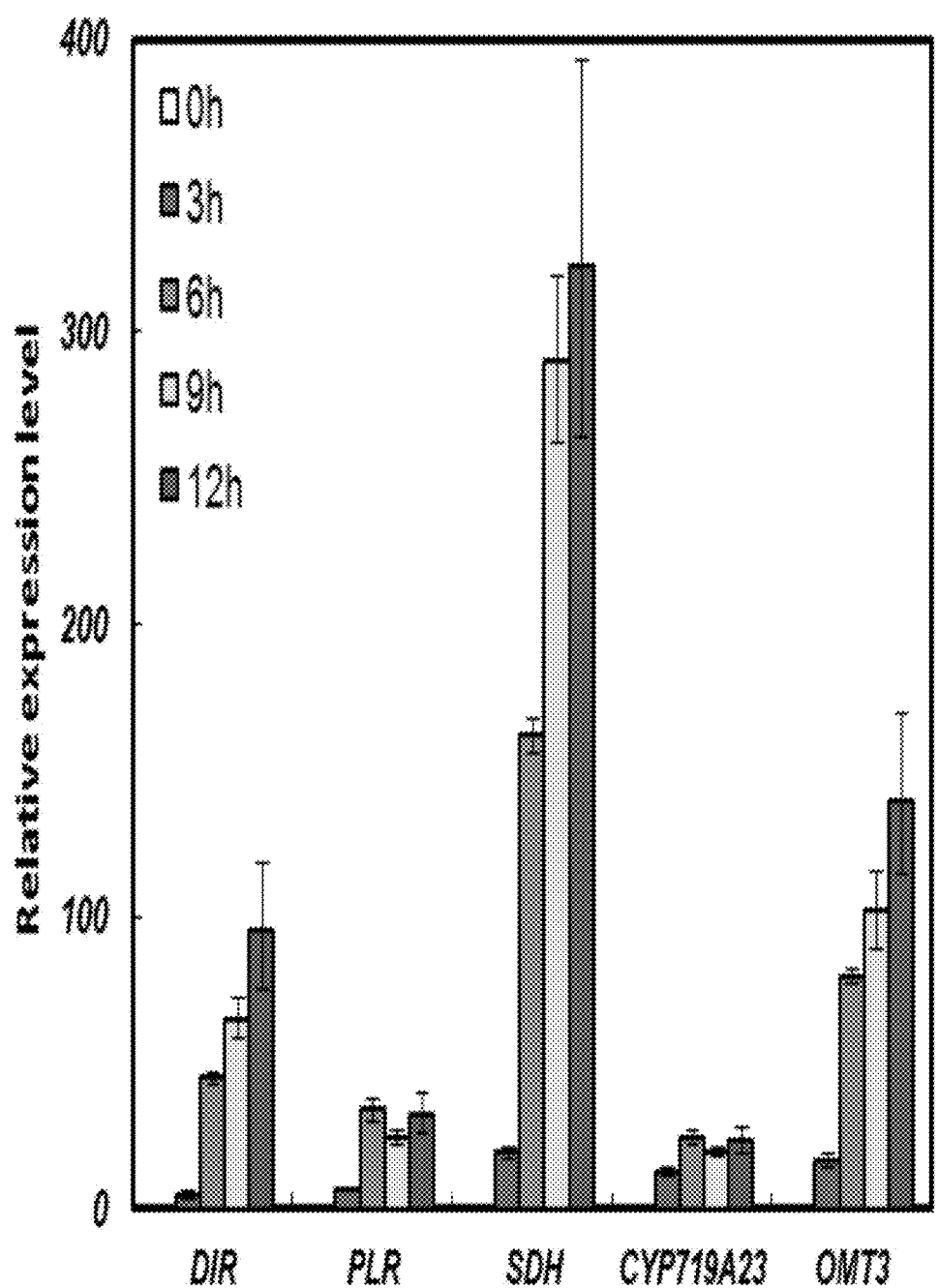

FIG. 10 depicts a gene expression profiling of a *P. hexandrum* leaf after wounding. qRT-PCR gene expression analysis of OMT3 and other known podophyllotoxin biosynthetic genes after *P. hexandrum* leaf wounding (biological replicate distinct from sample used in FIG. 3A). Relative expression levels were determined with respect to 0 h time point (before wounding). Data show average values (n=3 technical replicates)±one S.D.

Figure 11:
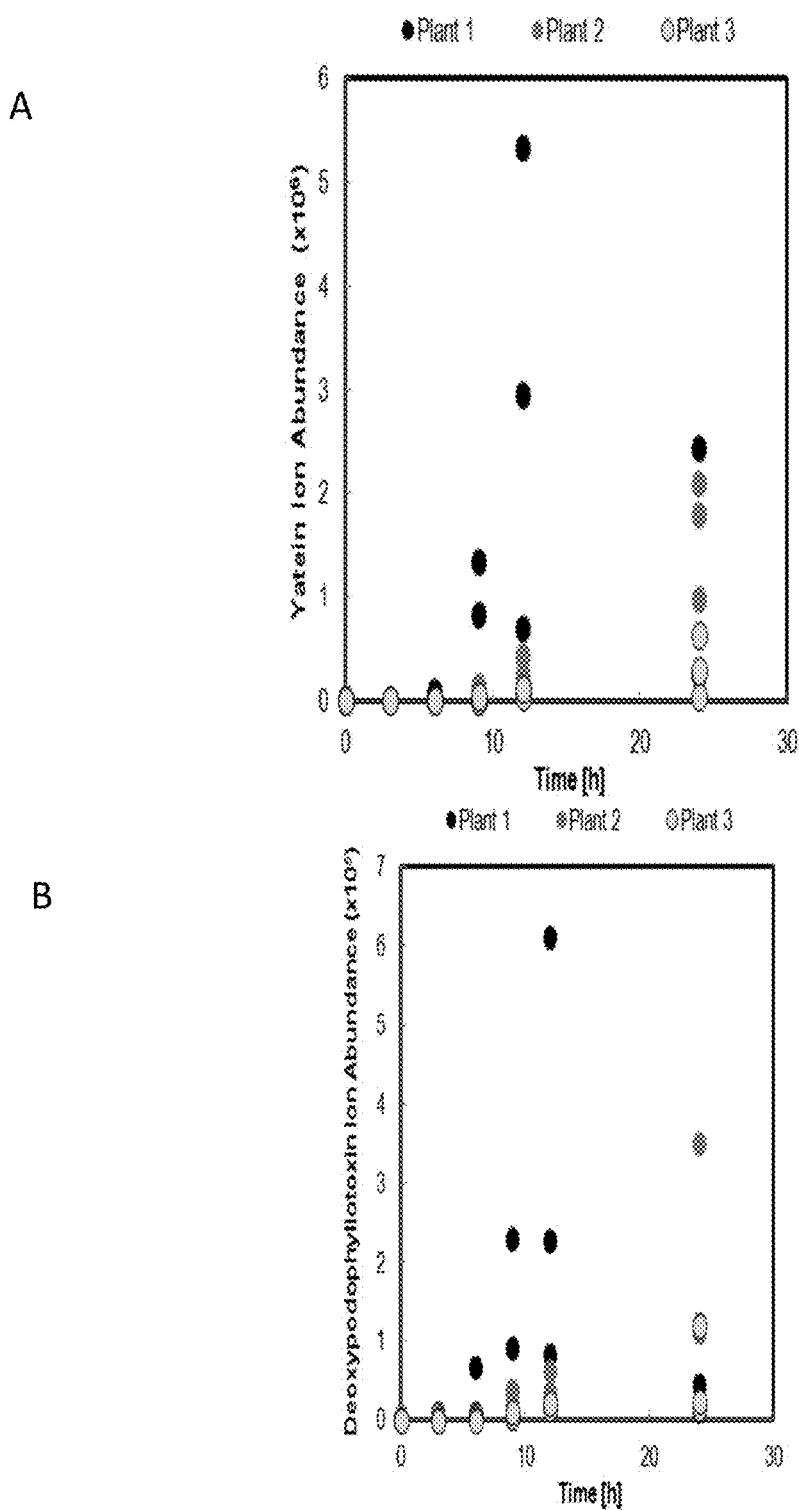

FIG. 11 depicts metabolite profiling of *P. hexandrum* leaves after wounding. *P. hexandrum* leaf wounding induces changes in lignan levels over time. Ion abundances [(+)-mode] are shown for triplicate samples from three plants for (A) (−)-yatein (m/z=401) and (B) (−)-deoxypodophyllotoxin (m/z=399). Plant 1 was used for qRT-PCR analysis (see results in FIG. 9A) and RNA Sequencing.

Figure 12:
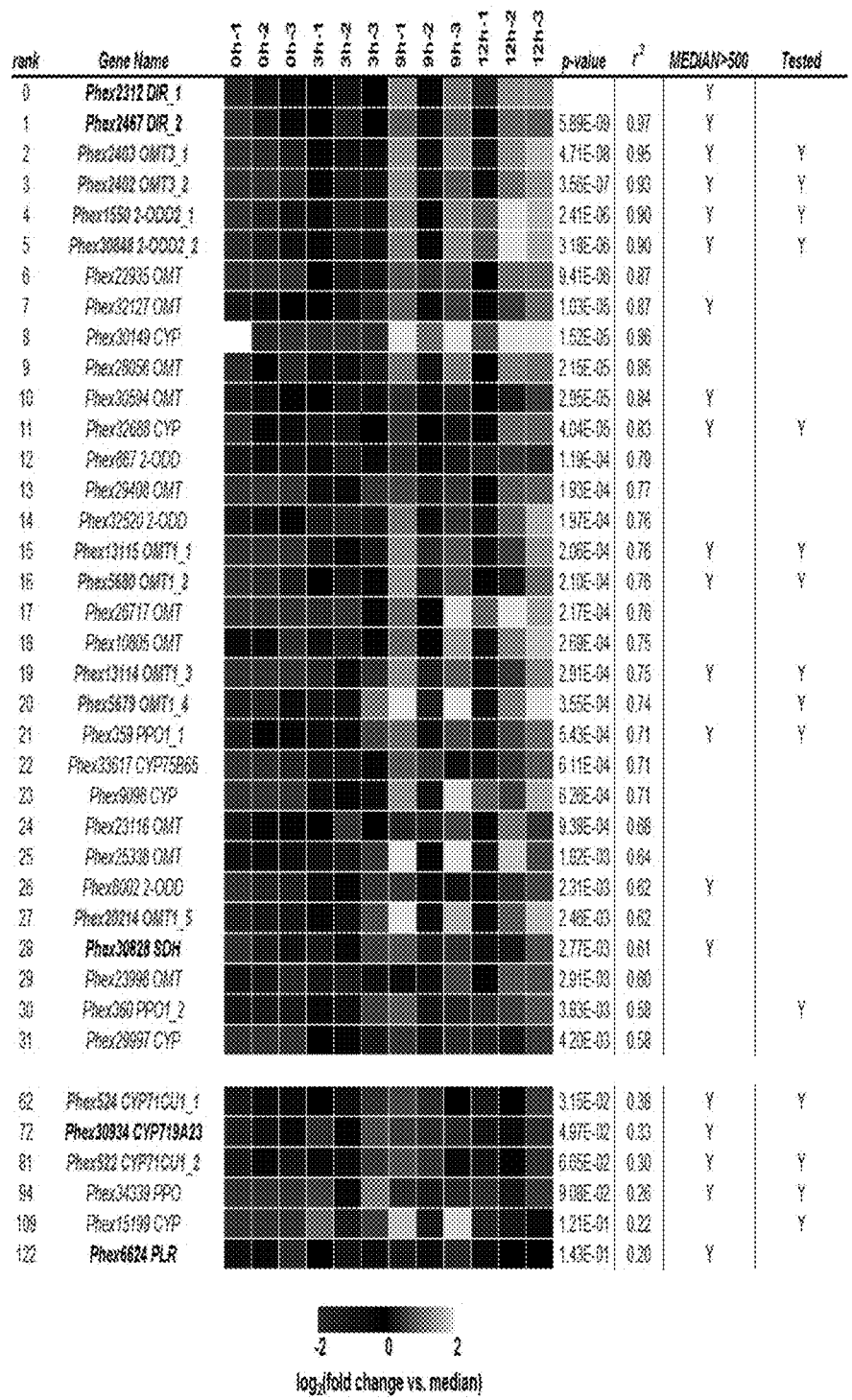

FIG. 12 depicts a co-expression analysis of *P. hexandrum* leaf RNA-Seq expression data after wounding using DIR as a bait gene. The top 31 ranked genes based on p-value from linear regression analysis were considered significant using the Benjamini-Hochberg procedure with a false discovery rate of 0.05 (multiple testing corrections). Other (−)-podophyllotoxin biosynthetic genes previously known (bold black) and discovered in this report (red), and other screened candidates based on co-expression analysis using CYP719A23 as the bait gene (non-bold black) are also displayed. Heat map depicts the expression levels (effective counts, TMM normalized, log$_2$-scaled and median-centered) after *P. hexandrum* leaf wounding. Candidate genes that were screened from this data were chosen based on co-expression with DIR and CYP719A23 (fig. S 11), and level of expression (TMM-normalized effective counts >500). Note that there are multiple contigs that represent the same gene.

Figure 13:
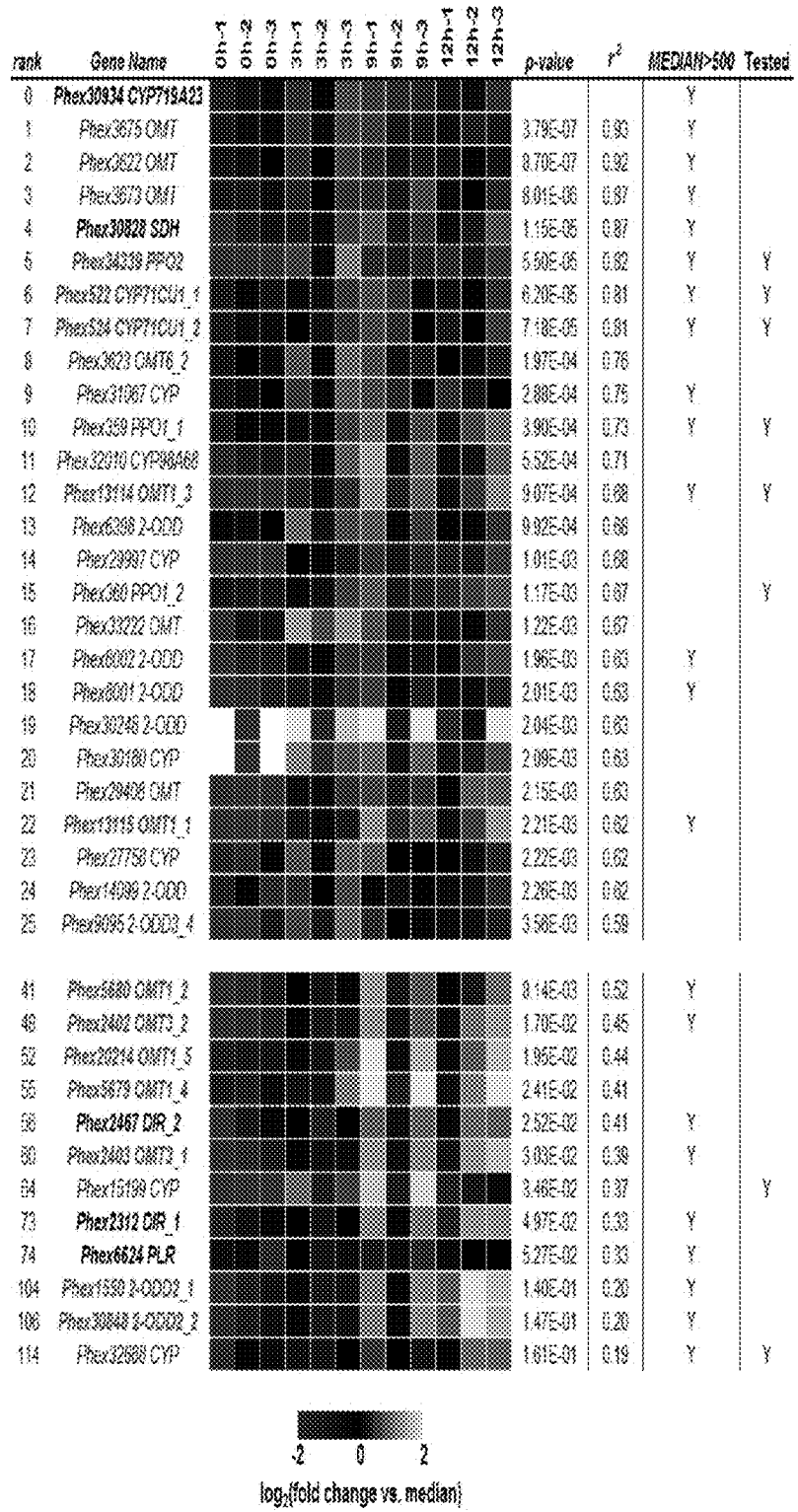

FIG. 13 shows a co-expression analysis of *P. hexandrum* leaf RNA-Seq expression data after wounding using CYP719A23 as a bait gene. The top 25 ranked genes based on p-value from linear regression analysis were considered significant using the Benjamini-Hochberg procedure with a false discovery rate of 0.05 (multiple testing corrections). Other (−)-podophyllotoxin biosynthetic genes previously known (bold black) and discovered in this report (red), and other screened candidates based on co-expression analysis using DIR as the bait gene (non-bold black) are also displayed. Heat map depicts the expression levels (effective counts, TMM normalized, log$_2$-scaled and median-centered) after *P. hexandrum* leaf wounding. Candidate genes that were screened from this data were chosen based on co-expression with DIR (fig. S10) and CYP719A23, and level of expression (TMM-normalized effective counts >500). Note that there are multiple contigs that represent the same gene.

FIG. 14 shows RNA-Seq expression profiles and metabolite data after leaf wounding of all known (−)-podophyllotoxin genes and genes discovered in this report. Each graph shows expression and metabolite data (dptox, deoxypodophyllotoxin) for individual leaflets from the same leaf after wounding. The expression and metabolite profiles are distinct for each set of data. Note that PLR was not significantly induced after leaf wounding. Expression profiles of Phex31052 (CYP) and Phex31132 (CYP) are also shown to demonstrate that not all genes are induced by wounding. Closest Arabidopsis homologs to Phex31052 and Phex31132 are CYP704A2 and CYP74B2 (hydroperoxide lyase), respectively.

Figure 15:
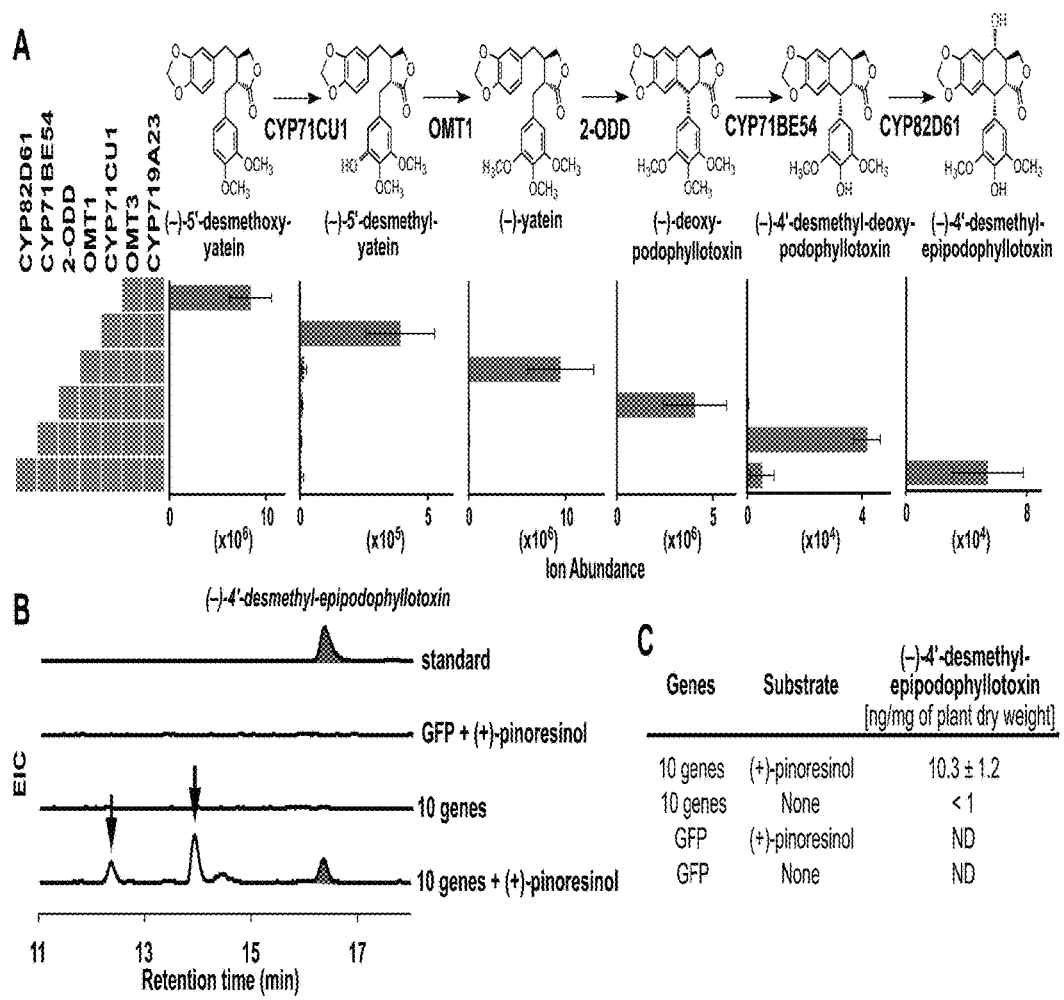

FIG. 15 shows the reconstitution of the *P. hexandrum* etoposide aglycone pathway in *N. benthamiana*. A) Tobacco leaves expressing different combinations of biosynthetic genes and infiltrated with (−)-matairesinol enabled the production of a number of lignan intermediates. Average LC-MS [(+)-mode] ion abundance±one S.D. from three biological replicates are shown. B) Extracted ion chromatograms (EIC) show the accumulation of the etoposide aglycone, (−)-4'-desmethyl-epipodophyllotoxin (m/z=401) in tobacco leaves expressing DIR, PLR, SDH, CYP719A23 and the six discovered enzymes in this report (10 genes total) with and without the infiltration of (+)-pinoresinol compared to a standard and tobacco leaves expressing GFP only. Endogenous tobacco activity gave rise to other (−)-4'-desmethyl-epipodophyllotoxin derivatives (arrows). C) Amount of (−)-4'-desmethyl-epipodophyllotoxin produced±one S.D. from three biological replicates. Derivatives were not quantified.

Figure 16:
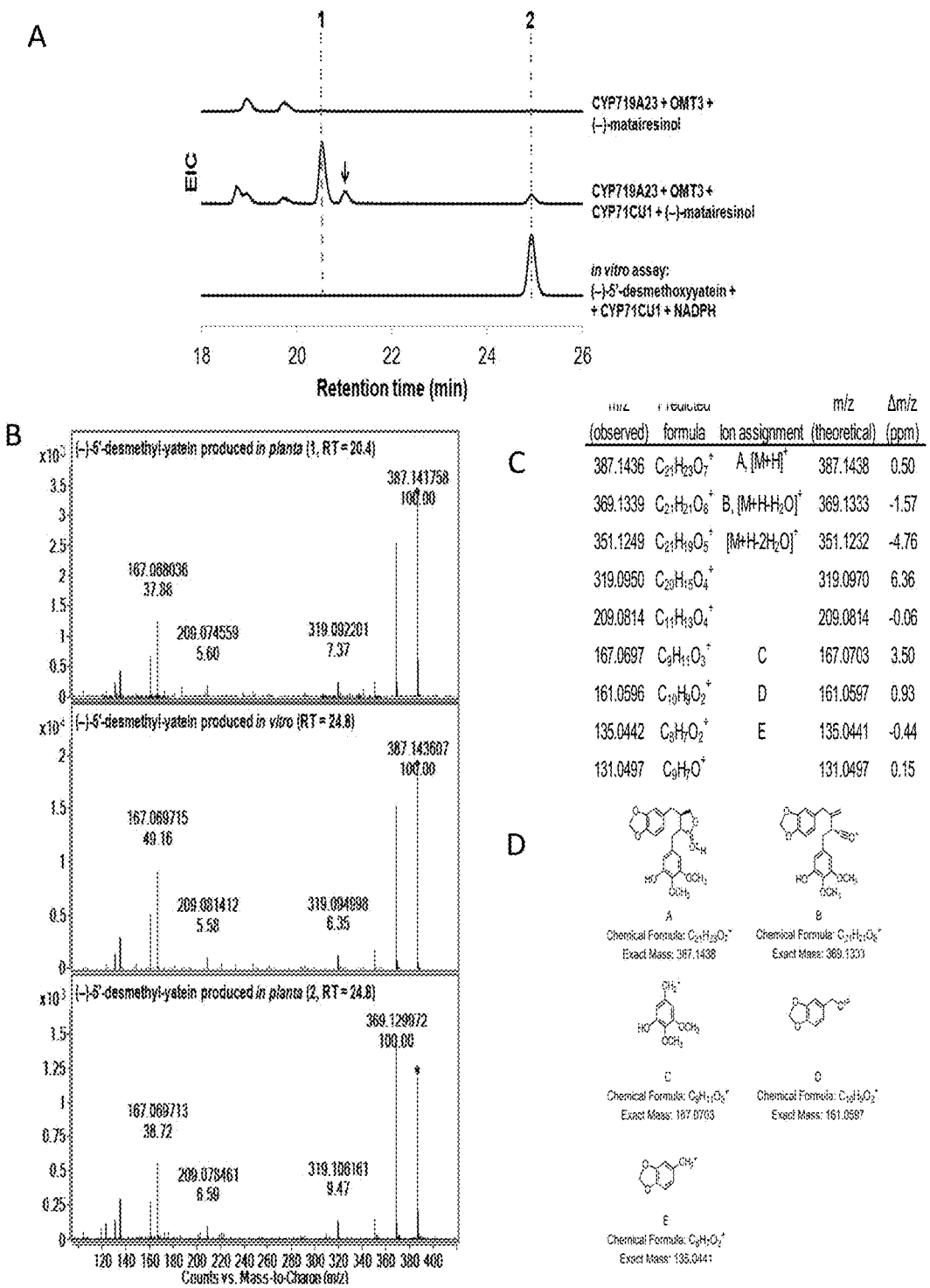

FIG. 16 depicts *N. benthamiana* transient expression of CYP719A23, OMT3, and CYP71CU1 and (−)-matairesinol leaf infiltration produces (−)-5'-desmethyl-yatein. (A) Aligned EICs of (−)-desmethyl-yatein [m/z=387, (+)-mode] from the transient expression of CYP719A23+OMT3+CYP71CU1, compared to CYP719A23+OMT3, and an in vitro assay with CYP71CU1-enriched microsomes, NADPH and (−)-5'-desmethoxy-yatein; peaks observed at earlier labeled retention times (1 and arrow) are likely in-source fragmentation ions of parent compounds that are a result of further modification of (−)-5'-desmethyl-yatein by endogenous tobacco enzymes. Only chromatograms from in planta experiments are to scale. (B) MS/MS (10 V) spectra of (−)-5'-desmethyl-yatein produced in planta (from labeled retention times, 1 and 2) compared to in vitro assay. (C) Table of MS/MS peak assignments and (D) putative ion structures.

Figure 17:
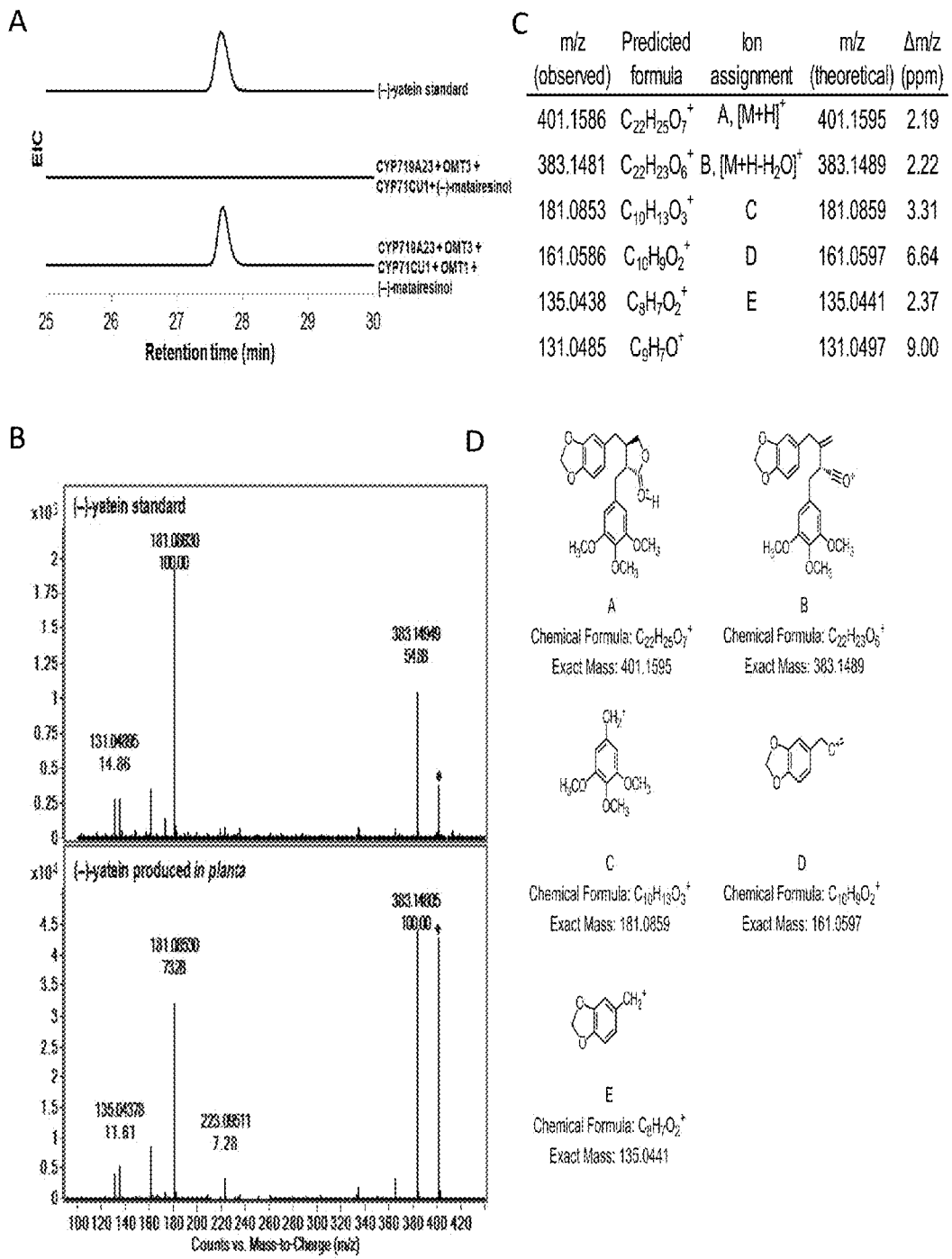

FIG. 17 depicts *N. benthamiana* transient expression of CYP719A23, OMT3, CYP71CU1, and OMT1 and (−)-matairesinol leaf infiltration produces (−)-yatein. (A) Aligned EICs of (−)-yatein [m/z=401, (+)-mode] from the transient expression of CYP719A23+OMT3+CYP71CU1+OMT1, compared to CYP719A23+OMT3+CYP71CU1 and an authentic standard. Only chromatograms from in planta experiments are to scale. (B) MS/MS (10 V) spectra of (−)-yatein produced in planta compared to authentic standard. (C) Table of MS/MS peak assignments and (D) putative ion structures.

Figure 18:
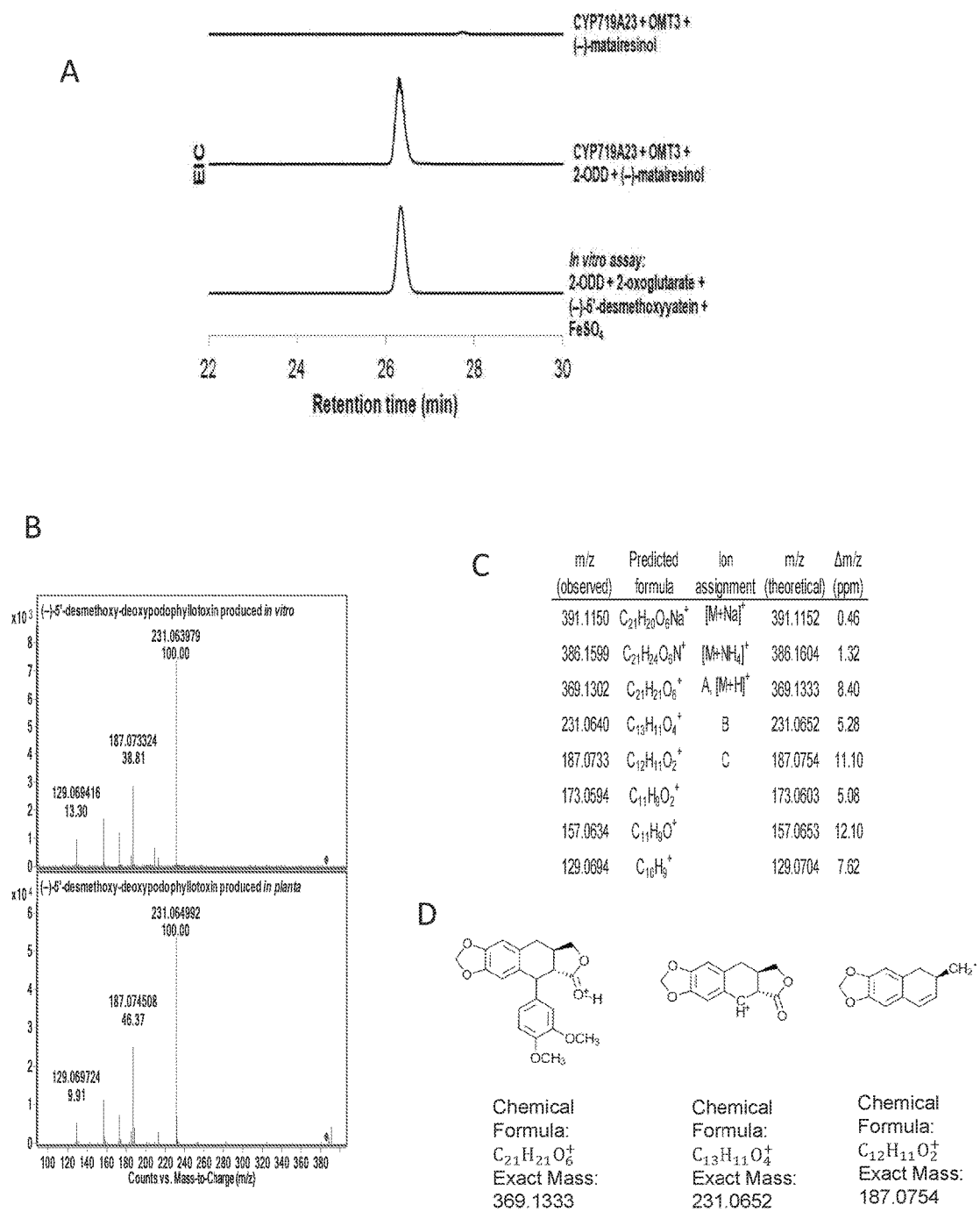

FIG. 18 depicts *N. benthamiana* transient expression of CYP719A23, OMT3 and 2-ODD and (−)-matairesinol leaf infiltration produces (−)-5'-desmethoxy-deoxypodophyllotoxin. (A) Aligned EICs of 5'-desmethoxy-deoxypodophyllotoxin (m/z=391, [M+Na]$^+$) from the transient expression of CYP719A23+OMT3+2-ODD, compared to CYP719A23+OMT3 and an in vitro assay with 2-ODD purified from *E. coli*, Fe2SO4, 2-oxoglutarate and (−)-5'-desmethoxy-yatein. Only chromatograms from in planta experiments are to scale. (B) MS/MS (20 V) spectra of (−)-5'-desmethoxydeoxypodophyllotoxin (m/z=386, [M+NH$_4$]+) produced in planta compared to in vitro product (C) Table of MS and MS/MS peak assignments and (D) putative ion structures.

FIG. 19 shows the proposed reaction mechanism of the conversion of (−)-yatein to (−)-deoxypodophyllotoxin catalyzed by 2-ODD. Oxygen is incorporated via hydroxylation of (−)-yatein at the 7' position, followed by its removal as water to form a quinone methide intermediate. Stereoselective cyclization then occurs, followed by removal of a proton to restore aromaticity, forming (−)-deoxypodophyllotoxin.

FIG. 20 depicts *N. benthamiana* transient expression of CYP719A23, OMT3, CYP71CU1, OMT1, and 2-ODD and (−)-matairesinol leaf infiltration produces (−)-deoxypodophyllotoxin. A) Aligned EICs of (−)-deoxypodophyllotoxin [m/z=399, (+)-mode] from the transient expression of CYP719A23+OMT3+CYP71CU1+OMT1+2-ODD, compared to CYP719A23+OMT3+CYP71CU1+OMT1 and an authentic standard. Only chromatograms from in planta experiments are to scale. (B) MS/MS (10 V) spectra of (−)-deoxypodophyllotoxin produced in planta compared to authentic standard (C) Table of MS/MS peak assignments and (D) putative ion structures.

FIG. 21 shows enzymatic assays of heterologously expressed CYP71CU1, OMT1 and 2-ODD. (A) Microsomal fractions containing CYP71CU1 were incubated with (−)-5'-desmethoxy-yatein [m/z=371, (+)-mode] and NADPH, forming (−)-5'-desmethyl-yatein [m/z=387]. CYP71CU1-microsomes and OMT1, expressed and purified from *E. coli*, were incubated with (−)-5'-desmethoxy-yatein, NADPH and SAM, forming (−)-yatein [m/z=401]. (−)-5'-desmethoxy-yatein co-elutes with (−)-yatein. (B) 2-ODD, expressed and purified from *E. coli*, was incubated with (−)-yatein, 2-oxoglutarate and FeSO4 to form (−)- deoxypodophyllotoxin. (C) The enzyme also had minor activity on (−)-5'-desmethoxy-yatein and almost negligible activity on (−)-pluviatolide under the same assay conditions. All chromatograms are to scale. Arrows point to products.

Figure 22:
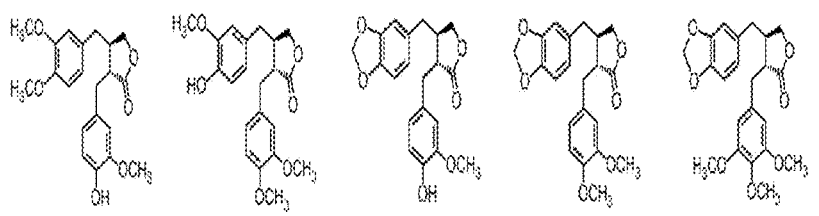

FIG. 22 shows the substrate specificity of OMT3, CYP71CU1, OMT1 and 2-ODD as determined by in vitro characterization. The table reports % activity of OMT3, CYP71CU1, OMT1 and 2-ODD as determined in vitro on a number of available lignan substrates. The % activity is determined with respect to the maximum conversion detected in all substrates tested. The results suggest that the order of events in the biosynthesis of (−)-4′-desmethyl-epipodophyllotoxin proceeds as depicted in FIG. 15. The predicted substrate for OMT1 is (−)-5′-desmethyl-yatein and was tested by incubation of OMT1 and SAM with (−)-5′-desmethoxy-yatein, CYP71CU1-microsomes isolated from WAT11 and NADPH to generate the substrate in vitro.

FIG. 23 depicts rhizome-specific candidate genes selected for screening from the Medicinal Plants Consortium *P. hexandrum* transcriptome. Candidate genes (grey and red) for enzymes involved in biosynthetic steps downstream of (−)-deoxypodophyllotoxin production were chosen based on rhizome-specific expression and the availability of full coding sequences. CYPs were chosen for hydroxylating activity on (−)-deoxypodophyllotoxin and NADP(H)-dependent oxidoreductases (NADP) were chosen for oxidative and reductive activity to epimerize (−)-epipodophyllotoxin to (−)-podophyllotoxin. In red are lignan biosynthetic genes that were discovered and characterized in this report. Heat map shows FPKM (fragments per kilobase of transcript per million mapped reads) levels of transcripts.

Figure 24:
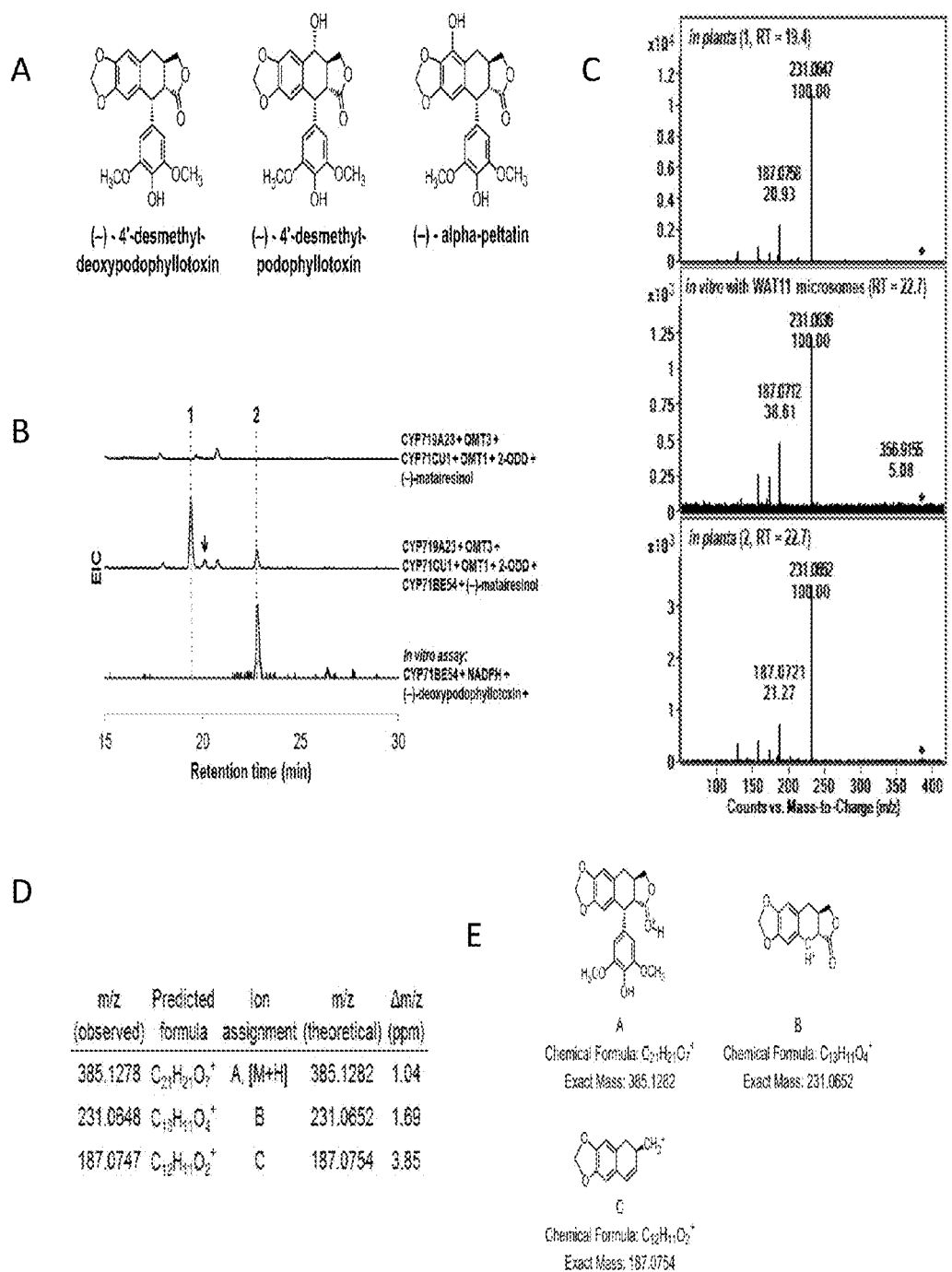

FIG. 24 depicts *N. benthamiana* transient expression of CYP719A23, OMT3, CYP71CU1, OMT1, 2-ODD and CYP71BE54, and (−)- matairesinol infiltration produces (−)-4′-desmethyl-deoxypodophyllotoxin. (A) Known 4′-desmethyl lignans present in *P. hexandrum*. (B) Aligned EICs of the product [m/z=385, (+)-mode] from the transient expression of CYP719A23+OMT3+CYP71CU1+OMT1+2-ODD+CYP71BE54, compared to CYP719A23+OMT3+CYP71CU1+OMT1+2-ODD, and in vitro assay with CYP71BE54-enriched microsomes, NADPH and (−)-deoxypodophyllotoxin; peaks observed at earlier labeled retention times (1 and arrow) are in-source fragmentation ions from parent peaks derived from (−)-4′-desmethyl-deoxypodophyllotoxin by further modification by endogenous tobacco enzymes. Only chromatograms from in planta expression are to scale. (C) MS/MS spectra (10 V) of (−)-4′-desmethyldeoxypodophyllotoxin produced in planta (from labeled retention times, 1 and 2); ion abundance of in vitro product formed by incubation of (−)-deoxypodophyllotoxin with CYP71BE54-enriched microsomes was too low to obtain a MS/MS spectrum. (D) Table of MS/MS peak assignments and (E) and putative ion structures.

Figure 25:
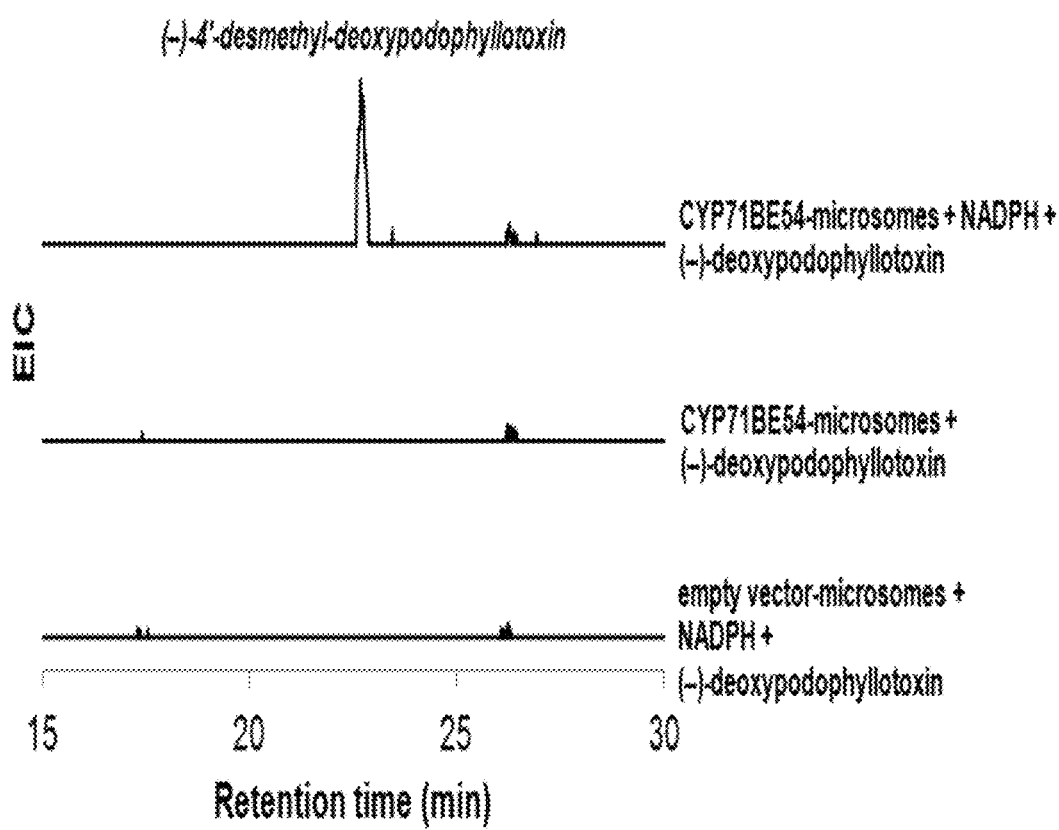

FIG. 25 depicts enzymatic assays of CYP71BE54-enriched microsomal fractions isolated from WAT11. Microsomal fractions containing CYP71BE54 were incubated with (−)-deoxypodophyllotoxin and NADPH, forming (−)-4′-desmethyl-deoxypodophyllotoxin [m/z=385, (+)-mode]. Aligned EICs are shown and are all to scale. Enzyme assays lacking NADPH or containing microsomes isolated from WAT11 harboring empty vector served as negative controls. No activity was observed on (−)-podophyllotoxin, (−)-5′-desmethoxy-yatein or (−)-yatein.

Figure 26:
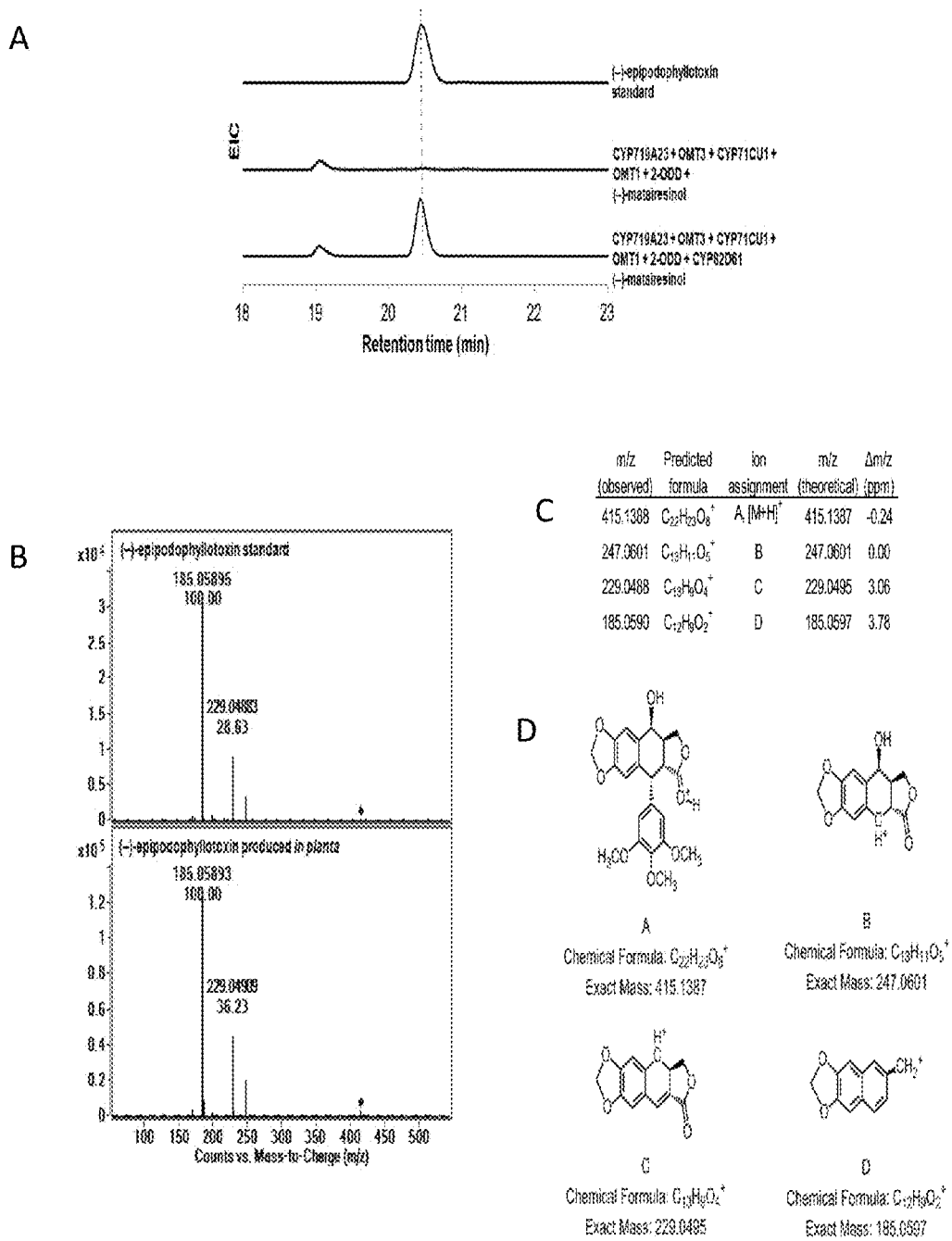

FIG. 26 shows *N. benthamiana* transient expression of CYP719A23, OMT3, CYP71CU1, OMT1, 2-ODD and CYP82D61, and (−)-matairesinol infiltration produces epipodophyllotoxin. (A) Aligned EICs of epipodophyllotoxin [m/z=415, (+)-mode] from the transient expression of CYP719A23+OMT3+CYP71CU1+OMT1+2-ODD+CYP82D61, compared to CYP719A23+OMT3+CYP71CU1+OMT1+2-ODD and an authentic standard. Only chromatograms from in planta expression are to scale. Interestingly, no modification by endogenous tobacco enzymes is observed, despite the introduction of a free hydroxyl. (B) MS/MS spectra (10 V) of epipodophyllotoxin produced in planta compared to authentic standard. (C) Table of MS/MS peak assignments and (D) putative ion structures.

Figure 27:
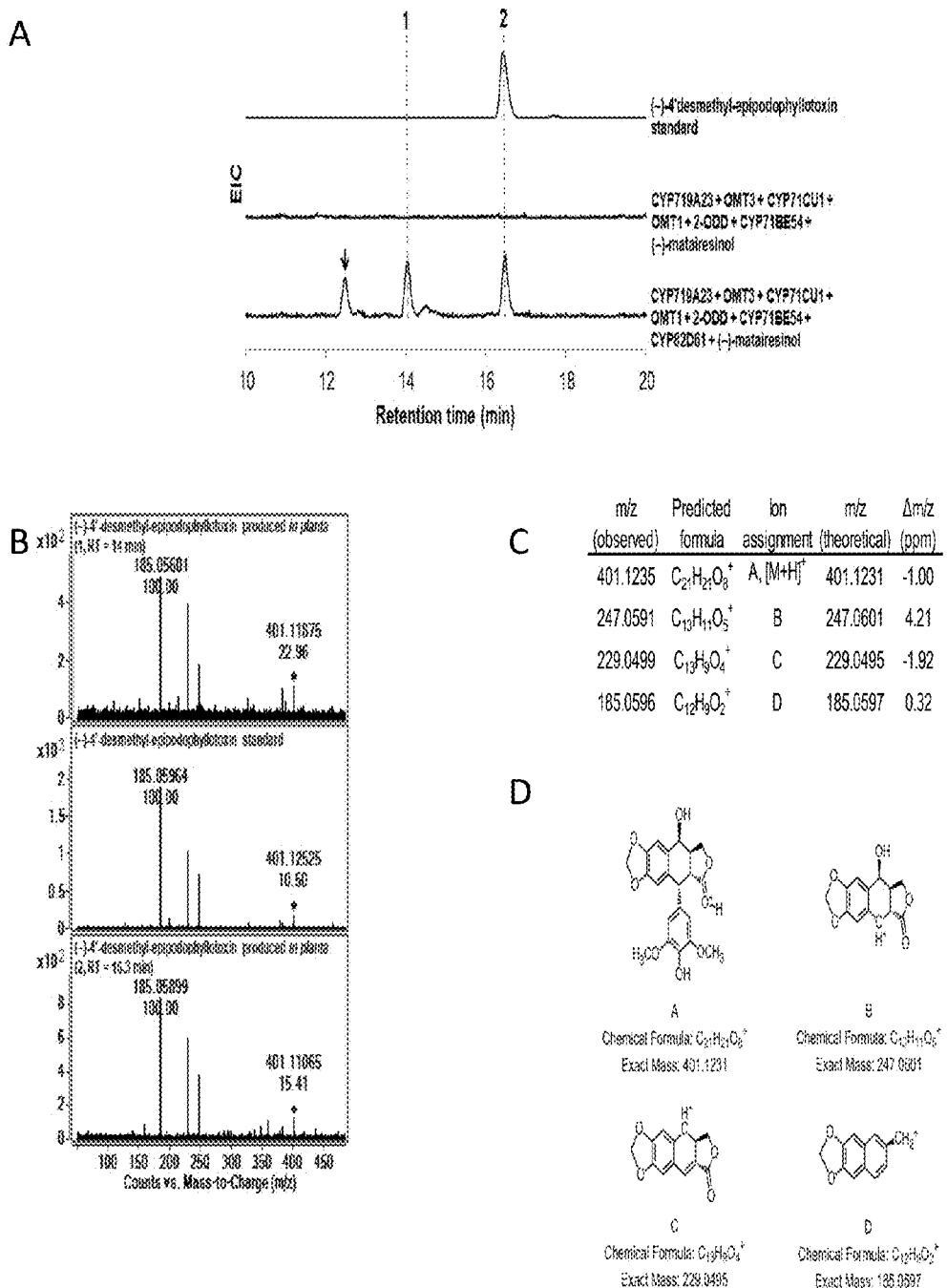

FIG. 27 depicts *N. benthamiana* transient expression of CYP719A23, OMT3, CYP71CU1, OMT1, 2-ODD, CYP71BE54 and CYP82D61, and (−)-matairesinol infiltration produces (−)-4′-desmethyl-epipodophyllotoxin, the etoposide alglycone. (A) Aligned EICs of 4′-desmethyl-epipodophyllotoxin [m/z=401, (+)-mode] from the transient expression of CYP719A23+OMT3+CYP71CU1+OMT1+2-ODD+CYP71BE54+CYP82D61, compared to CYP719A23+OMT3+CYP71CU1+OMT1+2-ODD+CYP71BE54 and an authentic standard; peaks observed at earlier labeled retention times (1 and arrow) are from further modification by endogenous tobacco enzymes. Only chromatograms from in planta expression are to scale. (B) MS/MS spectra (5 V) of 4′-desmethyl-epipodophyllotoxin produced in planta (from labeled retention times, 1 and 2) compared to authentic standard (C) Table of MS/MS peak assignments and (D) putative ion structures.

Figure 28:
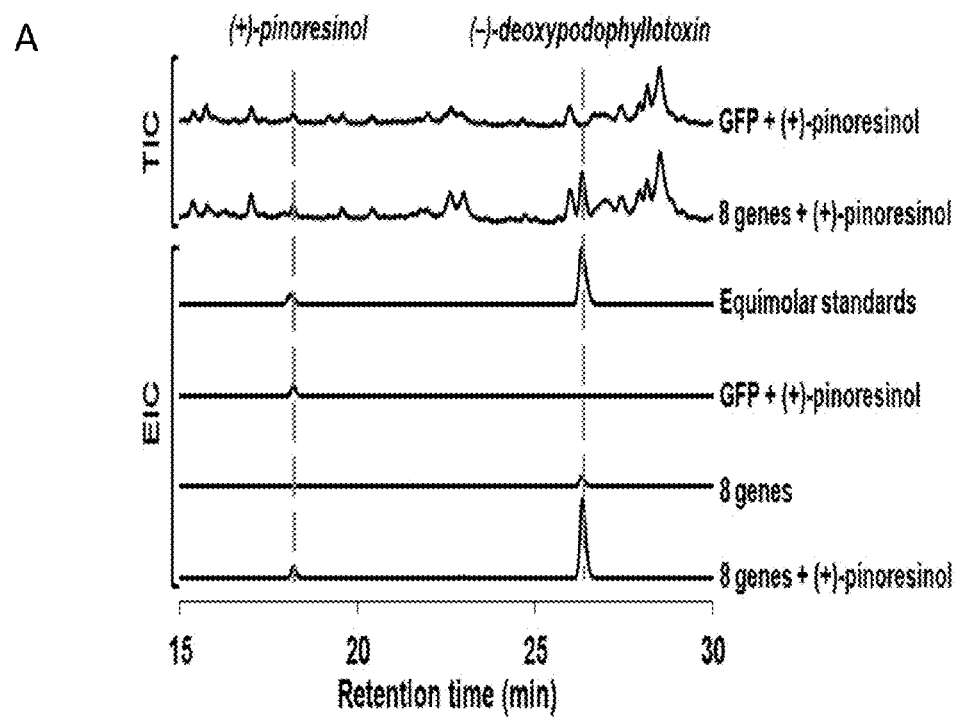

FIG. 28 depicts in planta reconstitution of (−)-deoxypodophyllotoxin biosynthesis from (+)-pinoresinol. (A) Total ion chromatogram (TIC) and combined extracted ion chromatograms (EIC) for (+)-pinoresinol (m/z=341, $[M-H_2O]^+$) and (−)-deoxypodophyllotoxin (m/z=399) are compared between the in planta expression of GFP with (+)-pinoresinol infiltration and the in planta expression of DIR, PLR, SDH, CYP719A23, OMT3, CYP71CU1, OMT1, and 2-ODD (8 genes) with and without (+)-pinoresinol infiltration. An equimolar standard (10 μM) of (+)-pinoresinol and (−)-deoxypodophyllotoxin is shown. (B) Amounts of (−)-deoxypodophyllotoxin produced in planta were quantified using a standard curve constructed from an authentic standard. Standard deviation is based on three biological replicates.

Figure 29:
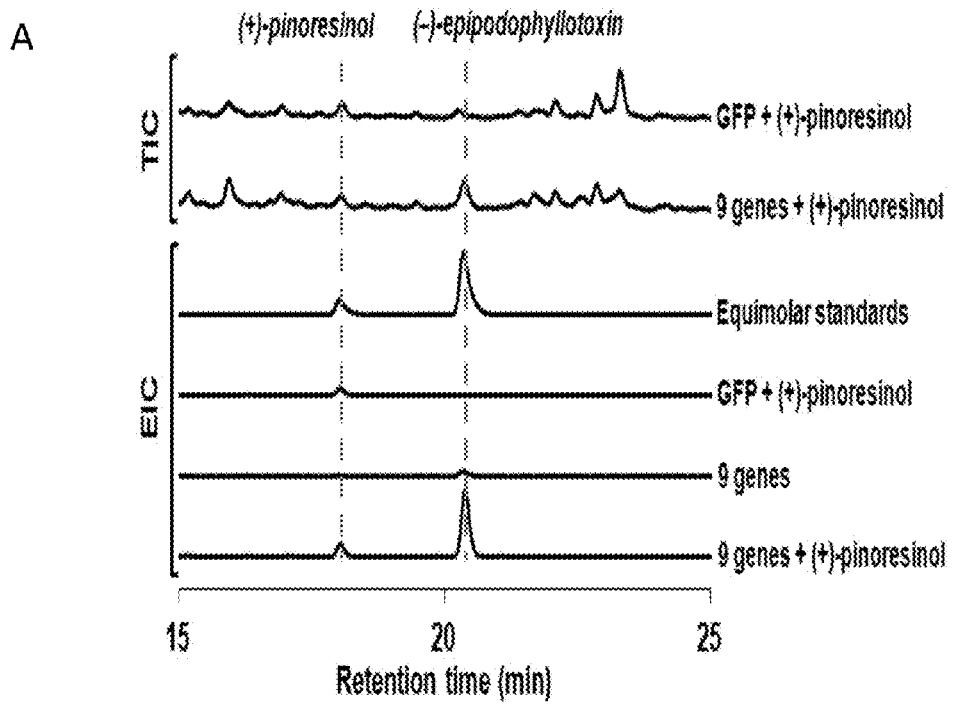

FIG. 29 depicts in planta reconstitution of (−)-epipodophyllotoxin biosynthesis from (+)-pinoresinol. (A) Total ion chromatogram (TIC) and combined extracted ion chromatograms (EIC) for (+)-pinoresinol (m/z=341, $[M-H_2O]^+$) and (−)-epipodophyllotoxin (m/z=415) are compared between the in planta expression of GFP with (+)-pinoresinol infiltration and the in planta expression of DIR, PLR, SDH, CYP719A23, OMT3, CYP71CU1, OMT1, 2-ODD, and CYP82D61 (9 genes) with and without (+)-pinoresinol infiltration. An equimolar standard (10 μM) of (+)-pinoresinol and (−)-epipodophyllotoxin is shown. (B) Amounts of (−)-epipodophyllotoxin produced in planta were quantified using a standard curve constructed from an authentic standard. Standard deviation is based on three biological replicates.

FIG. 30 depicts the ion abundance of intermediates from in planta reconstitution of (−)-epipodophyllotoxin and (−)-4′-desmethyl-epipodophyllotoxin biosynthesis from (+)-pinoresinol. (A) Ion abundance of intermediates from the reconstitution of (−)-epipodophyllotoxin biosynthesis from (+)-pinoresinol [PR] with and without PR infiltration compared to GFP with PR infiltration. (B) Ion abundance of intermediates from the reconstitution of (−)-4′-desmethyl-epipodophyllotoxin biosynthesis from PR with and without PR infiltration compared to GFP with PR infiltration. In both cases, ion abundances of intermediates are significantly less than the maximum amount observed to accumulate when the intermediates are produced as final products as in FIG. 15A.

Figure 31:
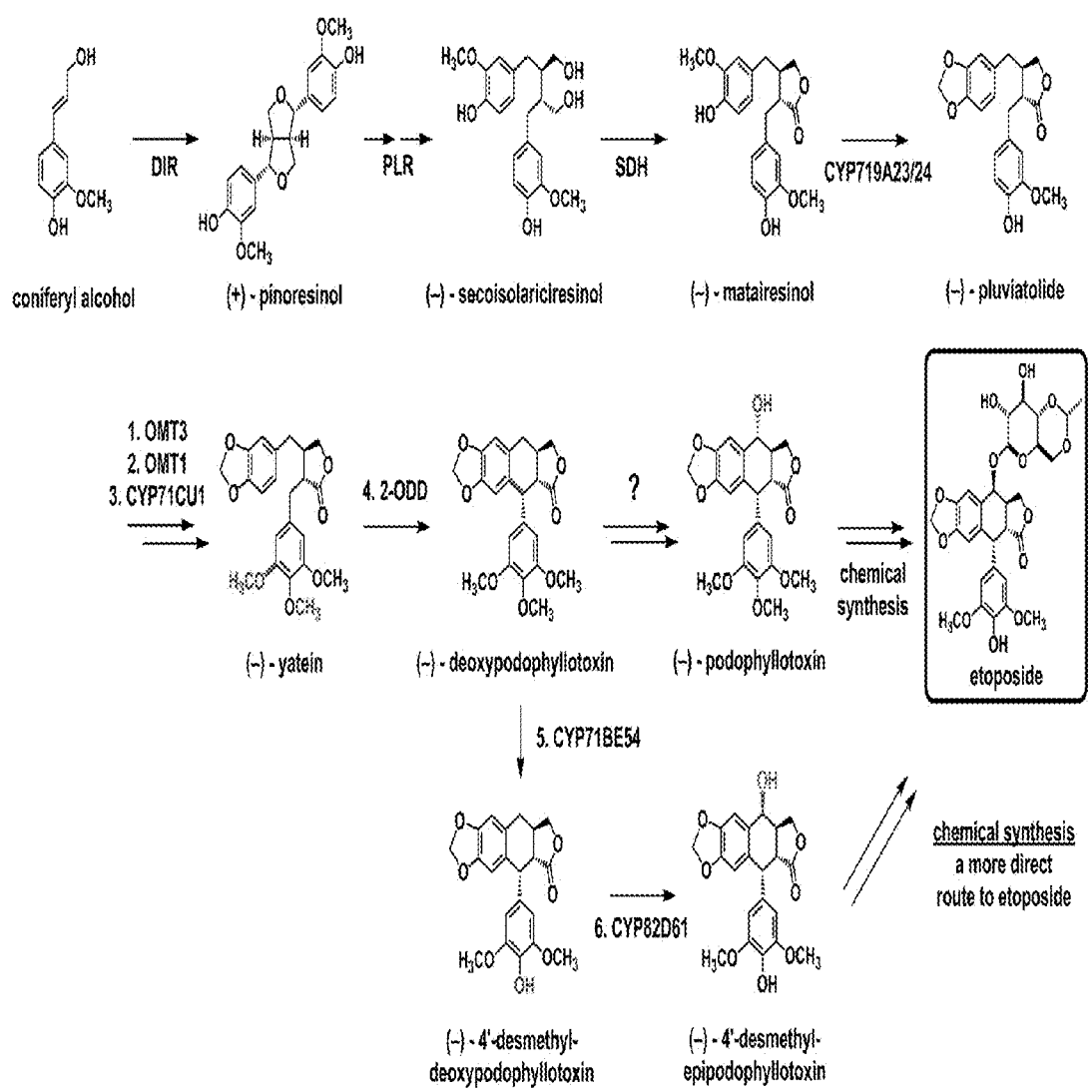

FIG. 31 depicts the biosynthetic route to (−)-4′-desmethyl-epipodophyllotoxin, the etoposide aglycone. The discovery of the six enzymes in this report (OMT3, CYP71CU1, OMT1, 2-ODD, CYP71BE54 and CYP82D61) enables the production of (−)-4′-desmethyl-epipodophyllotoxin, the etoposide alygcone, in a heterologous host such as *N. benthamiana*. This maps a simpler and more direct route to etoposide that circumvents the semisynthetic epimerization and demethylation currently required for etoposide production from (−)-podophyllotoxin isolated from Mayapple.

Figure 32:
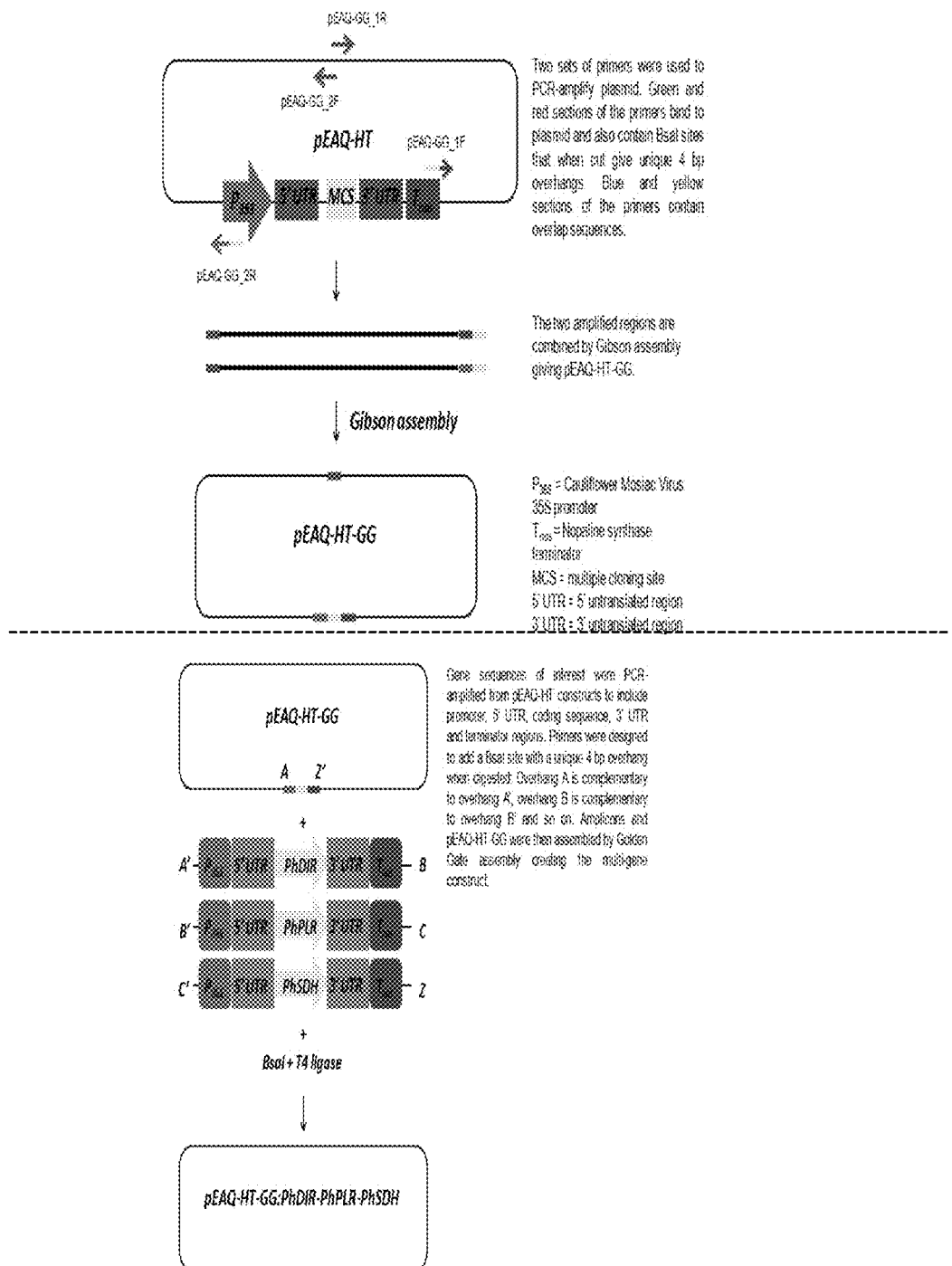
Figure 34A:
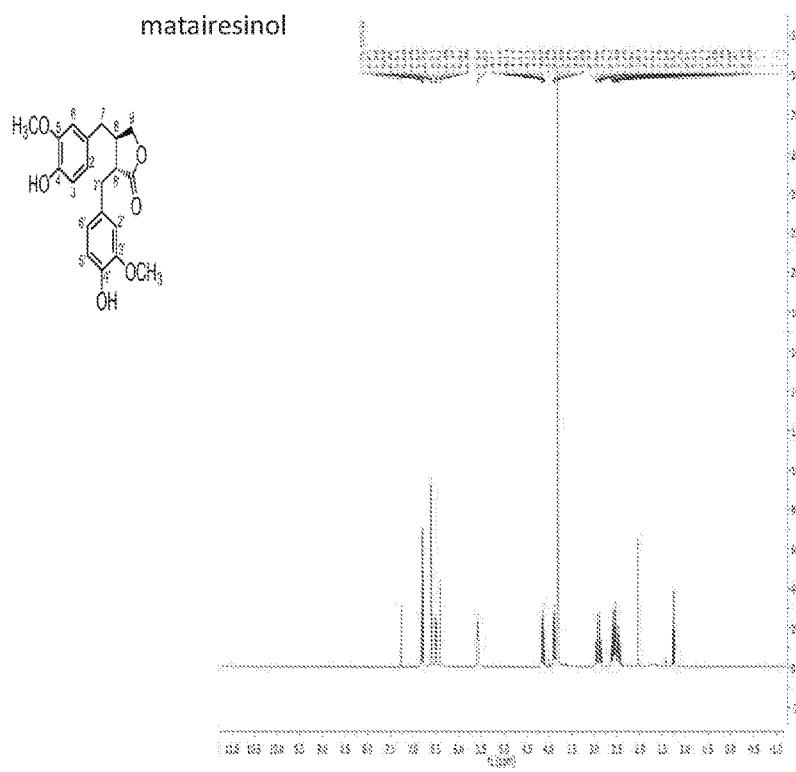
Figure 34B:
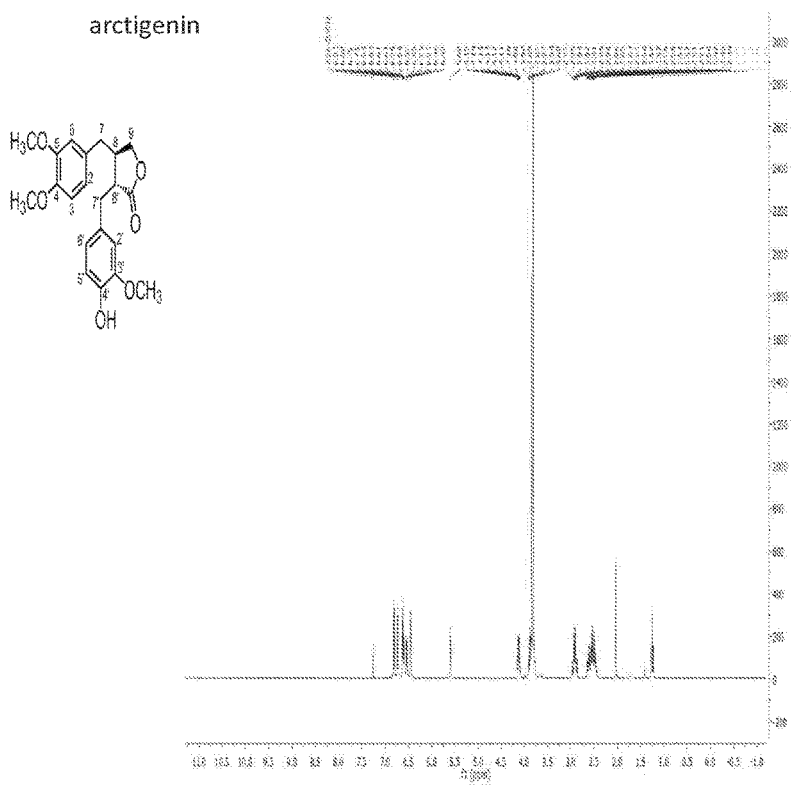
Figure 34C:
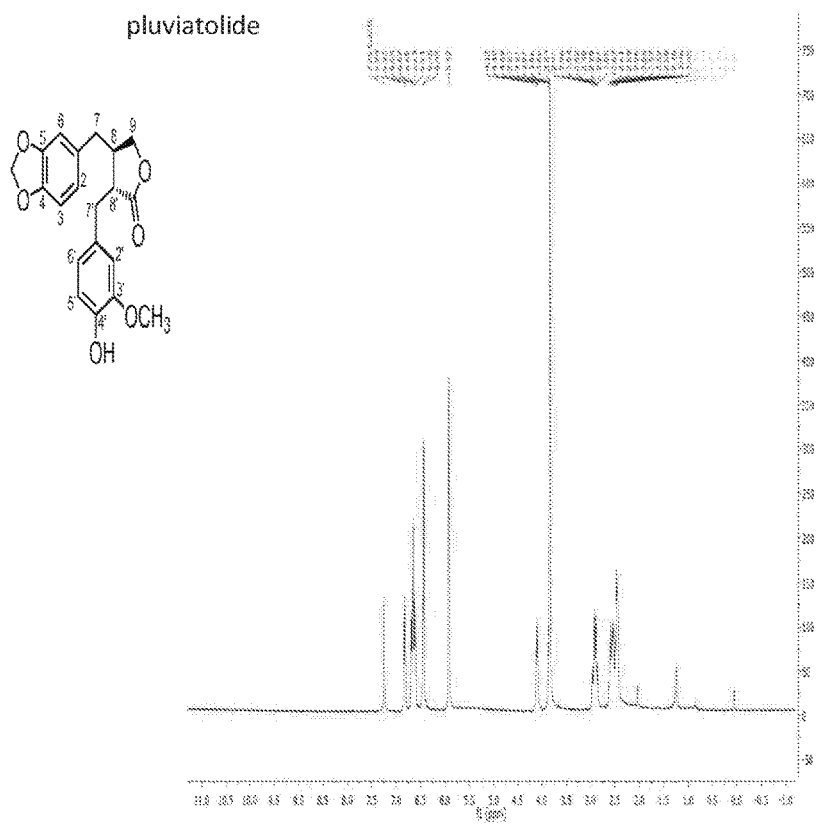
Figure 34F:
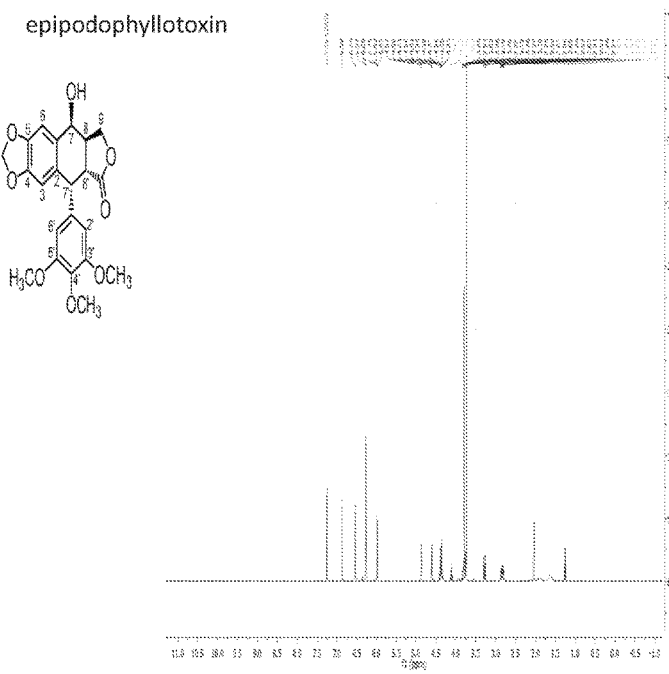
Figure 34G:
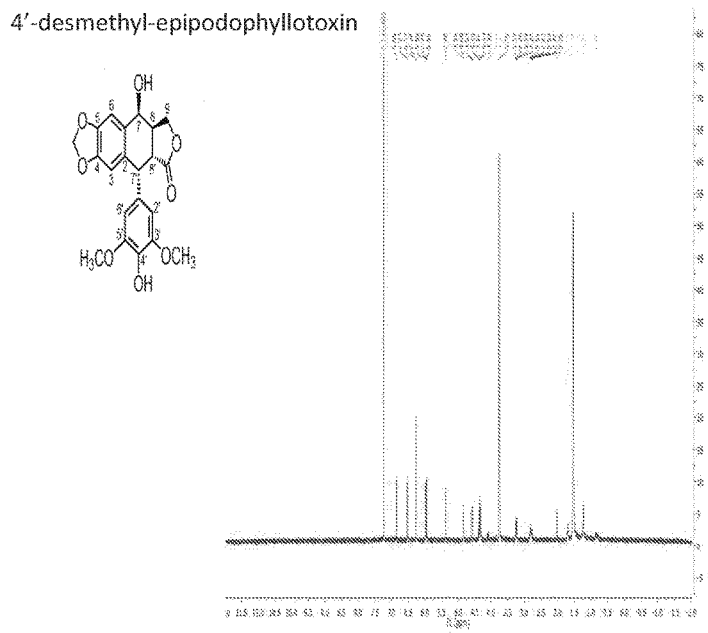

FIG. 32 shows the Golden Gate assembly strategy for multiple-gene constructs for transient expression in *N. benthamiana*.

Figure 33:
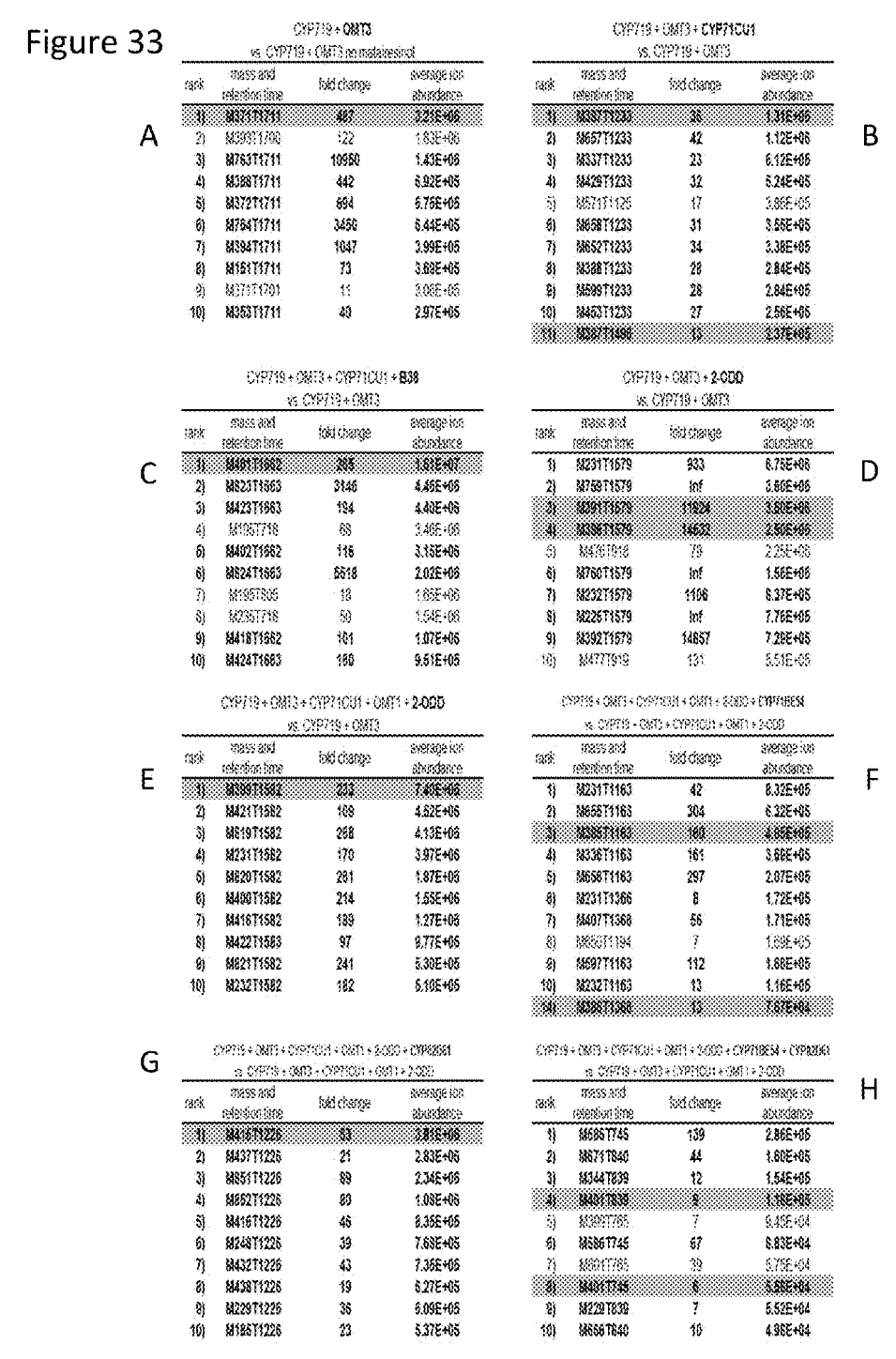

FIG. 33 depicts an XCMS analysis summary of in planta candidate enzyme screening. Results from the computational comparison of the metabolomes generated from the transient expression of different gene combinations in *N. benthamiana* are summarized. The top ten most abundant mass signals that differ for a given co-infiltration relative to a control are reported, along with other mass signals of interest. Results were reproduced at least thrice, each time with three biological replicates for each sample condition. In bold are mass signals derived from identified products in this report (isotope peaks, adducts, in-source fragments, derivatives, etc.). Highlighted in grey are important parent, fragment or adduct ions that have been referred to throughout this report: (A) (−)-5′-desmethoxy-yatein $[M+H]^+$, m/z=371 (B) (−)-5′-desmethyl-yatein $[M+H]^+$, m/z=387 (C) (−)-yatein $[M+H]^+$, m/z=401 (D) (−)-5′-desmethoxy-deoxypodophyllotoxin $[M+NH_4]^+$, m/z=386; $[M+Na]^+$, m/z=391 (E) (−)-deoxypodophyllotoxin $[M+H]^+$, m/z=399 (F) (−)-4′-desmethyl-deoxypodophyllotoxin $[M+H]^+$, m/z=385 (G) (−)-epipodophyllotoxin $[M+H]^+$, m/z=415 (H) (−)-4′-desmethyl-epipodophyllotoxin $[M+H]^+$, m/z=401.

FIG. 34A-G depict $^1$H NMR spectra of various podophyllotoxin intermediates and derivatives and comparison to literature. Minor impurities and residual solvent impurities are marked in grey. $CDCl_3$ solvent peak is marked in red.

FIG. 35 depicts protein sequences for etoposide aglycone enzymes OMT3 (SEQ ID NO: 11), CYP71CU1 (SEQ ID NO: 12), and OMT1 (SEQ ID NO: 13).

FIG. 36 depicts protein sequences for etoposide aglycone enzymes 2-ODD (SEQ ID NO: 14), CYP710E54 (SEQ ID NO: 15), and CYP82D61 (SEQ ID NO: 16).

FIG. 37 depicts the nucleic acid sequence for PLR. SEQ ID NO:1.

FIG. 38 depicts the nucleic acid sequence for SDH. SEQ ID NO:2.

FIG. 39 depicts the nucleic acid sequence for CYP719A23. SEQ ID NO:3.

FIG. 40 depicts the nucleic acid sequence for OMT3. SEQ ID NO:4.

FIG. 41 depicts the nucleic acid sequence for CYP71CU1. SEQ ID NO:5.

FIG. 42 depicts the nucleic acid sequence for OMT1. SEQ ID NO:6.

FIG. 43 depicts the nucleic acid sequence for 2-ODD. SEQ ID NO:7.

FIG. 44 depicts the nucleic acid sequence for CYP71BE54. SEQ ID NO:8.

FIG. 45 depicts the nucleic acid sequence for CYP82D61. SEQ ID NO:9.

FIG. 46 depicts the nucleic acid sequence for DIR. SEQ ID NO:10.

Figure 47:
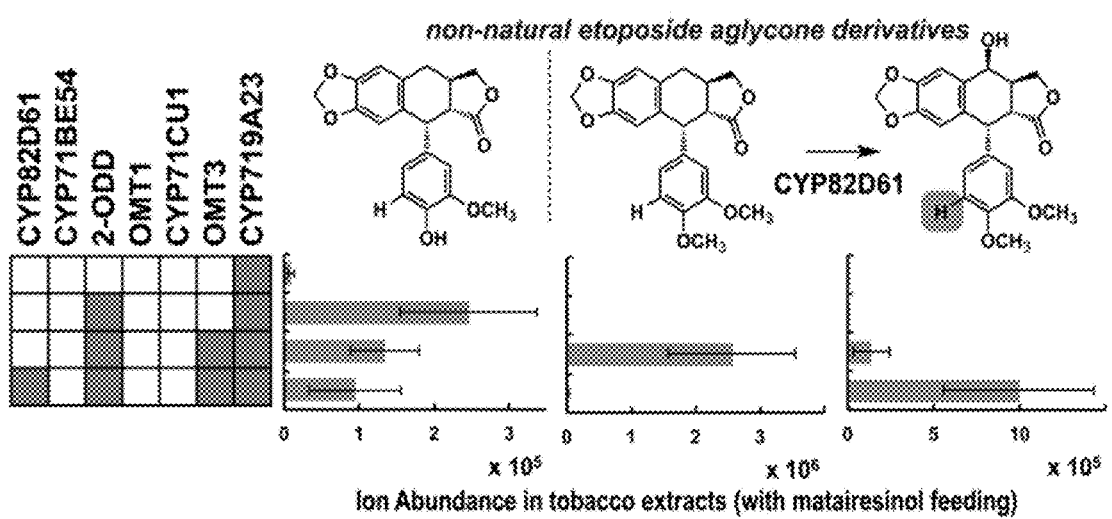

FIG. 47 illustrates the versatility of the various, described enzymes involved in the production of podophyllotoxin intermediates and derivatives. Here, the results are shown when varying enzymes were omitted during the process of producing podophyllotoxin intermediates and derivatives. Far left: a white box indicates that the particular enzyme was omitted, while a grey box indicates that the particular enzyme was utilized. The data demonstrate that 2-ODD and CYP82D61, in particular, tolerate alternative substrates and produce non-natural etoposide aglycone derivatives for which the structures are shown.

DEFINITIONS

The practice of the present invention may employ conventional techniques of chemistry, molecular biology, recombinant DNA, microbiology, cell biology, immunology and biochemistry, which are within the capabilities of a person of ordinary skill in the art. Such techniques are fully explained in the literature. For definitions, terms of art and standard methods known in the art, see, for example, Sambrook and Russell 'Molecular Cloning: A Laboratory Manual', Cold Spring Harbor Laboratory Press (2001); 'Current Protocols in Molecular Biology', John Wiley & Sons (2007); William Paul 'Fundamental Immunology', Lippincott Williams & Wilkins (1999); M. J. Gait 'Oligonucleotide Synthesis: A Practical Approach', Oxford University Press (1984); R. Ian Freshney 'Culture of Animal Cells: A Manual of Basic Technique', Wiley-Liss (2000); 'Current Protocols in Microbiology', John Wiley & Sons (2007); 'Current Protocols in Cell Biology', John Wiley & Sons (2007); Wilson & Walker 'Principles and Techniques of Practical Biochemistry', Cambridge University Press (2000); Roe, Crabtree, & Kahn 'DNA Isolation and Sequencing: Essential Techniques', John Wiley & Sons (1996); D. Lilley & Dahlberg 'Methods of Enzymology: DNA Structure Part A: Synthesis and Physical Analysis of DNA Methods in Enzymology', Academic Press (1992); Harlow & Lane 'Using Antibodies: A Laboratory Manual: Portable Protocol No. I', Cold Spring Harbor Laboratory Press (1999); Harlow & Lane 'Antibodies: A Laboratory Manual', Cold Spring Harbor Laboratory Press (1988); Roskams & Rodgers lab Ref: A Handbook of Recipes, Reagents, and Other Reference Tools for Use at the Bench', Cold Spring Harbor Laboratory Press (2002). Each of these general texts is herein incorporated by reference.

Unless defined otherwise, all technical and scientific terms used herein have the same meaning as commonly understood by a person of ordinary skill in the art to which this invention belongs. The following definitions are intended to also include their various grammatical forms, where applicable. As used herein, the singular forms "a" and "the" include plural referents, unless the context clearly dictates otherwise.

"Polypeptide" or "protein" means at least two covalently attached amino acids including proteins, polypeptides, oligopeptides and peptides. A polypeptide may be made up of naturally occurring amino acids and peptide bonds, synthetic peptidomimetic structures, or a mixture thereof. Thus 'amino acid', or 'peptide residue', as used herein encompasses both naturally occurring and synthetic amino acids. For example, homo-phenylalanine, citrulline and noreleucine are considered amino acids for the purposes of the invention. 'Amino acid' also includes amino acid residues such as proline and hydroxyproline. The side chains may be in either the D- or the L- configuration.

"Isolated" or "purified" generally refers to isolation of a substance (compound, polynucleotide, protein, polypeptide, polypeptide composition) such that the substance comprises a significant percent (e.g., greater than 2%, greater than 5%, greater than 10%, greater than 20%, greater than 50%, or more, usually up to about 90%-100%) of the sample in which it resides. In certain embodiments, a substantially purified or substantially isolated component comprises at least 50%, 80%-85%, or 90-95% of the sample. Techniques for purifying polynucleotides and polypeptides of interest are well-known in the art and include, for example, ion-exchange chromatography, affinity chromatography and sedimentation according to density. Generally, a substance is purified when it exists in a sample in an amount, relative to other components of the sample, that is not found naturally.

The term "sequence identity" refers to the residues in the two sequences, which are the same when aligned for maximum correspondence. Optimal alignment of sequences for comparison can be conducted, e.g., by the local homology algorithm of Smith & Waterman, 1981; by the homology alignment algorithm of Needleman & Wunsch, 1970; by the search for similarity method of Pearson & Lipman, 1988; by computerized implementations of these algorithms (GAP, BESTFIT, FASTA, and TFASTA in the Wisconsin Genetics Software Package, Genetics Computer Group, 575 Science Dr., Madison, Wis.), or by inspection. Sequence identity may be calculated on the basis of residues identical to a reference sequence.

"Conservative variants" are variants that result from substitutions within a family of amino acids that are related in their side chains and so share structurally related residues. Genetically encoded amino acids are generally divided into families: (1) acidic=aspartate, glutamate; (2) basic=lysine, arginine, histidine; (3) non-polar=alanine, valine, leucine, isoleucine, proline, phenylalanine, methionine, tryptophan; and (4) uncharged polar=glycine, asparagine, glutamine, cysteine, serine, threonine, tyrosine. Thus, aspartate and glutamate share structurally related residues; lysine, arginine and histidine share structurally related residues; alanine, valine, leucine, isoleucine, proline, phenylalanine, methionine, and tryptophan share structurally related residues; glycine, asparagine, glutamine, cysteine, serine, threonine and tyrosine share structurally related residues; and so forth. Preferred families: serine and threonine are an aliphatic-hydroxy family; asparagine and glutamine are an amide-containing family; alanine, valine, leucine and isoleucine are an aliphatic family; phenylalanine, tryptophan, and tyrosine are an aromatic family, and cysteine and methionine are a sulfur-containing side chain family. For example, it is reasonable to expect that an isolated replacement of a leucine with an isoleucine or a valine, an aspartate with a glutamate, a threonine with a serine, or a similar replacement of an amino acid with a structurally related amino acid in either the alpha-5, beta-1 and/or gamma-1 chain of a truncated laminin-511 will not have a major effect on the hair-promoting characteristics of the resulting molecule, especially if the replacement does not involve an amino acid within a framework site. Preferred conservative amino acid substitution groups are: valine-leucine-isoleucine, phenylalanine-tyrosine, lysine-arginine, alanine-valine, glutamic acid-aspartic acid, cysteine-methionine, and asparagine-glutamine.

In making such changes, the hydropathic index of amino acids may be considered. The importance of the hydropathic amino acid index in conferring interactive biologic function on a protein is generally understood in the art (Kyte and Doolittle, 1982). It is generally accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. Each amino acid has been assigned a hydropathic index on the basis of its hydrophobicity and charge characteristics (Kyte and Doolittle, 1982), as follows: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

In modifying the presently exemplified sequences (nucleic acid sequences in FIGS. 37-46 and corresponding amino acid sequences for OMT3, CYP71CU1, OMT1, 2-ODD, CYP710E54, CYP82D61 in FIGS. 35 and 36), certain amino acids may be substituted by other amino acids having a similar hydropathic index or score and still result in a protein with similar biological activity, i.e., still obtain a biological functionally equivalent protein. In making such changes, the substitution of amino acids whose hydropathic indices are within ±2 is preferred, those that are within ±1 are particularly preferred, and those within ±0.5 are even more particularly preferred.

Substitution of like amino acids can also be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

Furthermore, amino acid substitutions may also be generally based on the relative similarity of the amino acid side-chain substituents, for example, their hydrophobicity, hydrophilicity, charge, size, and the like but may nevertheless be made to highlight a particular property of the peptide. Exemplary substitutions that take various of the foregoing characteristics into consideration are well known to those of skill in the art and include: arginine and lysine, which, with histidine, are basic at physiological pH; glutamate and aspartate, which are acidic; serine and threonine; glutamine and asparagine; valine, leucine and isoleucine.

A "promoter" is a nucleotide sequence located upstream from a transcriptional initiation site that contains all the regulatory regions required for transcription, including but not limited to constitutive, inducible, developmental, tissue-specific, bacterial, fungal, viral, animal- and plant derived promoters capable of functioning in plant, yeast, bacterial, insect or mammalian cells.

"Operably linked", as used herein, means joined as part of the same nucleic acid molecule, positioned such that transcription is initiated from the promoter.

Vectors useful in the present invention include commercially available expression vectors for use in plant, yeast, bacterial, insect or mammalian cells. Vector DNA can be introduced into prokaryotic or eukaryotic cells via conventional transformation or transfection techniques.

A "heterologous" nucleic acid or coding sequence indicates a nucleic acid that codes for a peptide or protein including an enzyme or equivalent molecule that is normally not present in the host cell and can be expressed in the host cell under suitable conditions.

An "equivalent" or "equivalent molecule" includes modified including truncated sequences that code for a particular enzyme.

DETAILED DESCRIPTION

The present invention relates to compositions and methods for biosynthetically producing podophyllotoxin intermediates and derivatives. In particular, the invention relates to host cells that have been genetically engineered to express recombinant or modified enzymes or their equivalents involved in the production of podophyllotoxin intermediates and derivatives. In one embodiment, the host cells of the present invention are plant cells. In other embodiments, the host cells are yeast, bacterial, insect or mammalian cells, that are commonly known in the art.

All cells are cultured under conditions that are conducive to the expression of functional enzymes that are encoded by heterologous nucleic acids and that are involved in the production of podophyllotoxin intermediates and derivatives, as explained in detail in the experimental section below.

Podophyllotoxin

Podophyllotoxin, a lignan from the endangered medicinal plant Himalayan Mayapple (*Podophyllum hexandrum*), is a known precursor to the antineoplastic compound etoposide (Stahelin et al., 1991; Canel et al., 2000; Gordaliza et al., 2004), that is utilized in a wide variety of malignancies.

Figure 1:
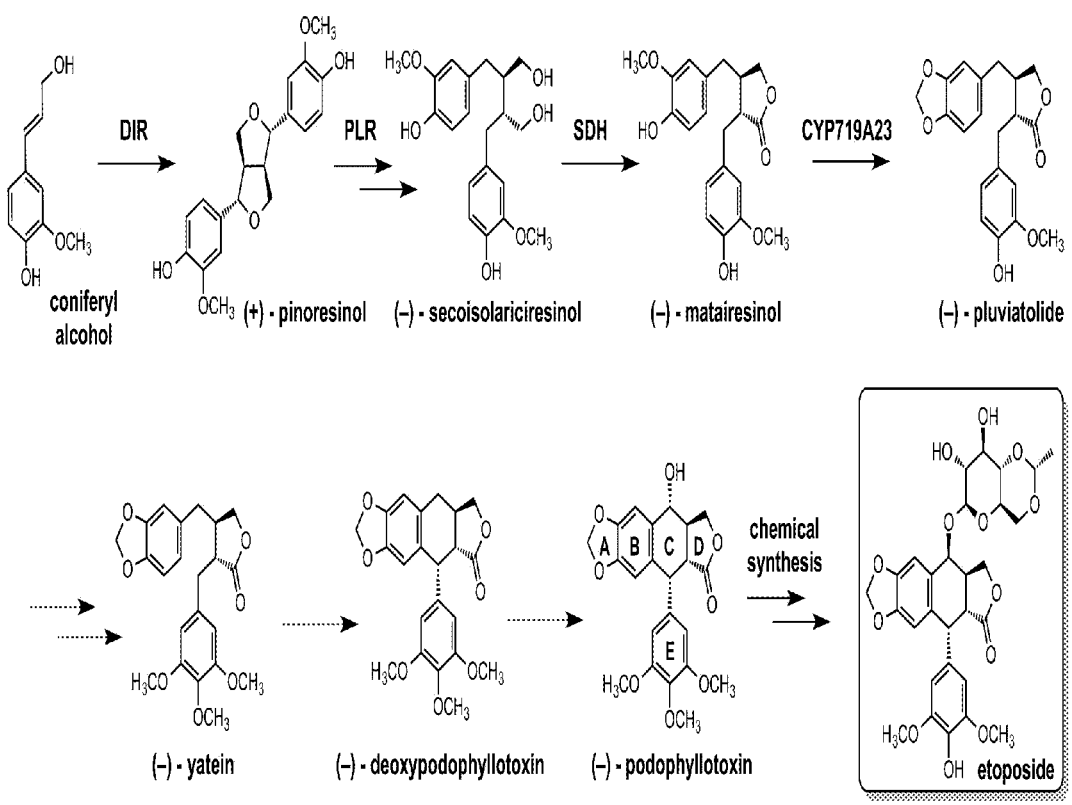
FIG. 1 depicts known components of the biosynthetic pathway of (−)-podophyllotoxin in *P. hexandrum*. Uncharacterized steps are indicated by dashed lines. It is estimated that there are at least five uncharacterized enzymes required in completing the biosynthesis of (−)-podophyllotoxin from (−)-pluviatolide. The anti-cancer agent, etoposide, is semi-synthetically derived from (−)-podophyllotoxin. DIR, dirigent protein; PLR, pinoresinol-lariciresinol reductase; SDH, secoisolariciresinol dehydrogenase.

The currently used route for the production of etoposide involves the isolation of (−)-podophyllotoxin from the Mayapple plant (Lata et al., 2009) and its subsequent multistep, semisynthetic conversion to etoposide. The fact that *Podophyllum hexandrum* is an endangered plant species has long motivated the search for alternative routes to (−)-podophyllotoxin, such as plant cell culture (Malik et al., 2014), but the implementation of biosynthetic production has proven difficult. Previous efforts have uncovered the early steps of podophyllotoxin biosynthesis (Dinkova-Kostova et al., 1996; Davin et al., 1997; Xia et al., 2001; Marques et al., 2013), revealing that the podophyllotoxin core derives from an unusual enantio- and site-selective dimerization of coniferyl alcohol to pinoresinol, and providing a starting point for identifying additional biosynthetic genes (FIG. 1).

Biosynthetic gene discovery in *Podophyllum* presents two key challenges. The genome of *Podophyllum* has not been sequenced, and at an estimated 16 Gb (Subramani et al., 2011), it is 200× the size of the *Arabidopsis* genome. Moreover, genetic tools for constructing Podophyllum mutants are laborious (Rajesh et al., 2013) and the plant grows slowly, making it difficult to study in the laboratory.

Podophyllotoxin Derivatives

Podophyllotoxin and podophyllotoxin derivatives such as (−)-4'-desmethyl-epipodophyllotoxin provide the basis for semisynthetic compounds such as etoposide and teniposide which have gained great importance as antineoplastic agents due to their ability to inhibit topoisomerase II in various malignancies such as small-cell lung, bladder, prostate, lung, stomach, and uterine cancers, testicular carcinoma, lymphoma, Kaposi's sarcoma, Hodgkin's and non-Hodgkin's lymphoma, and mycosis fungoides.

Biosynthetic Production of Etoposide

For commercial production, podophyllotoxin is isolated from the roots and rhizomes of a *Podophyllum* species such as *P. hexandrum* (Kumar et al., 2015) or *P. peltatum*. Podophyllotoxin is then chemically converted into etoposide and similar compounds such as teniposide. Since this kind of commercial production of etoposide relies on the availability of slow growing and/or critically endangered (*P. hexandrum*) plant species, biosynthetic production of etoposide is highly desirable.

Known components. Starting with coniferyl alcohol, the known components of the biosynthetic pathway to arrive from coniferyl alcohol to podophyllotoxin comprise (+)-pinoresinol, (−)-secoisolariciresinol, (−)-matairesinol, (−)-pluviatolide, (−)- yatein, (−)-deoxypodophyllotoxin, and (−)-podophyllotoxin. (−)-Podophyllotoxin is then chemically transformed into etoposide.

Newly elucidated biosynthetic genes OMT3, CYP71CU1, OMT1, 2-ODD, CYP71BE54 and CYP82D61. Six biosynthetic genes and their encoded enzymes for the production of (−)-4'-desmethyl-epipodophyllotoxin, the aglycone etoposide, and other intermediates were identified. They are displayed in FIG. 31.

A biosynthetic route facilitates an easier and more economical access to etoposide as well as natural and unnatural derivatives that are difficult to produce synthetically.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible. In the following, experimental procedures and examples will be described to illustrate parts of the invention.

Experimental Procedures

The following methods and materials were used in the examples that are described further below.

Transcriptomics Data Mining And Analysis Of The Medicinal Plants Consortium Data Sets RNA-Sequencing data from *P. hexandrum* was downloaded from the Medicinal Plants Consortium database (Marques et al., 2013). The number of fragments per kilobase of contig per million mapped reads (FPKM) for each contig and condition (leaf-1, leaf-2, rhizome-1, rhizome-2, stem-1, stem-2, stem-3) was determined using the number of paired aligned reads provided in the counts files. Contigs representing known (−)-podophyllotoxin biosynthetic genes were determined and annotated by tblastn with query sequences obtained from the NCBI database: (DIR, AIA24413.1; PLR, ABY75535.2; SDH, ABN14311.1; CYP719A23, AGC29953.1). Contigs were also annotated by blastx using an Arabidopsis proteome (The Arabidopsis Information Resource) database. Approximately 100 O-methyltransferase (OMT) and 300 cytochrome P450 (CYP) contigs were identified.

Multiple contigs were found to represent the same gene. OMT gene candidates from this data set were chosen based on the availability of full coding sequence, similar expression profiles to known biosynthetic genes, and similarity (best blastx hit and % identity) to known plant genes involved in secondary metabolism (OMT1, Ph13451 [Contig number, Ph refers to contigs from the Medicinal Plants Consortium dataset]; OMT2, Ph14232; OMT3, Ph18546; OMT4, Ph6083). CYP gene candidates (see Table 2 for primers) were chosen similarly. For biosynthetic steps that occur downstream of (−)-deoxypodophyllotoxin formation, CYP contigs with rhizome-specific expression were considered.

TABLE 2

Gene candidates for *N. benthamiana* screening
(Ph = Medicinal Plants Consortium transcriptome, Phex = leaf transcriptome
assembled in this report; Gibson overlap regions are displayed in bold)

| Primer Name | Primer Sequence 5'-3' |
|---|---|
| PhDIR_pEAQ_F | ATT CTG CCC AAA TTC GCG ACC GGT ATG GGA GGA GAA AAA GCT TTC AG |
| PhDIR_pEAQ_R | GAA ACC AGA GTT AAA GGC CTC GAG TTA CCA ACA CTC ATA CAA CTT TAT ATC AAC |
| PhPLR_pEAQ_F | TAT TCT GCC CAA ATT CGC GAC CGG TAT GGC TAA GAG CAG AGT TCT C |
| PhPLR_pEAQ_R | TGA AAC CAG AGT TAA AGG CCT CGA GCT ACA AAT ATC GTT GAT ATT CGG |
| PhSDH_pEAQ_F | TAT TCT GCC CAA ATT CGC GAC CGG TAT GGG ATC CAC TTC TAC ACC |
| PhSDH_pEAQ_R | TGA AAC CAG AGT TAA AGG CCT CGA GTC AAG CCA ATC CAT GTT TCA ATG |
| CYP719A23_pEAQ_F | TAT TCT GCC CAA ATT CGC GAC CGG T ATG GAG ATG GAG ATG AGT GTC |
| CYP719A23_pEAQ_R | TGA AAC CAG AGT TAA AGG CCT CGA GTC AAG GAT TGC GAG GAA TG |
| Ph13451 (OMT1) pEAQ_F | TAT TCT GCC CAA ATT CGC GAC CGG TAT GGA TAC TAG GGC TGA TGC |
| Ph13451 (OMT1) pEAQ_R | TGA AAC CAG AGT TAA AGG CCT CGA GTT AGG GAA ACA CTT CAA TGA TAG ACT TG |
| Ph14232 (OMT2) pEAQ_F | TAT TCT GCC CAA ATT CGC GAC CGG TAT GGC TCC ACA AAG AGA TGC |
| Ph14232 (OMT2) pEAQ_R | TGA AAC CAG AGT TAA AGG CCT CGA GTT AAG GAA ATA CTT GAA TGA AAG ACC TTA G |
| Ph18546 (OMT3) pEAQ_F | TAT TCT GCC CAA ATT CGC GAC CGG TAT GGA AAT GGC TCC AAC AAT G |
| Ph18546 (OMT3) pEAQ_R | TGA AAC CAG AGT TAA AGG CCT CGA GTT AGG GAA ACA CTT CAA TGA TAG ACT TG |
| Ph6083 (OMT4) pEAQ_F | TAT TCT GCC CAA ATT CGC GAC CGG TAT GGC AGA CGA AAC ATC AGA AAC C |
| Ph6083 (OMT4) pEAQ_R | TGA AAC CAG AGT TAA AGG CCT CGA GTC ACT TGG TAA ACT CTA TGA CGG TG |
| Ph2456_pEAQ_F | TAT TCT GCC CAA ATT CGC GAC CGG TAT GAT ATC TAC AGC CTG GTT ATG G |
| Ph2456_pEAQ_R | TGA AAC CAG AGT TAA AGG CCT CGA GTC AAG TGT ACA ACC TGG GTT C |
| Ph3787_pEAQ_F | TAT TCT GCC CAA ATT CGC GAC CGG TATG GAT CAC CTC TCC ACC |
| Ph3787_pEAQ_R | TGA AAC CAG AGT TAA AGG CCT CGA GCT ACT GAT AAA CAA AAT CAG GTA GGC |
| Ph8214_pEAQ_F | TAT TCT GCC CAA ATT CGC GAC CGG TATG GAA ATG TTT CAT CCA TTT ATA TTG C |
| Ph8214_pEAQ_R | TGA AAC CAG AGT TAA AGG CCT CGA GTC ATA GCT GCC TAG GAA GTT TC |
| Ph4178_pEAQ_F | ATT CTG CCC AAA TTC GCG ACC GGT ATG GAG TTG TGG TTC ATC TTC TTA TTA TTC |
| Ph4178_pEAQ_R | GAA ACC AGA GTT AAA GGC CTC GAG TTA TTT TAC TCT TGG AGT GAT ACA AGC C |
| Ph172938_pEAQ_F | ATT CTG CCC AAA TTC GCG ACC GGT ATG GAG TTG ATT TTA TTG GTA TTA TTC ACT ATC |
| Ph172938_pEAQ_R | GAA ACC AGA GTT AAA GGC CTC GAG TCA AGC TTG GTA CGG GTT G |
| Ph5690_pEAQ_F | ATT CTG CCC AAA TTC GCG ACC GGT ATG ACA TCA GTA ACA ACC AGC AG |
| Ph5690_pEAQ_R | GAA ACC AGA GTT AAA GGC CTC GAG TCA TAC TTT AAA GTG GTC TAT CAA GTT CC |
| Ph2327_pEAQ_F | ATT CTG CCC AAA TTC GCG ACC GGT ATG GAA CCA ATA TTA GTA TAC TTC CTT CTT TTC |
| Ph2327_pEAQ_R | GAA ACC AGA GTT AAA GGC CTC GAG CTA CAC CTG AGA AAG GAA ATT CAA CAT G |
| Ph3089_pEAQ_F | ATT CTG CCC AAA TTC GCG ACC GGT ATG GCG GAA ACC ACA GG |
| Ph3089_pEAQ_R | GAA ACC AGA GTT AAA GGC CTC GAG CTA AGC ATA GAG GGC TGG GTC |
| Ph4466_pEAQ_F | ATT CTG CCC AAA TTC GCG ACC GGT ATG GGA GAT ATT ATG GTT GTT GTG C |

TABLE 2-continued

Gene candidates for *N. benthamiana* screening
(Ph = Medicinal Plants Consortium transcriptome, Phex = leaf transcriptome
assembled in this report; Gibson overlap regions are displayed in bold)

| | |
|---|---|
| Ph4466_pEAQ_R | GAA ACC AGA GTT AAA GGC CTC GAG TTA GAT TTT ACA TAG GAC CAG TGG AGC |
| Ph11943_pEAQ_F | ATT CTG CCC AAA TTC GCG ACC GGT ATG TAC TCT TGG GCT ACA ATG TTC |
| Ph11943_pEAQ_R | GAA ACC AGA GTT AAA GGC CTC GAG TCA TAA TTT GTC AAT GTG AGG GCG |
| Ph5422_pEAQ_F | ATT CTG CCC AAA TTC GCG ACC GGT ATG GAG AAT TTG ACC ACT GTG TC |
| Ph5422_pEAQ_R | GAA ACC AGA GTT AAA GGC CTC GAG CTA ATC CTG AAA CCC ATA TTC CTT GTT G |
| Ph2443_pEAQ_F | ATT CTG CCC AAA TTC GCG ACC GGT ATG GAA ACA ATA CTC TCC ATG TTG C |
| Ph2443_pEAQ_R | GAA ACC AGA GTT AAA GGC CTC GAG CTA CTC TAA TTG GGA AAT AAG GTT TGC C |
| Ph2002_pEAQ_F | ATT CTG CCC AAA TTC GCG ACC GGT ATG AAT GGG ACT ATT GTA ATA GAA CAA AAT TTC |
| Ph2002_pEAQ_R | GAA ACC AGA GTT AAA GGC CTC GAG TCA TTG TTT CAC TCT AGG GAT GAG AAC |
| Phex524 (CYP71CU1)_pEAQ_F | TAT TCT GCC CAA ATT CGC GAC CGG TAT GGA AAC ATT TCA GTG CCT C |
| Phex524 (CYP71CU1)_pEAQ_R | TGA AAC CAG AGT TAA AGG CCT CGA GTC AAG AGG ATC GAG AAA TAG G |
| Phex1550 (2-ODD)_pEAQ_F | ATT CTG CCC AAA TTC GCG ACC GGT ATG GGT TCT ACA GCA CCC |
| Phex1550 (2-ODD)_pEAQ_R | GAA ACC AGA GTT AAA GGC CTC GAG TCA TGC ACC TGT GTA CGC |
| Phex32688_pEAQ_F | ATT CTG CCC AAA TTC GCG ACC GGT ATG GAA TTG TCA CAA ATT CTA GTT TAC TCG |
| Phex32688_pEAQ_R | GAA ACC AGA GTT AAA GGC CTC GAG CTA GCC GAT CTT CTC ACT TGT C |
| Phex15199_pEAQ_F | ATT CTG CCC AAA TTC GCG ACC GGT ATG GAA GAG ATT CGA ATC AGC C |
| Phex15199_pEAQ_R | GAA ACC AGA GTT AAA GGC CTC GAG TCA AAG TTT GTG TAG AAT AAG CTG AAC AC |
| Phex359_pEAQ_F | ATT CTG CCC AAA TTC GCG ACC GGT ATG TAT GAG GAC ATC TCT GAT CTC TC |
| Phex359_pEAQ_R | GAA ACC AGA GTT AAA GGC CTC GAG CTA AAC AAA CTC AAT ACT AAC CCC ACC |
| Phex34339_pEAQ_F | ATT CTG CCC AAA TTC GCG ACC GGT ATG TCG CTC TCC CTC TTG G |
| Phex34339_pEAQ_R | GAA ACC AGA GTT AAA GGC CTC GAG CTA GTC ATC ATC TTC AAC TC GAA C |
| Ph57270_pEAQ_F | ATT CTG CCC AAA TTC GCG ACC GGT ATG GAT CTT GCT TCC ATT CTC TC |
| Ph57270_pEAQ_R | GAA ACC AGA GTT AAA GGC CTC GAG CTA ACA AGG ACC AGT AGC TGA CTT ATA AG |
| Ph29054_pEAQ_F | ATT CTG CCC AAA TTC GCG ACC GGT ATG GAT AGT ATC CTC CAC CTA CTC |
| Ph29054_pEAQ_R | GAA ACC AGA GTT AAA GGC CTC GAG TTA TAC ATA TGC TCC AGG CGA AAG |
| Ph14372 (CYP71BE54)_pEAQ_F | ATT CTG CCC AAA TTC GCG ACC GGT ATG GAG TTC CTT TCA TTT CCC TTA TC |
| Ph14372 (CYP71BE54)_pEAQ_R | GAA ACC AGA GTT AAA GGC CTC GAG CTA TTC TTT TGT AGT CGA TCT TTC CAG C |
| Ph5041_pEAQ_F | ATT CTG CCC AAA TTC GCG ACC GGT ATG GGA TAT TTG ATT GCA GTA TGT GTA C |
| Ph5041_pEAQ_R | GAA ACC AGA GTT AAA GGC CTC GAG TTA TGG TTT GTC GAT GTT TAG GCG |
| Ph4618_pEAQ_F1 | ATT GCC CTC GGT GTA ATC |
| Ph4618_pEAQ_F2 | ATT CTG CCC AAA TTC GCG ACC GGT ATG GGC TAT TTG ATA GCA ATT GCC CTC GGT GTA ATC |
| Ph4618_pEAQ_R | GAA ACC AGA GTT AAA GGC CTC GAG TCA GAA TTT GCT TAG ACT ATT GCT GC |
| Ph35407(CYP82D61)_pEAQ_F | ATT CTG CCC AAA TTC GCG ACC GGT ATG GAT TCC CTG CAC TGC |
| Ph35407(CYP82D61)_pEAQ_R | GAA ACC AGA GTT AAA GGC CTC GAG CTA GAC AAA ACA TTT TGG AGA GAT GCG |
| Ph18808_pEAQ_F | ATT CTG CCC AAA TTC GCG ACC GGT ATG GGT AGT GTT CCT GTG C |

TABLE 2-continued

Gene candidates for *N. benthamiana* screening
(Ph = Medicinal Plants Consortium transcriptome, Phex = leaf transcriptome
assembled in this report; Gibson overlap regions are displayed in bold)

| | |
|---|---|
| Ph18808_pEAQ_R | GAA ACC AGA GTT AAA GGC CTC GAG TCA AAT TTC ACC ATC CCA AAG TTC |
| Ph55921_pEAQ_F | ATT CTG CCC AAA TTC GCG ACC GGT ATG GGA ATT CCA CGG ACG |
| Ph55921_pEAQ_R | GAA ACC AGA GTT AAA GGC CTC GAG CTA ATA ACA TCT TGA CTG TTT CAA CAT TAA TCT AG |

Heterologous expression in alternative expression hosts for
in vitro characterization (in bold are Gibson overlap regions)

| Primer Name | Primer Sequence 5'-3' |
|---|---|
| CYP719A23_pYeDP60_F | TAC ACA CAC TAA ATT ACC GGA TCC ATG GAG ATG GAG ATG AGT GTC |
| CYP719A23_pYeDP60_R | ACA TGG GAG ATC CCC CGC GAA TTC TCA GGA ATT GCG AGG AAT G |
| Ph18456 (OMT1) pET28a_F | CTG GTG CCG CGC GGC AGC CAT ATG GAA ATG GCT CCA ACA ATG |
| Ph18456 (OMT1) pET28a_R | GTG GTG GTG GTG GTG GTG CTC GAG TTA GGG AAA CAC TTC AAT GAT AGA CTT G |
| pET24b_C-His_OMT1_F | TAA CTT TAA GAA GGA GAT ATA CAT ATG GAT ACT AGG GCT GAT GC |
| pET24b_C-His_OMT1_R | GTG GTG GTG GTG GTG GTG CTC GAG CTT CTT ATG AAT TCA ATG ACT GAA ATG C |
| pET24b_C-His_2-ODD_F | TAA CTT TAA GAA GGA GAT ATA CAT ATG GGT TCT ACA GCA CCC |
| pET24b_C-His_2-ODD_R | GTG GTG GTG GTG GTG GTG CTC GAG TGC ACC TGT GTA CGC C |
| pYeDP60_Phex524 (CYP71CU1)_F | TAC ACA CAC TAA ATT ACC GGA TCC ATG GAA ACA TTT CAG TGC CTC |
| pYeDP60_Phex524 (CYP71CU1)_F | ACA TGG GAG ATC CCC CGC GAA TTC TC AAG AGG ATC GAG AAA TAG G |
| pYeDP60_Ph14372 (CYP71BE54)_F | TAC ACA CAC TAA ATT ACC GGA TCC ATG GAG TTC TTC TCA TTT CCC TTA TC |
| pYeDP60_Ph14372 (CYP71BE54)_R | ACA TGG GAG ATC CCC CGC GAA TTC CTA TTC TTT TGT AGT CGA TCT TTC CAG C |
| pYeDP60_Ph35407 (CYP82D61)_F | TAC ACA CAC TAA ATT ACC GGA TCC ATG GAT TCC CTG CAC TGC |
| pYeDP60_Ph35407 (CYP82D61)_R | ACA TGG GAG ATC CCC CGC GAA TTC CTA GAC AAA ACA TTT TGG AGA GAT GCG |

Multi-gene constructs for in planta expression (in bold are BsaI sites)

| Gene Name | Primer Sequence 5'-3' |
|---|---|
| pEAQ-GG_1F | CCG ATG AAA CGT TTA AGC AGGTC TCC TAT ACG TAA TCA TGG TCA TAG CTG TTG C |
| pEAQ-GG_1R | CAC AGA TGA TGT GGA CAA GCC TG |
| pEAQ-GG_2F | CAG GCT TGT CCA CAT CAT CTG TG |
| pEAQ-GG_2R | TGC TTA AAC GTT CCA TCG GGGTC TCT CTT AAT TAA CAA TTC ACT GGC CGT CG |
| pEAQ-GG-3Gene-AF | GGT CTC GTA AGA ATT CGA GCT CCA CCG C |
| pEAQ-GG-3Gene-BR | GGT CTC CTC GTG CGC GCC AAG CTT GAG |
| pEAQ-GG-3Gene-BF | GGT CTC GAC GAA ATT CGA GCT CCA CCG C |
| pEAQ-GG-3Gene-CR | GGT CTC CTC CAG CGC GCC AAG CTT GAG |
| pEAQ-GG-3Gene-CF | GGT CTC GTG GAA ATT CGA GCT CCA CCG C |
| pEAQ-GG-3Gene-ZR | GGT CTC CTA TAG CGC GCC AAG CTT GAG |

TABLE 2-continued

Gene candidates for *N. benthamiana* screening
(Ph = Medicinal Plants Consortium transcriptome, Phex = leaf transcriptome
assembled in this report; Gibson overlap regions are displayed in bold)

qRT-PCR primers

| Primer Name | Primer Sequence 5'-3' |
| --- | --- |
| qRT-PCR_PhDIR_F | ATG CAA CAG CAT CCA TCG |
| qRT-PCR_PhDIR_R | GAT CGT CGA ACA CAA CCA C |
| qRT-PCR_PhPLR_F | GCC ATC GGA GTT TGG TAT G |
| qRT-PCR_PhPLR_R | TCG ATC GCC TTT CTC ACC |
| qRT-PCR_PhSDH_F | GGA TAC CAC CAT AGC CAA GC |
| qRT-PCR_PhSDH_R | ATG CTG TAA GGA GTG GTG CTC |
| qRT-PCR_PhCYP719_F | TTA CGC ATG GTC CTT TAG GG |
| qRT-PCR_PhCYP719_R | GCA TCT TGT TGC ATC TCT CG |
| qRT-PCR_PhOMT3_F | AAG GTT GGC GAT GAG TGT G |
| qRT-PCR_PhOMT3_R | ACC CAC GTT TCC TGT ACC AC |
| qRT-PCR_PhActin_F | ACC CTC CAA TCC AGA CAC TG |
| qRT-PCR_PhActin_R | GGA TGA GCA AGG AGA TCA CTG | mRNA Extraction and cDNA Template Preparation

RNA was extracted from *P. hexandrum* var. chinense ex MD97150 (Far Reaches Farm, Port Townsend, WA) and *P. hexandrum* (Dancing Oaks Nursery, Monmouth, Oreg.) leaf and rhizome tissues using the Spectrum Plant Total RNA Kit (Sigma-Aldrich) according to the manufacturer's instructions. cDNA was prepared from extracted mRNA using the SuperScript III First-Strand Synthesis System (Invitrogen).

qRT-PCR Analysis of OMT3 and Known podophyllotoxin Biosynthetic Genes after *P. hexandrum* Leaf Wounding A *P. hexandrum* (Dancing Oaks Nursery, Monmouth, Oreg.) leaf was removed from the stem with scissors and 0h time point (control) tissue samples were collected (one from each leaflet, three total from a single leaf), flash frozen with liquid nitrogen and stored at −80° C. for later manipulation. The leaf was then immediately wounded by piercing the leaf approximately a hundred times with fine tweezers throughout the entire surface of the leaf. The wounded leaf was placed in a petri dish with distilled water and moved to a growth chamber under a 16 h light cycle (photon flux of 100 µmol m$^{-2}$ s$^{-1}$, 22° C., 50% relative humidity) approximately an hour after the start of the light cycle. Three tissue samples, one from each leaflet, were removed from the leaf 3, 6, 9, 12 and 24 h after wounding, flash frozen by liquid nitrogen and stored at −80° C. for later use in metabolomics analysis, gene profiling and RNA-Sequencing.

cDNA templates were prepared from the isolated tissues as described above. Quantitative RT-PCR was performed using cDNA templates and gene-specific primers for DIR, PLR, SDH, CYP719A23, OMT3 and ACTIN (see Table 2) (Bhattacharyya et al., 2013). Each cDNA was amplified by real-time PCR using SensiMix SYBR Hi-ROX Kit (Bioline) and the ABI StepOnePlus (Applied Biosystems). ACTIN expression was used to normalize the expression values in each sample, and relative expression values were determined against the 0h time point (before wounding) using the comparative $C_t$ method ($2^{-\Delta\Delta Ct}$) (Schmittgen et al., 2008). Analysis was repeated once with another biological sample; similar results were obtained.

RNA-Seq Library Preparation, Next-generation Sequencing and Co-expression Analysis A multiplexed RNA-Seq cDNA library was prepared from RNA isolated from the *P. hexandrum* wounding experiment (three biological replicates of 0, 3, 9 and 12 h after wounding, 12 samples total) using the NEBNext Ultra Directional RNA Library Prep Kit for Illumina (New England Biolabs) according to the manufacturer's instructions. The quality and average length (insert size was approximately 200 bp) of cDNAs in the library were determined using a High Sensitivity DNA chip on a 2100 Bioanalyzer (Agilent Technologies). Libraries were sequenced (paired-end, 100 bp) on a single lane of HiSeq2000 (Illumina) at the Sequencing Service Center by the Stanford Center for Genomics and Personalized Medicine. The FASTX-toolkit (Hannonlab Fastx-toolkit, 2010) was used for quality assessment and cleaning of reads. Reads were trimmed at the 5'-end by 13 by to remove biases associated with random priming. Reads with Phred quality scores of less than 20 were trimmed from the 3'-end; reads were discarded if resulting length was less than 50 bp. Low complexity sequences were removed. A transcriptome was assembled de novo using Velvet and Oases (Schulz et al., 2012) with a k-mer of 71. The clustering tool CD-HIT-EST (Li & Godzik, 2006) was used to identify sequences with greater than 99% identity from the assembly; only the longest representative transcript was kept. The set of transcripts was further assembled with CAP3 (Huang et al., 1999) to combine contigs with significant overlaps (minimum 95% identity over at least 100 bp). Assembled transcripts were annotated by blastx using the Arabidopsis proteome (The Arabidopsis Information Resource) as a database and the NCBI non-redundant database, if necessary. eXpress (Roberts et al., 2013) was used to quantify gene expression levels under each experimental condition by mapping paired reads to assembled transcripts. Effective counts were TMM (Trimmed Mean of M-values) normalized by edgeR (Robinson et al., 2010). Contigs assembled using this data are annotated Phex followed by the contig number.

RNA-Seq Co-expression Analysis and Candidate Selection

On the basis of the predicted enzyme activities required for the missing pathway steps, the transcriptome data was mined for gene sequences annotated O-methyltransferases (OMT), cytochromes P450 (CYP), 2-oxoglutarate/Fe(II)-dependent dioxygenases (2-ODD), and polyphenol oxidases (PPO). Co-expression analysis was then performed based on Pearson's correlation using DIR as a bait gene (FIG. 12). OMT3 (rank 2 and 3) and SDH (rank 28) were among the genes whose expression profiles most closely matched that of DIR. Known pathway genes were highly expressed compared to other genes (1-2 orders of magnitude difference in number of normalized read counts; median TMM normalized effective counts were greater than 500). An expression level cutoff was used (contigs with median TMM normalized effective counts <500 were removed) on the top twenty genes most closely co-expressed with DIR. Four potential gene candidates were identified: Phex30848 (2-ODD), Phex32688 (CYP), Phex13114 (OMT1, previously tested), and Phex359 (PPO). The qRT-PCR gene profiling after leaf wounding from above revealed two similar but distinct expression patterns (DIR, SDH and OMT3 vs. PLR and CYP719A23), suggesting separate transcriptional regulons. Therefore, coexpression analysis was also performed using CYP719A23 as a bait gene (FIG. 13). By applying the same expression level cutoff on the twenty genes whose expression profiles most closely matched that of CYP719A23, two additional candidates were identified: Phex34339 (PPO) and Phex524 (CYP71CU1). Phex15199 (CYP) was also chosen because it showed an interesting elicitation pattern distinct from that observed from known pathway genes.

To further validate candidate selection, average linkage, hierarchical clustering analysis was performed with CLUSTER (version 3.0) using expression data (TMM normalized, log 2-scaled, and median-centered effective counts) from transcript sequences annotated as cytochromes P450 (CYP), O-methyltransferases (OMT), Fe(II) and 2-oxoglutarate dependent dioxygenases (2-ODD), polyphenol oxidases (PPO) and known (−)-podophyllotoxin biosynthetic genes (DIR, PLR, SDH, CYP719A23 and OMT3) (FIG. 9B and FIG. 16). Contigs with median TMM normalized effective read counts less than 500 were removed. Six of our seven candidates, three of four known pathway genes and OMT3 were contained in a single clade of 22 genes. As before, multiple transcripts were found to represent the same gene. The heat map was visualized by Treeview. When computationally taxing, bioinformatics work was performed on a computational cluster operated by the Stanford Genetics Bioinformatics Service Center.

Cloning of podophyllotoxin Biosynthetic Genes and Candidate Genes

Phusion High-Fidelity DNA Polymerase (Thermo Scientific) was used for all PCR amplification steps according to the manufacturer's instructions. All other enzymes used for cloning were purchased from New England Biolabs. Oligonucleotide primers were purchased from Integrated DNA Technologies. DNA excised from agarose gels was purified using the Zymoclean Gel DNA Recovery Kit (Zymo Research). E. coli TOP 10 cells (Invitrogen) were used for plasmid isolation prior to transformation into other heterologous hosts. Plasmid DNA was isolated from E. coli cultures using the QIAprep Spin Miniprep Kit (Qiagen). For a list of primers used for cloning, see Table 2.

For N. benthamiana transient expression, all gene sequences were amplified from P. hexandrum cDNA template. Purified amplicons were inserted into pEAQ-HT (Sainsbury et al., 2009) ($Kan^R$) plasmid digested with AgeI and XhoI in an isothermal DNA assembly reaction, as described (Gibson et al., 2009).

For N. benthamiana transient expression of multiple genes from the same Agrobacterium strain, a multi-gene construct was created using Golden Gate assembly. A Golden Gate dedicated pEAQ-HT plasmid (pEAQ-HT-GG) was constructed by PCR amplification and Gibson assembly to remove the region containing promoter, 5'-UTR, multi-cloning site, 3'-UTR and terminator sequences, and to insert two XbaI restriction sites linked to two distinct recognition sites separated by a linker sequence. Gene sequences were amplified from pEAQ-HT vectors carrying the gene of interest starting from promoter and ending with terminator and flanked with XbaI restriction sites linked with distinct recognition sites. Purified amplicons were inserted into pEAQ-HT-GG by Golden Gate assembly as described (Engler et al., 2008) to construct pEAQ-HTGG: DIR-PLR-SDH and pEAQ-HT-GG:CYP719A23-OMT3 (FIG. 32).

For the expression of CYPs in S. cerevisiae, the sequences were amplified from cloned pEAQ-HT vectors carrying the CYP sequence of interest and the purified amplicons were individually inserted into pYeDP60 ($Amp^R$) plasmid digested with BamHI and XhoI in a Gibson assembly reaction.

For the expression of OMT3 in E. coli, the sequence was amplified from pEAQ-HT:OMT3. The purified amplicon was inserted into pET28a ($Kan^R$) plasmid digested with NdeI and XhoI by Gibson assembly. The final construct was designed to express OMT3 with an N-terminal 6xHis tag.

For the expression of OMT1 and 2-ODD in E. coli, the sequences were amplified from their respective pEAQ-HT vectors. The purified amplicons were individually inserted into pET24b ($Kan^R$) plasmid digested with NdeI and XhoI by Gibson assembly. The final constructs were designed to express the enzymes with a C-terminal 6xHis tag.

The assembly reaction mixtures were used directly to transform E. coli TOP10 cells and the isolated plasmids harboring the desired insert were confirmed by Sanger DNA sequencing performed by Elim Biopharm.

Transient Expression and Candidate Gene Screening in N. benthamiana pEAQ-HT constructs were transformed into Agrobacterium tumafaciens (GV3101) using the freeze-thaw method. Transformants were grown on LB plates containing 50 μg/mL kanamycin and 30 μg/mL gentamicin at 30° C. Cells were removed with a 1 mL pipette tip and resuspended in 1 mL of LB medium, centrifuged at 5000 g for 5 min and supernatant removed. Pellet was resuspended in 10 mM MES buffer, pH=5.6, 10 mM MgC12, 150 μM acetosyringone and incubated at room temperature for 1 h. Agrobacterium suspensions ($OD_{600}$=0.3 for each strain) were infiltrated into the underside of N. benthamiana leaves with a needleless 1 mL syringe.

Plants were grown 4-5 weeks under a 16 h light cycle prior to infiltration. Leaves were harvested 5 days post-infiltration, flash frozen and stored at −80° C. for later processing. Biological replicates consisted of several leaves all from different tobacco plants. For substrate infiltration studies, generally, 100 μM of (−)-matairesinol in 0.1% DMSO in water was infiltrated into the underside of previously Agrobacterium-infiltrated leaves with a needleless 1 mL syringe 4 days post-infiltration. Leaves were harvested 1 day later, flash frozen and stored at −80° C. for later processing.

Pathway Reconstitution in N. benthamiana

Full reconstitution of the (−)-deoxypodophyllotoxin pathway starting from (+)-pinoresinol in N. benthamiana was achieved by transient expression of DIR (not required), PLR, SDH, CYP719A23, OMT3, CYP71CU1, OMT1 and 2-ODD (FIG. 22) following the transient expression procedure above using an $OD_{600}$=0.3 for each strain.

Transient expression of GFP ($OD_{600}$=total $OD_{600}$ for all pathway genes) was used as a control. For substrate infiltration, 100 μM (+)-pinoresinol (~10 μg per leaf) in 0.1% DMSO in water was infiltrated into the underside of previously Agrobacterium-infiltrated leaves with a needleless 1 mL syringe 4 days postinfiltration. Leaves were harvested 1 day later, flash frozen and stored at ~80° C. for later processing.

Full reconstitution of the (−)-epipodophyllotoxin (FIGS. 29) and (−)-4' desmethylepipodophyllotoxin pathway (FIG. 15B) starting from (+)-pinoresinol in N. benthamiana was achieved by the additional transient expression of CYP82D61, and CYP82D61 and CYP71BE54, respectively. Standard curves for (−)-deoxypodophyllotoxin and (−)-epipodophyllotoxin based on UV absorption at 280 nm, and (−)-4'-desmethyl-epipodophyllotoxin based on ion abundance were constructed and used to quantify amounts produced in N. benthamiana.

Metabolite Extraction

Frozen leaf tissues were lyophilized to dryness. The samples were homogenized on a ball mill (Retsch MM 400) using 5 mm diameter stainless steel beads, shaking at 25 Hz for 2 min. 20 μL for tobacco or 250 μL for P. hexandrum of an 80:20 MeOH/H2O solution was added per milligram of dry tissue, and the mixture was heated at 65° C. for 10 min and filtered through 0.45 μm PTFE filters before liquid chromatography-mass spectrometry (LC-MS) analysis.

For initial studies in the reconstitution of the (−)-pluviatolide pathway in tobacco, β-glucosidase treatment was performed before metabolite analysis. The leaf extracts from above were briefly spun in a microcentrifuge and 200 μL of supernatant was removed and dried under a stream of nitrogen. Residues were resuspended with 200 μL of 0.1 M sodium acetate, pH=5.0 with 2 mg/mL of β-glucosidase from almonds (Sigma-Aldrich) and incubated at 37° C. for 16 h. The solutions were extracted with 2 volumes of ethyl acetate and the organic phase was dried under a stream of nitrogen. 200 μL of an 80:20 MeOH/H2O solution was added to the residue, and the mixture was heated at 65° C. for 10 min and analyzed by LC-MS analysis.

LC-MS Analysis of Metabolite Extracts

Metabolomics samples were analyzed by reversed-phase chromatography on an Agilent 1260 HPLC, using a 5 μm, 2×100 mm Gemini NX-C18 column (Phenomenex). Water with 0.05% acetic acid (A) and ACN with 0.05% acetic acid (B) [negative ion mode] or water with 0.1% FA (A) and ACN with 0.1% FA (B) [positive ion mode] were used as the mobile phase components at a flow rate of 0.4 mL/min with the following 41 min gradient: 0-30 min, 3-50% B; 30-31 min, 50-97% B; 31-36 min, 97% B; 36-37 min, 97-3% B; 37-41 min, 3% B. A coupled Agilent 6520 Accurate-Mass Q-TOF ESI mass spectrometer was used to collect MS data in either positive ion mode or negative ion mode (parameters: mass range: 100-1700 m/z; drying gas: 300° C., 1 L/min; nebulizer: 25 psig; capillary: 3500 V; fragmentor: 150 V; skimmer: 65 V; octupole 1 RF Vpp: 750 V; 1000 ms per spectrum). The first minute of each run was discarded to avoid salt contamination of the MS apparatus. For tandem mass spectrometry (MS/MS) analysis, 5, 10, 20 and 40 V collision energies were used with an m/z window of 1.3 centered on the m/z analyzed.

Metabolomics and MS Data Analysis

HRMS data were analyzed using MassHunter Qualitative Analysis software (Agilent) and XCMS (Scripps Center for Metabolomics, Smith C. A. et al.). For untargeted metabolomics, MassHunter (Agilent) data files were converted to mzXML format using trapper (Seattle Proteome Center). Grouped mzXML files were preprocessed and analyzed by XCMS, using the following sample R script:
library(xcms)
xset<-xcmsSet( )
xset<-group(xset)
xset2<-retcor(xset,family="s",plottype="m")
xset2<-group(xset2)
xset3<-retcor(xset2,family="s",plottype="m")
xset3<-group(xset3)
xset4<-retcor(xset3,family="s",plottype="m")
xset4<-group(xset4,bw=10)
xset5<-fillPeaks(xset4)
reporttab<-diffreport(xset5,"cyp719a23+omt3", "cyp719a23","cyp719a23+omt3 VS cyp719a23",2000)

The resulting report contains a mass peak list with m/z values, peak intensity fold change, statistical significance (p value, two-tailed unequal variance Student's t-test), retention times and extracted peak intensities. The list was filtered using cutoff criteria (generally, p value less than 0.05, t value greater than 0, fold change greater than 5, retention time less than 1800 s and average peak intensity greater than $5 \times 10^4$ in the experimental sample group [in the above case, cyp719a23+omt3]) to yield a narrow list for further analysis. A summary of XCMS results can be found in FIG. 33.

Generally, ion abundances were determined by manual integration of EICs using the MassHunter Qualitative Analysis software. For FIG. 2, they were derived from XCMS analysis.

Heterologous Expression and Purification of OMT3, OMT1 and 2-ODD pET28a:OMT3 was transformed into BL21 (DE3) E. coli. Transformants were grown on LB plates containing 50 μg/mL kanamycin. A single colony was inoculated into 40 mL of LB medium containing 50 μg/mL kanamycin and grown for 16 h at 30° C. The overnight culture was inoculated into 2 L of LB medium containing 50 μg/mL kanamycin and grown at 37° C. until $OD_{600}$=0.6, at which point the culture was cooled to 25° C., and induced with 500 μM IPTG. The culture was further incubated at 25° C. for 6 h, cooled in ice water and centrifuged at 10,800 g for 10 min at 4oC. The supernatant was discarded and the pellet was resuspended in 40 mL of lysis buffer (50 mM sodium phosphate, pH=8.0 and 300 mM NaCl) containing 10 mM imidazole and 20 mM of β-mercaptoethanol. The cell slurry was passed through a French press (Thermo) three times and centrifuged at 38,700 g for 30 min at 4° C. All subsequent manipulations were performed at 4° C. The supernatant was incubated with 1 mL of Ni-NTA agarose resin (Qiagen) pre-equilibrated with lysis buffer containing 10 mM imidazole for 1 h. The slurry was run through a fritted column and protein was eluted with lysis buffer containing increasing imidazole concentrations up to 400 mM. Fractions containing purified protein as determined by SDS-PAGE gel were combined, concentrated and buffer exchanged into 50 mM sodium phosphate, pH=7.5, 100 mM NaCl, 2 mM DTT and 10% glycerol using Amicon Ultra-15 centrifugal filter units, 10 kDa cutoff (Millipore). Total protein content was estimated by measuring UV absorbance at 280 nm on a NanoDrop 1000 spectrophotometer.

Purified protein was flash-frozen as pellets in liquid nitrogen and kept at −80° C. for long term storage. The above protocol was also followed for the expression and purification of OMT1 from BL21 (DE3) E. coli harboring pET24b:OMT1.

The above protocol was also followed for the expression and purification of 2-ODD from BL21 (DE3) E. coli harboring pET24b:2-ODD except for the following changes: the 2 L culture at $OD_{600}$=0.6 was cooled to 16° C. and induced with 100 μM IPTG. The culture was further incubated at 16° C. for 24 h and cooled in ice water before proceeding with purification.

Expression of Cytochromes P450 and Microsome Isolation from S. cerevisiae WAT11

The pYeDP60 constructs were individually transformed into Saccharomyces cerevisiae WAT11 (carrying a chromosomal copy of the A. thaliana ATR1 cytochrome P450 reductase gene) using the lithium acetate method (Gietz et al., 2007). Yeast growth, induction and microsome preparation were performed according to Pompon et al. Microsomes enriched with P450 were isolated in 50 mM Tris-Cl, pH=7.4, 20% glycerol, 1 mM EDTA, flash-frozen as pellets in liquid nitrogen and kept at −80° C. for long term storage. Total protein content was estimated by measuring UV absorbance at 280 nm on a NanoDrop 1000 spectrophotometer.

In vitro Characterization of Recombinant OMT3

For steady state enzyme kinetics, enzyme assays (140 μl reaction volume) contained 10 μg/mL of purified OMT3, 1 mM SAM, (−)-pluviatolide at various concentrations (0.5, 1, 1.5, 2, 3, 5, 10 and 20 μM from a 100% DMSO stock; final concentration of DMSO was kept constant at 5%) and 100 mM NaCl in sodium phosphate buffer (50 mM, pH 7.4). Reactions were initiated by the addition of enzyme and incubated at 22° C. Assays lacking enzyme or SAM served as negative controls. 20 μL aliquots from the reaction were quenched by the addition of 1 volume of acetonitrile with 0.1% TFA at various time points (0.5, 1, 1.5, 2, 3, 4, 6, 8 and 16 min; time points were chosen based on the starting substrate concentration), and clarified by centrifugation for 10 min at 17,000 g. Quenched samples were analyzed by reversed-phase chromatography on an Agilent 1100 HPLC with an Agilent 1260 diode array detector and a 2.7 μm, 3 Å~50 mm Poroshell 120 EC-C18 column (Agilent). Water with 0.1% TFA (A) and ACN with 0.1% TFA (B) were used as the mobile phase components at a flow rate of 0.6 mL/min with the following gradient: 0-2 min, 3-20% B; 2-8 min, 20-60% B; 8-8.5 min, 60-97% B; 8.5-10 min, 97% B; 10-11 min, 97-3% B; 11-15 min, 3% B. The absorption at 280 nm was monitored to detect (−)-pluviatolide and (−)-5'-desmethoxy-yatein, and the peak area response observed was analyzed by Chemstation software (Agilent). A standard curve for (−)-pluviatolide was made in order to determine its extinction coefficient. Because the extinction coefficient for (−)-5'-desmethoxyyatein was estimated to be similar to (−)-pluviatolide due to a similar change in absorbance during kinetic assays, kinetic rates were determined by measuring the rate of (−)-pluviatolide consumption. Experiments were repeated in triplicate and the data points were fit to a linear line using linear regression with GraphPad Prism 6. Only the linear portion of the data, dependent on initial substrate concentration, was used. The initial velocity of the reaction was determined from the slope of the fitted line. The kinetic constants for OMT3 and (−)-pluviatolide, apparent $K_m$ and $v_{max}$, were determined by non-linear regression.

For determining substrate specificity, (+)-pinoresinol (400 μM), (−)-matairesinol (40 μM) and (−)-arctigenin (40 μM) were also tested as substrates under the same assay conditions. Reactions were quenched after 2 h.

In vitro Assays of CYP71CU1, OMT1, 2-ODD and CYP71BE54

CYP71CU1-microsome assays contained 1 mg/mL of CYP71CU1-microsomes, 1 mM NADPH, 30 or 50 μM of substrate and 100 mM NaCl in sodium phosphate buffer (50 mM, pH 7.4). Assays with microsomes from WAT11 harboring an empty vector or lacking NADPH served as negative controls. OMT1 enzyme assays contained 10 μg/mL of purified OMT1, 1 mM SAM, 30 or 50 μM of substrate and 100 mM NaCl in sodium phosphate buffer (50 mM, pH 7.4). Assay lacking SAM served as negative control. Enzyme assays with both CYP71CU1-microsomes and OMT1 contained 1 mg/mL of CYP71CU1-microsomes, 1 mM NADPH, 10 μg/mL of purified OMT1, 1 mM SAM, 30 or 50 μM of substrate and 100 mM NaCl in sodium phosphate buffer (50 mM, pH 7.4).

2-ODD enzyme assays contained 5 μg/mL of purified 2-ODD, 10 mM 2-oxoglutarate, 10 mM ascorbic acid, 0.5 mM FeSO4, 30 μM of substrate and 100 mM NaCl in sodium phosphate buffer (50 mM, pH 7.4). Assays lacking enzyme or 2-oxoglutarate served as negative controls.

CYP71BE54-microsome assays contained 4 mg/mL of CYP71BE54-microsomes, 1 mM NADPH, 50 μM of substrate and 100 mM NaCl in sodium phosphate buffer (50 mM, pH 7.4). Assays with microsomes from WAT11 harboring an empty vector or lacking NADPH served as negative controls.

All substrates [(−)-matairesinol, (−)-arctigenin, (−)-pluviatolide, (−)-5'-desmethoxy-yatein, (−)-yatein, (−)-deoxypodophyllotoxin, and (−)-podophyllotoxin] were derived from a 100% DMSO stock; final concentration of DMSO in enzyme assays was kept constant at 5%. Total reaction volumes were 50 μL. Reactions were initiated by the addition of enzyme and incubated at 30° C.

After 2 h of incubation, reactions were quenched by the addition of 1 volume of acetonitrile with 0.1% TFA and clarified by centrifugation for 10 min at 17,000 g. Quenched samples were either analyzed by HPLC as above for the in vitro characterization of OMT3 or by LC-MS as above for the analysis of plant metabolite extracts.

Chemicals

Commercially Available (+)-pinoresinol was purchased from ArboNova (Turku, Finland). (−)-podophyllotoxin was purchased from Sigma-Aldrich. NMR solvents were purchased from Cambridge Isotope Laboratories.

General Procedures

Compounds were assayed for purity by LC-MS and $^1$H NMR. $^1$H NMR spectra were acquired at room temperature on a Varian 400 MHz spectrometer. Shifts are reported in parts per million downfield from tetramethylsilane and referenced to the residual solvent peak. All NMR spectra can be found in FIG. 34A-G.

Isolation of (−)-matairesinol and (−)-arctigenin from Forsythia x intermedia

Leaves from Forysthia x intermedia 'Northern Sun' (Forestfarm, Williams, Oreg.) were harvested, flash frozen and lyophilized (5.6 g). Leaves were crushed into powder form with mortar and pestle in liquid nitrogen and heated at 65° C. for 45 min in 300 mL of methanol. The extract was filtered and dried under reduced pressure. The residue was resuspended with 100 mL of 0.1 M sodium acetate, pH=5.0 containing 1 mg/mL of β-glucosidase from almonds (Sigma- Aldrich) and incubated at 37° C. for 24 h. The solution was extracted 3 times with 1 volume of ethyl acetate and the organic phase was filtered and dried under reduced pressure. The residue was further purified by preparative HPLC using an Agilent 1260 Infinity preparative-scale HPLC system with an Agilent 1100 diode array detector and a TARGA C18 10 μm 250 Å~20 mm column (Higgins Analytical). Water with 0.1% TFA (A) and acetonitrile with 0.1% TFA (B) were used as the mobile phase components at a flow rate of 36 mL/min with the following method: 0-5 min, 3-25% B; 5-20 min, 25-40% B; 20-22 min, 40% B; 22-23 min, 40-97% B; 23-25 min, 97% B; 25-26 min, 97-3% B. 84 mg of (−)-matairesinol and 94 mg of (−)-arctigenin were isolated.

(−)-matairesinol: $^1$H NMR (400 MHz, Chloroform-d) δ 2.40-2.64 (m, 4H), 2.87 (dd, J=14.1, 6.9 Hz, 1H), 2.95 (dd, J=14.1, 5.2 Hz, 1H), 3.80 (s, 3H), 3.81 (s, 3H), 3.88 (dd, J=9.1, 7.3 Hz, 1H), 4.07-4.19 (m, 1H), 5.57 (s, 1H), 5.59 (s, 1H), 6.40 (d, J=1.9 Hz, 1H), 6.50 (dd, J=8.0, 1.9 Hz, 1H), 6.58-6.60 (m, 1H), 6.61 (s, 1H), 6.79 (d, J=7.8 Hz, 1H), 6.81 (d, J=8.0 Hz, 1H); UV/Vis: Relative absorbance maximum at λ=282 nm; HRMS (m/z): [M+H]$^+$ calcd. for $C_{20}H_{23}O_6^+$, 359.1489; found, 359.1490; [α]$_D$=−32.3 (c=0.62, acetone) {Umezawa et al., 1991. [α]$_D$=−44 (c=0.62, acetone)}.

(−)-arctigenin: $^1$H NMR (400 MHz, Chloroform-d) δ 2.40-2.68 (m, 4H), 2.89 (dd, J=14.1, 6.6 Hz, 1H), 2.94 (dd, J=14.1, 5.3 Hz, 3H), 3.80 (s, 6H), 3.84 (s, 3H), 3.88 (dd, J=9.6, 1.8 Hz, 1H), 4.06-4.17 (m, 1H), 5.60 (s, 1H), 6.45 (d, J=2.1 Hz, 1H), 6.54 (dd, J=8.1, 2.1 Hz, 1H), 6.58-6.64 (m, 2H), 6.74 (d, J=8.1 Hz, 1H), 6.81 (d, J=7.9 Hz, 1H); UV/Vis: Relative absorbance maximum at λ=280 nm; HRMS (m/z): [M+H]$^+$ calcd. for $C_{21}H_{25}O_6^+$, 373.1646; found, 373.1641.

Synthesis of (−)-Pluviatolide Using *S. cerevisiae* WAT11 Cells Expressing CYP719A23

Following Pompon et al. (1996) and Giddings et al. (2011), a 1 L culture of *S. cerevisiae* WAT11 harboring pYeDP60:CYP719A23 was grown and induced, and 6 h after induction, the culture was supplemented with (−)-matairesinol at a final concentration of 100 μM from a 100 mM stock in DMSO. 24 h after induction, the culture was centrifuged at 10,800 g for 15 min at 4° C. The supernatant was extracted 3 times with 1 volume of ethyl acetate and the organic phase was filtered and concentrated under reduced pressure. The desired product was further purified from the crude mixture by silica gel flash column chromatography with ethyl acetate:hexanes (1:1) and preparative HPLC using the same method used for (−)-matairesinol and (−)-arctigenin isolation. Compound was assayed for purity by LC-MS and $^1$H NMR. 5 mg of (−)-pluviatolide was isolated.

(−)-pluviatolide: $^1$H NMR (400 MHz, Chloroform-d) δ 2.39-2.65 (m, 4H), 2.88 (dd, J=14.1, 6.8 Hz, 1H), 2.95 (dd, J=14.0, 5.0 Hz, 1H), 3.84 (s, 3H), 3.85-3.91 (m, 1H), 4.06-4.15 (m, 1H), 5.92 (s, 2H), 6.41-6.48 (m, 2H), 6.58-6.71 (m, 3H), 6.83 (d, J=8.0 Hz, 1H); UV/Vis: Relative absorbance maximum at λ=284 nm; HRMS (m/z): [M+H]$^+$ calcd. for $C_{20}H_{21}O_6^+$, 357.1333; found, 357.1326.

Isolation of OMT3 Enzymatic Product [(−)-5'-desmethoxy-yatein]

A scaled-up enzyme reaction was utilized to generate sufficient amounts of product for $^1$H NMR analysis. The reaction mixture, containing 50 mM sodium phosphate (pH=7.4), 100 mM NaCl, 280 μM pluviatolide, 1 mM SAM and 50 μg/mL of OMT3, was incubated at room temperature for 3 h. The reaction was extracted 3 times with 1 volume of ethyl acetate and the organic phase was dried with sodium sulfate, filtered and dried under reduced pressure. The residue was further purified by preparative HPLC using the same method used for (−)-matairesinol and (−)-arctigenin isolation. Compound was assayed for purity by LC-MS and $^1$H NMR. 4.4 mg of (−)-5'-desmethoxy-yatein was isolated.

(−)-5'-desmethoxy-yatein: $^1$H NMR (400 MHz, Chloroform-d) δ 2.39-2.65 (m, 4H), 2.89 (dd, J=14.1, 7.0 Hz, 1H), 2.97 (dd, J=14.1, 5.1 Hz, 1H), 3.83 (s, 3H), 3.86 (s, 3H), 3.87-3.89 (m, 1H), 4.12 (dd, J=9.1, 6.7 Hz, 1H), 5.92 (d, J=1.5 Hz, 1H), 5.93 (d, J=1.4 Hz, 1H), 6.42-6.48 (m, 2H), 6.63-6.71 (m, 3H), 6.76-6.81 (m, 1H); Relative absorbance maximum at λ=284 nm; HRMS (m/z): [M+H]$^+$ calcd. for $C_{21}H_{23}O_6^+$, 371.1489; found, 371.1480.

Isolation of (−)-deoxypodophyllotoxin and (−)-yatein from *Anthriscus sylvestris*

Shoots and rhizomes from *A. sylvestris* (Digging Dog Nursery, Albion, Calif.) were harvested, washed to remove soil, and lyophilized (~20 g dry weight). Dried plant material was soaked in ~10 mL of methanol per g of tissue for 16 h and then sonicated for 30 min. Methanolic extracts were removed and an additional 10 mL of methanol per g of tissue was added, sonicated for 30 min and repeated once more. The combined methanolic extracts were filtered and dried under reduced pressure. The residue was partially purified by preparative HPLC as above using the following method: 0-30 min, 3-50% B; 30-31 min, 50-97% B; 31-35 min, 97% B; 35-36 min, 97-3% B. The crude mixture was further purified by silica gel flash column chromatography with a mobile phase of ethyl acetate:hexanes (3:7 to 1:1). The remaining crude product was separated once more by preparative HPLC yielding 29.4 mg of (−)-deoxypodophyllotoxin and 3.5 mg of (−)-yatein. Compounds were assayed for purity by LC-MS and $^1$H NMR.

(−)-yatein: $^1$H NMR (400 MHz, Chloroform-d) δ 2.41-2.66 (m, 4H), 2.83-2.97 (m, 2H), 3.83 (s, 9H), 3.88 (dd, J=9.2, 7.5 Hz, 1H), 4.18 (dd, J=9.1, 7.2 Hz, 1H), 5.93 (d, J=1.5 Hz, 1H), 5.94 (d, J=1.4 Hz, 1H), 6.35 (s, 2H), 6.43-6.50 (m, 2H), 6.69 (d, J=7.7 Hz, 1H); Relative absorbance maximum at λ=286 nm; HRMS (m/z): [M+H]$^+$ calcd. for $C_{22}H_{25}O_7^+$, 401.1595; found, 401.1586; [α]$_D$=−16.6 (c=0.32, chloroform) {Miyata et al., 1998 [α]$_D$=−28.4 (c=0.32, chloroform)}.

(−)-deoxypodophyllotoxin: $^1$H NMR (400 MHz, Chloroform-d) δ 2.69-2.82 (m, 3H), 3.01-3.12 (m, 1H), 3.73 (s, 6H), 3.79 (s, 3H), 3.85-3.97 (m, 1H), 4.41-4.51 (m, 1H), 4.58 (d, J=3.2 Hz, 1H), 5.92 (d, J=1.3 Hz, 1H), 5.94 (d, J=1.4 Hz, 2H), 6.33 (s, 2H), 6.50 (s, 1H), 6.66 (s, 1H); Relative absorbance maximum at λ=292 nm; HRMS (m/z): [M+H]$^+$ calcd. for $C_{22}H_{23}O_7^+$, 399.1438; found, 399.1435; [α]$_D$=−81.8 (c=0.63, methanol) {Kawazu et al., 1997 [α]$_D$=−66.6 (c=0.63, methanol)}.

Synthesis of (−)-epipodophyllotoxin and (−)-4'-desmethyl-epipodophyllotoxin

Following Kamal et al. (2000), (−)-epipodophyllotoxin and (−)-4'-desmethyl epipodophyllotoxin were synthesized in two separate reactions starting with 10 mg (−)-podophyllotoxin. Crude reactions were purified by silica gel flash column chromatography with a mobile phase of ethyl acetate:hexanes (3:2), and further purified by preparative HPLC using the same method used for (−)-yatein and (−) deoxypodophyllotoxin isolation, yielding 7.9 mg of (−)-epipodophyllotoxin and 1.3 mg of (−)-4'-desmethyl-epi-podophyllotoxin. Compounds were assayed for purity by LCMS and $^1$H NMR.

(−)-epipodophyllotoxin: $^1$H NMR (400 MHz, Chloroform-d) δ 2.76-2.90 (m, 1H), 3.28 (dd, J=14.1, 5.2 Hz, 1H), 3.73 (s, 6H), 3.79 (s, 3H), 4.31-4.43 (m, 2H), 4.61 (d, J=5.2 Hz, 1H), 4.87 (d, J=3.4 Hz, 1H), 5.97 (d, J=1.3 Hz, 1H), 6.00 (d, J=1.3 Hz, 1H), 6.27 (s, 2H), 6.54 (s, 1H), 6.88 (s, 1H);

Relative absorbance maximum at λ=288 nm; HRMS (m/z): [M+H]$^+$ calcd. for $C_{22}H_{23}O_8^+$, 415.1387; found, 415.1388.

(−)-4'-desmethyl-epipodophyllotoxin: $^1$H NMR (400 MHz, Chloroform-d) δ 2.73-2.86 (m, 1H), 3.25 (dd, J=14.2, 5.1 Hz, 1H), 3.75 (s, 6H), 4.30-4.41 (m, 2H), 4.59 (d, J=5.0 Hz, 1H), 4.82-4.87 (m, 1H), 5.38 (s, 1H), 5.95 (d, J=1.7 Hz, 1H), 5.98 (d, J=1.7 Hz, 4H), 6.27 (s, 2H), 6.53 (s, 1H), 6.85 (s, 1H); Relative absorbance maximum at λ=284 nm; HRMS (m/z): [M+H]$^+$ calcd. for $C_{21}H_{21}O_8^+$, 401.1231; found, 401.1235.

EXAMPLES

The following examples are put forth so as to provide those of ordinary skill in the art with a complete disclosure and description of how to make and use the present invention; they are not intended to limit the scope of what the inventors regard as their invention. Unless indicated otherwise, part are parts by weight, molecular weight is average molecular weight, temperature is in degrees Centigrade, and pressure is at or near atmospheric.

Example 1

Development of an in Planta (−)-Podophyllotoxin Gene Discovery Platform (*N. benthamiana* Platform)

In general, plant biosynthetic pathway elucidation is hampered by challenges in the heterologous production of plant enzymes in typical prokaryotic expression hosts, and the synthesis or isolation of biosynthetic pathway intermediates.

*Agrobacterium*-Mediated Transient Expression in *N. benthamiana*

*Agrobacterium*-mediated transient expression in *N. benthamiana* was chosen as a platform to test candidate genes for the podophyllotoxin pathway, since it offers a robust solution for two reasons. (i) A versatile plant host, such as *N. benthamiana*, likely improves the chances of getting correctly folded, active proteins from a variety of enzymatic superfamilies. (ii) Rapid, combinatorial expression of candidate enzymes can be performed in order to test biochemical and computational predictions without knowing the order of steps or the identities of metabolic intermediates. Though primarily used in pathway discovery to verify the activities of newly identified enzymes by in planta pathway reconstitution, *Agrobacterium*-mediated transient expression in *N. benthamiana* represents a simple and rapid means of simultaneously producing active protein candidates of interest and known pathway intermediates as their substrates.

This can be accomplished by co-infiltrating multiple *Agrobacterium* strains, each harboring a different expression construct, and analyzing the resulting plant tissue extracts using untargeted metabolomics to identify new products.

Production of the Pathway Intermediate (−)-Pluviatolide (−)-Pluviatolide (see FIG. 1), the product of the last characterized pathway enzyme, CYP719A23, was obtained by transient expression of known podophyllotoxin biosynthetic enzymes in *N. benthamiana*. Three of the four known podophyllotoxin biosynthetic enzymes—PLR, SDH and CYP719A23 (DIR was not required)—were cloned from *P. hexandrum* leaf cDNA into pEAQ-HT and transiently expressed in *N. benthamiana* leaves by Agrobacterium infiltration.

(−)-Pluviatolide was not observed in tobacco leaves expressing GFP alone. Although subsequent LC-MS analysis of the resulting leaf extracts revealed low levels of (−)-pluviatolide, the amount was insufficient for detecting downstream intermediates produced when co-expressing candidate enzymes (FIG. 2). The low (−)-pluviatolide titer was assumed to be due to a metabolic bottleneck in the endogenous *N. benthamiana* phenylpropanoid pathway that provides pinoresinol as a substrate.

Co-expression of DIR did not notably increase lignan content. In order to enhance (−)-pluviatolide production in planta, lignan intermediates were infiltrated into tobacco leaves for further conversion by transiently expressed enzymes. Leaves expressing CYP719A23 were infiltrated with micromolar quantities of (−)-matairesinol, isolated from *Forsythia* x *intermedia*, five days after *Agrobacterium* infiltration. After one day, (−)-pluviatolide concentrations were ~75× greater than in tobacco leaves expressing PLR, SDH, and CYP719A23 without substrate infiltration (FIG. 3), providing sufficient (−)-pluviatolide to enable candidate enzyme screening.

Example 2

Identification of a Pluviatolide O-Methyltransferase

The above described *N. benthamiana* platform was then utilized to identify an O-methyltransferase (OMT) that can methylate (−)-pluviatolide. A review of the publicly available *P. hexandrum* RNA-sequence data set from the Medicinal Plants Consortium showed that all known podophyllotoxin genes were highly expressed in rhizome, stem and leaf tissues. Therefore, candidate genes were with similar expression profiles were selected (FIG. 4). As the order of steps in the pathway was not known, four putative OMT genes (OMT1-4) were chosen, twelve cytochromes P450 (CYP) and a 2-oxoglutarate/Fe(II)-dependent dioxygenase (2-ODD). (−)-Matairesinol was then infiltrated into leaves co-expressing CYP719A23 and each individual candidate enzyme. LC-MS analysis of the resulting leaf extracts revealed the complete consumption of (−)-pluviatolide in tobacco leaves co-expressing only OMT3 (FIG. 5). By computational comparison of untargeted metabolomics data from tissue extracts, two compound mass signals were identified that were unique to CYP719A23+OMT3 samples relative to CYP719A23 alone. Further characterization indicated that one of these mass ions is derived from (−)-5'-desmethoxy-yatein (FIG. 6). The other mass signal, which was of much lower ion abundance, was predicted to derive from the double methylation of (−)-matairesinol (FIG. 7). Transient expression of OMT3 alone, followed by infiltration of (−)-matairesinol, resulted in even greater amounts of the doubly methylated product, suggesting that this enzyme accepted multiple substrates. OMT3 was recombinantly expressed in *E. coli* and its kinetic parameters for (−)-pluviatolide methylation were: apparent Km=1.4 μM and $k_{cat}$=0.72 s$^{-1}$ (FIG. 8). OMT3 accepted (−)-matairesinol and (−)-arctigenin with much lower efficiency and did not turn over (+)-pinoresinol. These data are consistent with OMT3-catalyzed methylation of pluviatolide to generate (−)-5'-desmethoxy-yatein as the next step in the pathway.

To identify subsequent steps in the pathway, similar assays were performed in which candidate cytochrome P450 enzymes and 2-oxoglutarate dependent (2-ODD) enzymes were co-expressed with CYP719A23 and OMT3 to screen for a potential (−)-5'-desmethoxy-yatein hydroxylase. However, no consumption of (−)-5'-desmethoxy-yatein was observed in any of the leaf extracts. To test whether the set of candidate genes that was chosen based on available transcriptome conditions (leaf, rhizome and stem) was incomplete, new RNA sequencing data were obtained under elicitation conditions that induce lignan biosynthesis in *P. hexandrum* in an effort to better differentiate biosynthetic pathway genes.

Example 3

Expression of Early Podophyllotoxin Biosynthetic Genes after *P. hexandrum* Leaf Wounding A previous report that the expression of early podophyllotoxin biosynthetic genes (DIR, PLR and SDH) is upregulated in *P. hexandrum* leaves after wounding (Wankhede et al., 2013) was verified using qRT-PCR analysis of known pathway genes and OMT3 in a 24-hour time course after tissue wounding (FIG. 9A and FIG. 10). The high similarity in expression patterns between known (−)-podophyllotoxin genes and OMT3 provided additional evidence of the involvement of OMT3 in (−)-podophyllotoxin biosynthesis. In addition, the metabolomes of these leaf samples were profiled by LC-MS. Removal of the leaf from the stem eliminated the possibility of metabolite transport to the leaf. Both (−)-yatein and (−)-deoxypodophyllotoxin, proposed precursors to (−)- podophyllotoxin and (−)-β-peltatin (Kamil & Dewick, 1986a; Kamil & Dewick, 1986b), were observed to accumulate throughout the time course, reaching a maximum level between 12 and 24 h after wounding (FIG. 11). Consistent with previous reports (Marques et al., 2013), neither (−)-podophyllotoxin nor its glucoside were detected in the leaf tissue.

These data indicated that leaf wounding can elicit the biosynthesis of (−)-podophyllotoxin intermediates at the transcript and metabolite level. RNA sequencing was performed on triplicate *P. hexandrum* leaf samples at 0, 3, 9 and 12 h after wounding. A leaf transcriptome was assembled de novo and reads were mapped to assembled transcripts to determine expression levels. On the basis of the predicted enzyme activities required for the missing pathway steps, the transcriptome data were mined for gene sequences encoding OMTs, CYPs, 2-ODDs, and polyphenol oxidases (PPOs).

Example 4

Identification of (−)-Deoxypodophyllotoxin Biosynthetic Genes

A computational analysis based on expression profile similarity with known pathway genes DIR and CYP719A23 and overall expression level yielded seven candidate pathway genes: Phex30848 (2-ODD), Phex32688 (CYP), Phex13114 (OMT1, previously tested), Phex359 (PPO), Phex34339 (PPO), Phex524 (CYP71CU1), and Phex15199 (CYP) (FIG. 12-14). Hierarchical clustering analysis of 336 expressed genes, selected by filtering all data (34384 total genes) by enzyme family, revealed a single clade of 91 genes (see hierarchical cluster in Table 1, Appendix A); further filtering by expression level condensed this clade to 22 genes containing six of these seven candidates, three of four known pathway genes, and OMT3 (FIG. 9B). Six of the seven candidate enzymes were individually co-expressed with CYP719A23 and OMT3 in tobacco leaves to identify a (−)-5'-desmethoxyyatein hydroxylase. Leaves were infiltrated with (−)-matairesinol four days post-infiltration, harvested a day later, and subjected to LC-MS analysis. In samples expressing CYP719A23+OMT3+Phex524 (CYP71CU1), almost complete turnover was observed of (−)-5'-desmethoxy-yatein, the intermediate formed upon co-expression of CYP719A23 with OMT3 (FIG. 15A).

A comparison of the leaf metabolomes revealed two new CYP71CU1-dependent compound mass signals that corresponded to the calculated m/z of (−)-5'-desmethyl-yatein (FIG. 16). MS/MS analysis supported the assignment of these two mass signals to (−)-5'-desmethyl-yatein; the earlier eluting mass signal, in contrast, was likely an in-source fragmentation ion of a parent compound that resulted from further modification of (−)-5'-desmethyl-yatein at the free hydroxyl position by endogenous tobacco enzymes. These data suggested CYP71CU1 as the next step in the pathway, and pointed to the functionalization of the E ring as an intermediate phase in the pathway.

Conversion Of (−)-5'-Desmethyl-Yatein To (−)-Yatein By OMT1

To complete the biosynthesis of (−)-yatein, a proposed key intermediate in the podophyllotoxin pathway (Kamil & Dewick, 1986b), Phex13114 (OMT1) was screened for the ability to methylate (−)-5'- desmethyl-yatein. OMT1 was transiently expressed in combination with CYP719A23, OMT3 and CYP71CU1 in tobacco leaves that were infiltrated with (−)-matairesinol. In methanolic leaf extracts in which OMT1 had been co-expressed, (−)-5'-desmethyl-yatein was no longer detected (FIG. 15A and FIG. 17). Instead, the accumulation of (−)-yatein was observed suggesting that OMT1 converts (−)-5'-desmethyl-yatein to (−)-yatein as the seventh step in the pathway.

The remainder of the pathway involves the key closing of the central six-membered ring in the aryltetralin scaffold and oxidative tailoring. During the initial screening of individual gene candidates by co-expression with CYP719A23 and OMT3 significant consumption of (−)-5'-desmethoxy-yatein was observed in samples expressing Phex30848 (2-ODD). Computational comparison of leaf metabolomes revealed a new 2-ODD-dependent compound mass signal that corresponded to 5'-desmethoxy-deoxypodophyllotoxin bearing the required aryltetralin scaffold (FIG. 18), suggesting that Phex30848 encoded a 2-ODD that was able to catalyze a stereoselective ring closure reaction using (−)-5'-desmethoxy-yatein as a substrate. The reaction likely occurs through the activation of the 7' carbon by hydroxylation, followed by dehydration and a carbon-carbon bond formation via a quinone methide intermediate (FIG. 19).

2-ODD Catalyzes Oxidative Ring Closure

Prior feeding studies (Kamil & Dewick, 1986b) and the *P. hexandrum* wounding metabolomics data, presented herein, suggest that (−)-yatein is the native substrate for ring closure. In a next step, it was tested whether 2-ODD catalyzed the conversion of (−)-yatein to (−)-deoxypodophyllotoxin in planta, utilizing (−)-yatein as the substrate. 2-ODD was transiently expressed in tobacco leaves along with CYP719A23, OMT3, CYP71CU1 and OMT1. Four days post-infiltration, leaves were infiltrated with (−)-matairesinol, harvested a day later and subjected to LC-MS analysis. (−)-Yatein was consumed in a 2-ODD-dependent fashion, and a computational comparison of metabolite extracts confirmed the accumulation of (−)-deoxypodophyllotoxin in tobacco leaves co-expressing 2-ODD (FIG. 15A and FIG. 20). These data suggest that 2-ODD catalyzes the key oxidative ring closure step to establish the core of the aryltetralin scaffold.

Example 5

Biochemical Analysis of (−)-Deoxypodophyllotoxin Biosynthesic Genes

The activities of the newly identified enzymes OMT3, OMT1, CYP71CU1, 2-ODD, CYP71BE54, CYP82D61 were investigated by in-vitro biochemical analysis. Microsomes enriched with Phex524 (CYP71CU1) were isolated after expression in S. cerevisiae WAT11; Phex13114 (OMT1) and Phex30848 (2-ODD) were expressed in E. coli with C-terminal hexahistidine tags and purified to homogeneity using nickel affinity chromatography.

Incubation of (−)-5′-desmethoxy-yatein with CYP71CU1 and NADPH yielded the hydroxylated product, (−)-5′-desmethyl-yatein. Incubation with both CYP71CU1 and OMT1 as well as the cofactors NADPH and SAM yielded (−)-yatein (FIG. 21). Incubation of 2-ODD with (−)-yatein as the substrate in the presence of 2-oxoglutarate and $Fe^{2+}$ yielded (−)-deoxypodophyllotoxin.

All enzymes were tested for substrate specificity by incubation with (−)-matairesinol, (−)-arctigenin and (−)-pluviatolide; 2-ODD was also tested with (−)-5′-desmethoxyyatein. CYP71CU1 and OMT1 were not active on these substrates under identical assay conditions. The inability of CYP71CU1 to hydroxylate (−)-pluviatolide confirms that methylation by OMT3 occurs prior to hydroxylation.

For 2-ODD, some activity was observed on (−)-5′-desmethoxy-yatein as demonstrated in planta, and negligible activity was observed on (−)-pluviatolide compared to (−)-yatein; no other activity was observed.

These data support the assignments of OMT3, CYP71CU1, OMT1, 2-ODD, CYP71BE54 and CYP82D61 and the order of reactions for the complete pathway through (−)-deoxypodophyllotoxin, as described in FIG. 15A and FIG. 22.

Example 6

Identification of a Demethylating P450 and CYP82D61 Involved in P. hexandrum Lignan Biosynthesis Publicly available transcriptome data were reviewed to identify the CYPs that are predominantly and highly expressed in P. hexandrum rhizomes, the plant tissue in which (−)-podophyllotoxin is primarily produced. Six CYP candidates with full coding sequences were identified that matched the selection criteria, as described in FIG. 23, FIG. 35, and FIG. 36. The candidates were screened in N. benthamiana through individual coexpression with the five (−)-deoxypodophyllotoxin biosynthetic genes starting from CYP719A23 and infiltration of (−)-matairesinol.

Comparative metabolomic analysis showed significant consumption of (−)-deoxypodophyllotoxin in leaves coexpressing the candidate enzyme, Ph14372 (CYP71BE54); however, no (−)-podophyllotoxin was detected (FIG. 15A). Instead, the MS/MS data for the two compound mass signals (same mass, but different retention times) that accumulated in a CYP71BE54-dependent fashion correlated to compounds derived from the demethylation of (−)-deoxypodophyllotoxin, formally (−)-4′-desmethyl-deoxypodophyllotoxin (FIG. 24). The earlier eluting mass signal was likely an in-source fragmentation ion of a parent compound that resulted from further modification of (−)-4′-desmethyl-deoxypodophyllotoxin at the free hydroxyl position by endogenous tobacco enzymes. The observed activity of CYP71BE54 suggests that the earlier described occurrence of demethylated lignans in P. hexandrum (Broomhead et al., 1991; Jackson & Dewick, 1984a; Jackson & Dewick, 1984b) is a result of enzymatic demethylation rather than the failure of OMT3 to methylate a portion of the lignan flux. Consistent with this view, CYP71CU1-enriched microsomes cannot accept (−)-pluviatolide as a substrate and needs a fully methylated substrate earlier in the pathway. Despite moderate expression in yeast, isolated CYP71BE54 microsomes showed specificity for (−)-deoxypodophyllotoxin, but not for any other similar substrates (FIG. 25).

Upon screening an additional candidate P450 enzyme, Ph35407 (CYP82D61), significant consumption of (−)-deoxypodophyllotoxin was observed. However, no formation of (−)-podophyllotoxin was detected; instead, its epimer, (-)-epipodophyllotoxin was found to accumulate (FIG. 26).

To confirm the activity of CYP82D61 in the context of the late pathway enzymes, CYP71BE54, CYP82D61, CYP719A23, OMT3, CYP71CU1, OMT1, and 2-ODD were transiently expressed in N. benthamiana leaves that were subsequently infiltrated with (−)-matairesinol. Comparative metabolomics demonstrated the accumulation of (−)-4′-desmethyl-epipodophyllotoxin, along with two other earlier eluting compound mass signals that were likely in source fragmentation ions of parent compounds that resulted from further modification of (−)-4′-desmethyl-epipodophyllotoxin by endogenous tobacco enzymes (FIG. 15A and FIG. 27). Importantly, (−)-4′-desmethylepipodophyllotoxin is the direct precursor to etoposide, currently only accessible by semisynthesis.

Example 7

Biosynthetic Production of 4′-desmethyl-epipodophyllotoxin in N. benthamiana For the reconstitution of the entire pathway in N. benthamiana, DIR, PLR, SDH, CYP719A23, OMT3, CYP71CU1, OMT1, 2-ODD, CYP71BE54 and CYP82D61 were transiently expressed in tobacco leaves that were subsequently infiltrated with 100 µM (+)-pinoresinol, yielding 10.3 ng of (−)-4′-desmethyl-epipodophyllotoxin per mg of plant dry weight (ng/mg DW). Less than 1 ng of product per mg of plant dry weight was obtained without infiltration of (+)-pinoresinol (FIG. 15B, C). The amounts produced were likely higher than what was observed since a portion of the product was derivatized by endogenous tobacco enzymes and, therefore, not quantified.

Full reconstitution of (−)-deoxypodophyllotoxin and (−)-epipodophyllotoxin was also achieved starting from (+)-pinoresinol in N. benthamiana by omitting CYP82D61 and CYP71BE54, and CYP71BE54, respectively (FIG. 28-29). No significant buildup of pathway intermediates was detected in either case (FIG. 30); notably, the yield of (−)-deoxypodophyllotoxin in tobacco (~90 ng/mg DW) was more than one-third of the yield from wound-induced leaves of Podophyllum.

These results establish the feasibility of producing (−)-4′-desmethyl-epipodophyllotoxin, the etoposide aglycone and immediate precursor to etoposide, biosynthetically, using the newly discovered and herein described biosynthetic enzymes, OMT3, CYP71CU1, OMT1, 2-ODD, CYP71BE54 and CYP82D61 in concert with previously identified enzymes, DIR, PLR, SDH, and CYP719A23; 2-ODD catalyzes a novel C—C bond-forming step for stereoselective cyclization to close the aryltetralin scaffold, as well as an unanticipated late-stage, P450-catalyzed unmasking of the E-ring phenol required for the potent activity of etoposide. This provides a simpler and more direct route to etoposide by circumventing the need for Mayapple cultivation as well as the semisynthetic epimerization and demethylation currently required for production (FIG. 31).

Example 8

Reconstitution and Engineering of 4'-desmethyl-epipodophyllotoxin Biosynthesis in *Saccharomyces cerevisiae*

The reconstitution and engineering of the (−)-4'-desmethyl-epipodophyllotoxin biosynthetic pathway will be achieved in a number of different parent *Saccharomyces cerevisiae* strains, for example W303a and CEN.PK2. The genotypes of these strains along with other yeast strains of interest are available at Euroscarf, Frankfurt, Germany.

There are two possible engineering approaches to be taken. Approach 1. The first option is to heterologously express all genes that are required to convert (+)-pinoresinol to the desired product: PLR (Dinkova-Kostova et al., 1996; SDH (Xia et al., 2001); CYP719A23 (Marques et al., 2013), OMT3, CYP71CU1, OMT1, 2-ODD, CYP71BE54 and CYP82D61. The yeast culture is then supplemented with the substrate, pinoresinol, to achieve biosynthesis.

Approach 2. In addition to the expression of the genes listed in approach 1, an additional set of genes is heterogenously expressed to enable de novo biosynthesis of the entire pathway without supplementation of a substrate. This will require the additional incorporation of the following phenylpropanoid and early lignan biosynthetic genes to convert phenylalanine to pinoresinol: PAL (Wanner et al., 1995); C4H (Mizutani et al., 1997); 4CL (Ehlting et al., 1999); HCT (Hoffmann et al., 2003); REF8 (Schoch et al., 2001); CCoAOMT7 (Wils et al., 2013); CCR1 (Lauvergeat et al., 2001); CAD4 (Sibout et al., 2003); LAC (Turlapati et al., 2011); and DIR (Davin et al., 1997).

All discovered biosynthetic genes will be codon-optimized for expression in S. cerevisiae and synthesized by a gene synthesis company. To express heterologous genes from P. hexandrum in the parent yeast strain, a number of DNA integration constructs will be made using modern molecular biology procedures. They will be comprised of the open reading frame of the codon-optimized gene flanked by a yeast endogenous promoter and terminator, cloned from the genomic DNA of the parent strain. Typical promoters that have previously been used in plant pathway engineering in yeast include GAL1, GAL10, PGK1, TDH3, and TEF1 (Thodey et al., 2014; Paddon et al, 2013; Brown et al., 2015). Typical terminators include CYC1, ADH1, and PGK1. Each DNA integration construct will also contain a selection marker that will allow for growth in the absence of a specific nutrient based on the genotype of the parent strain (for example, tryptophan, uracil, adenine, etc.).

More than one biosynthetic gene can be present in a single construct. The desired integration sequence (promoter, gene, terminator, selection marker, etc.) will be flanked with 500 bp upstream and downstream of the desired integration site in the yeast genome. The amplicons of the desired DNA integrations will then be transformed into yeast stepwise and successful integration events will be selected by growth without the presence of a specific nutrient based on the selection marker. The selection marker can later be removed and re-used by known molecular biology techniques.

Once verified that all genes are functionally expressed and product is successfully produced in vivo, further genetic manipulations will be performed to maximize biosynthetic production. This includes varying the copy number of genes in the pathway and over-expression of native genes for enhanced production of limiting substrates, co-factors such as S-adenosyl methionine and co-substrates such as 2-oxoglutarate.

Although the foregoing invention and its embodiments have been described in some detail by way of illustration and example for purposes of clarity of understanding, it is readily apparent to those of ordinary skill in the art in light of the teachings of this invention that certain changes and modifications may be made thereto without departing from the spirit or scope of the appended claims. Accordingly, the preceding merely illustrates the principles of the invention. It will be appreciated that those skilled in the art will be able to devise various arrangements which, although not explicitly described or shown herein, embody the principles of the invention and are included within its spirit and scope.

APPENDICES

In addition to the above description, Appendix A is hereby incorporated in its entirety as Table 1, showing a hierarchical cluster of 91 genes.

REFERENCES

Broomhead A. J. et al., Matairesinol as precursor of Podophyllum lignans. Phytochemistry 30, 1489-1492 (1991).
Bhattacharyya D. et al., De novo transcriptome analysis using 454 pyrosequencing of the Himalayan Mayapple, *Podophyllum hexandrum*, BMC genomics 14.1 (2013): 748 (2013).
Brown S. et al., De novo production of the plantderived alkaloid strictosidine in yeast. Proceedings of the National Academy of Sciences 112, 3205-3210 (2015).
Canel C. et al., Podophyllotoxin. Phytochemistry 54, 115-120 (2000).
Cimermancic P. et al., Insights into secondary metabolism from a global analysis of prokaryotic biosynthetic gene clusters. Cell 158, 412-421 (2014).
Davin L. B. et al., Stereoselective bimolecular phenoxy radical coupling by an auxiliary (dirigent) protein without an active center. Science 275, 362-367 (1997).
DeLoache W. C. et al., An enzyme-coupled biosensor enables (S)-reticuline production in yeast from glucose. Nature chemical biology, (2015).
De Luca V. et al., Mining the biodiversity of plants: a revolution in the making. Science 336, 1658-1661 (2012).
Dinkova-Kostova A. T. et al., (+)- Pinoresinol/(+)-lariciresinol reductase from *Forsythia intermedia* protein purification, cDNA cloning, heterologous expression and comparison to isoflavone reductase. Journal of Biological Chemistry 271, 29473-29482 (1996).
Engler C. et al., A one pot, one step, precision cloning method with high throughput capability, PloS one 3.11, e3647 (2008).
Ehlting, J. et al., Three 4-coumarate:coenzyme A ligases in Arabidopsis thaliana represent two evolutionarily divergent classes in angiosperms. The Plant Journal 19, 9-20 (1999).
Gibson D. G. et al., Enzymatic assembly of DNA molecules up to several hundred kilobases, Nature methods 6.5, 343-345 (2009).

Gietz, R. Daniel, and Robert H. Schiestl. High-efficiency yeast transformation using the LiAc/SS carrier DNA/PEG method. Nature protocols 2.1 (2007): 31-34.

Giddings L.-A. et al., A stereoselective hydroxylation step of alkaloid biosynthesis by a unique cytochrome P450 in *Catharanthus roseus*, Journal of Biological Chemistry 286.19, 16751-16757 (2011).

Gordaliza M. et al., Podophyllotoxin: distribution, sources, applications and new cytotoxic derivatives. Toxicon 44, 441-459 (2004).

Hoffmann L. et al., Journal of Biological Chemistry 278, 95-103 (2003).

Huang X. & Madan A., CAP3: A DNA sequence assembly program, Genome research 9.9, 868-877 (1999).

Jackson D. E. & Dewick P. M., Aryltetralin lignans from *Podophyllum hexandrum* and *Podophyllum peltatum*. Phytochemistry 23, 1147-1152 (1984a).

Jackson D. E. & Dewick P. M., Biosynthesis of Podophyllum lignans—II. Interconversions of aryltetralin lignans in *Podophyllum hexandrum*. Phytochemistry 23, 1037-1042 (1984b).

Kamal A. et al., Facile and efficient one-pot synthesis of 4β-arylaminopodophyllotoxins: synthesis of DNA topoisomerase II inhibitors (NPF and W-68), Bioorganic & medicinal chemistry letters 10.18, 2059-2062 (2000).

Kamil W. M. & Dewick P. M., Biosynthesis of the lignans α-and β-peltatin. Phytochemistry 25, 2089-2092 (1986a).

Kamil W. M. & Dewick P. M., Biosynthetic relationship of aryltetralin lactone lignans to dibenzylbutyrolactone lignans. Phytochemistry 25, 2093-2102 (1986b).

Kawazu, K., et al. Isolation of the cytotoxic constituent deoxypodophyllotoxin from the leaves of *Juniperus chinensis*. Scientific Reports of the Faculty of Agriculture-Okayama University (Japan) 86 (1997):1-5.

Kumar P. et al., Expression analysis of biosynthetic pathway genes vis-à-vis podophyllotoxin content in *Podophyllum hexandrum* Royle. Protoplasma, 1-10 (2015).

Lata H. et al., Protocols for In Vitro Cultures and Secondary Metabolite Analysis of Aromatic and Medicinal Plants. Springer, pp. 387-402 (2009).

Lauvergeat V., et al., Two cinnamoyl-CoA reductase (CCR) genes from *Arabidopsis thaliana* are differentially expressed during development and in response to infection with pathogenic bacteria. Phytochemistry 57, 1187-1195 (2001).

Li, W. & Godzik A., Cd-hit: a fast program for clustering and comparing large sets of protein or nucleotide sequences, Bioinformatics 22.13, 1658-1659 (2006).

Malik S. et al., Biotechnological approaches for producing aryltetralin lignans from *Linum* species. Phytochemistry Reviews 13, 893-913 (2014).

Marques J. V. et al., Next generation sequencing in predicting gene function in podophyllotoxin biosynthesis. Journal of Biological Chemistry 288, 466-479 (2013).

Miyata, Masaru, Kazutaka Itoh, and Sanro Tachibana. Extractives of Juniperus chinensis L. I: Isolation of podophyllotoxin and yatein from the leaves of *J. chinensis*. Journal of wood science 44.5 (1998): 397-400.

Mizutani M. et al., Isolation of a cDNA and a Genomic Clone Encoding Cinnamate 4-Hydroxylase from Arabidopsis and Its Expression Manner in planta. Plant Physiology 113, 755-763 (1997).

Paddon C. J. et al., High-level semi-synthetic production of the potent antimalarial artemisinin. Nature 496, 528-532 (2013).

Pompon D. et al., Yeast expression of animal and plant P450s in optimized redox environments." Methods in enzymology 272.B, 51-64 (1996).

Qu Y. et al., Completion of the seven-step pathway from tabersonine to the anticancer drug precursor vindoline and its assembly in yeast. Proceedings of the National Academy of Sciences 112, 6224-6229 (2015).

Rajesh M. et al., Agrobacterium-mediated transformation of the medicinal plant *Podophyllum hexandrum* Royle (syn. P. emodi Wall. ex Hook. f. & Thomas). Plant Cell, Tissue and Organ Culture (PCTOC) 114, 71-82 (2013).

Roberts A. & Pachter L., Streaming fragment assignment for real-time analysis of sequencing experiments, Nature methods 10.1, 71-73 (2013).

Robinson M. D. et al., edgeR: a Bioconductor package for differential expression analysis of digital gene expression data, Bioinformatics 26.1, 139-140 (2010).

Sainsbury F. et al., pEAQ: versatile expression vectors for easy and quick transient expression of heterologous proteins in plants. Plant biotechnology journal, 7(7), 682-693 (2009).

Schmittgen T. D. & Kenneth J. L., Analyzing real-time PCR data by the comparative CT method. Nature protocols 3.6, 1101-1108 (2008).

Schoch G. et al., CYP98A3 from Arabidopsis thaliana is a 3'-hydroxylase of phenolic esters, a missing link in the phenylpropanoid pathway. Journal of Biological Chemistry 276, 36566-36574 (2001).

Schulz M. H. et al., Oases: robust de novo RNA-seq assembly across the dynamic range of expression levels, Bioinformatics 28.8, 1086-1092 (2012).

Smith C. A. et al., XCMS: processing mass spectrometry data for metabolite profiling using nonlinear peak alignment, matching, and identification, Analytical chemistry 78.3, 779-787 (2006).

Sibout R. et al., Expression pattern of two paralogs encoding cinnamyl alcohol dehydrogenases in arabidopsis. isolation and characterization of the corresponding mutants. Plant Physiology 132, 848-860 (2003).

Stähelin H. F. & von Wartburg A., The chemical and biological route from podophyllotoxin glucoside to etoposide: Ninth Cain Memorial Award Lecture. Cancer Research 51, 5-15 (1991).

Subramani R. et al., Estimation of nuclear genome size of important medicinal plant species from western Himalaya using flow cytometry. Journal of Cell and Plant Sciences 2, 19-23 (2011).

Teoh K. H. et al., Molecular cloning of an aldehyde dehydrogenase implicated in artemisinin biosynthesis in Artemisia annua Botany, 87(6), 635-642 (2009).

Thodey K. et al., A microbial biomanufacturing platform for natural and semisynthetic opioids. Nature Chemical Biology 10, 837-844 (2014).

Turlapati P. V. et al., The laccase multigene family in *Arabidopsis thaliana*: towards addressing the mystery of their gene function(s). Planta 233, 439-470 (2011).

Umezawa, Toshiaki, Laurence B. Davin, and Norman G. Lewis. Formation of lignans (−)-secoisolariciresinol and (−)-matairesinol with Forsythia intermedia cell-free extracts. Journal of Biological Chemistry 266.16 (1991): 10210-10217.

Wanner L. A. et al., The phenylalanine ammonia-lyase gene family in *Arabidopsis thaliana*. Plant Molecular Biology 27, 327-338 (1995).

Wankhede D. P. et al., Expressed sequence tags and molecular cloning and characterization of gene encoding pinoresinol/lariciresinol reductase from *Podophyllum hexandrum*. Protoplasma 250, 1239-1249 (2013).

Wils C. R., et al. A single amino acid determines position specificity of an *Arabidopsis thaliana* CCoAOMT-like O-methyltransferase. FEBS letters 587(6), 683-689 (2013).

Xia Z.-Q. et al., Secoisolariciresinol dehydrogenase purification, cloning, and functional expression implications for human health protection. Journal of Biological Chemistry 276, 12614-12623 (2001).

What is claimed is:

1. A genetically engineered host cell for use in biosynthesis of a podophyllotoxin intermediate or podophyllotoxin derivative, comprising:
 operably linked to a promoter, at least one nucleic acid molecules having at least 70% sequence identity to a sequence selected from SEQ ID NOS: 4-8 and encoding at least one polypeptide involved in the biosynthesis of podophyllotoxin intermediates and derivatives,
 wherein the biosynthesis is initiated with a starting material suitable to produce the podophyllotoxin intermediate or podophyllotoxin derivative, and
 wherein the biosynthesis is completed with the recovery of the podophyllotoxin intermediate or podophyllotoxin derivative from the host cell.

2. The host cell in accordance to claim 1, wherein the at least one nucleic acid molecule encoding at least one polypeptide involved in biosynthetically producing podophyllotoxin intermediates or podophyllotoxin derivatives has a sequence selected from SEQ ID NOS: 4-8.

3. The host cell in accordance to claim 1, wherein the at least one polypeptide is selected from the group consisting of O-methyltransferase 3 (OMT3), CYP71CU1, O-methyltransferase 1 (OMT1), 2-oxoglutarate/Fe(II)-dependent dioxygenases (2-ODD), and CYP71BE54.

4. The host cell in accordance to claim 1, wherein the podophyllotoxin intermediate or podophyllotoxin derivative is 5'-desmethoxy-yatein, 5'-desmethyl-yatein, yatein, deoxypodophyllotoxin, or 4'-desmethyl-deoxypodophyllotoxin.

5. The host cell in accordance to claim 3, wherein the at least one polypeptide is OMT3 and is encoded by a nucleic acid molecule having at least 70% sequence identity to SEQ ID No: 4.

6. The host cell in accordance to claim 5, wherein said polypeptide has at least 90% sequence identity to the amino acid sequence for OMT3 set forth in SEQ ID No: 11.

7. The host cell in accordance to claim 3, wherein the at least one polypeptide is CYP71CU1 and is encoded by a nucleic acid molecule having at least 70% sequence identity to SEQ ID No: 5.

8. The host cell in accordance to claim 7, wherein said polypeptide has at least 90% sequence identity to the amino acid sequence for CYP71CU1 set forth in SEQ ID No: 12.

9. The host cell in accordance to claim 3, wherein the at least one polypeptide is OMT1 and is encoded by a nucleic acid molecule having at least 70% sequence identity to SEQ ID No: 6.

10. The host cell in accordance to claim 9, wherein said polypeptide has at least 90% sequence identity to the amino acid sequence for OMT1 set forth in SEQ ID No: 13.

11. The host cell in accordance to claim 3, wherein the at least one polypeptide is 2-ODD and is encoded by a nucleic acid molecule having at least 70% sequence identity to SEQ ID No: 7.

12. The host cell in accordance to claim 11, wherein said polypeptide has at least 90% sequence identity to the amino acid sequence for 2-ODD set forth in SEQ ID No: 14.

13. The host cell in accordance to claim 3, wherein the at least one polypeptide is CYP71BE54 and is encoded by a nucleic acid molecule having at least 70% sequence identity to SEQ ID No: 8.

14. The host cell in accordance to claim 13, wherein said polypeptide has at least 90% sequence identity to the amino acid sequence for CYP71BE54 set forth in SEQ ID No: 15.

15. The host cell in accordance to claim 1, comprising OMT3 or, operably linked to a promoter, a nucleic acid molecule having at least 70% sequence identity to SEQ ID NO: 4, and wherein the podophyllotoxin intermediate or derivative is 5'-desmethoxy-yatein.

16. The host cell in accordance to claim 1, comprising CYP71CU1 or, operably linked to a promoter, a nucleic acid molecule having at least 70% sequence identity to SEQ ID NO: 5, and wherein the podophyllotoxin intermediate or derivative is 5'-desmethyl-yatein.

17. The host cell in accordance to claim 1, comprising OMT1 or, operably linked to a promoter, a nucleic acid molecule having at least 70% sequence identity to SEQ ID NO: 6, and wherein the podophyllotoxin intermediate or derivative is yatein.

18. The host cell in accordance to claim 1, comprising 2-ODD or, operably linked to a promoter, a nucleic acid molecule having at least 70% sequence identity to SEQ ID NO: 7, and wherein the podophyllotoxin intermediate or derivative is deoxypodophyllotoxin.

19. The host cell in accordance to claim 1, comprising CYP71BE54 or, operably linked to a promoter, a nucleic acid molecule having at least 70% sequence identity to SEQ ID NO: 8, and wherein the podophyllotoxin intermediate or derivative is 4'-desmethyl-deoxypodophyllotoxin.

* * * * *